(12) United States Patent
Block et al.

(10) Patent No.: US 12,084,482 B2
(45) Date of Patent: Sep. 10, 2024

(54) FUSION PROTEINS OF NATURAL HUMAN PROTEIN FRAGMENTS TO CREATE ORDERLY MULTIMERIZED IMMUNOGLOBULIN Fc COMPOSITIONS

(71) Applicant: Gliknik Inc., Baltimore, MD (US)

(72) Inventors: David S. Block, Baltimore, MD (US); Henrik Olsen, Baltimore, MD (US)

(73) Assignee: Gliknik Inc., Baltimore, MD (US)

( * ) Notice: Subject to any disclaimer, the term of this patent is extended or adjusted under 35 U.S.C. 154(b) by 603 days.

(21) Appl. No.: 17/400,367

(22) Filed: Aug. 12, 2021

(65) Prior Publication Data

US 2022/0056087 A1    Feb. 24, 2022

Related U.S. Application Data

(62) Division of application No. 15/642,175, filed on Jul. 5, 2017, now Pat. No. 11,117,940, which is a division of application No. 13/812,269, filed as application No. PCT/US2011/045768 on Jul. 28, 2011, now abandoned.

(60) Provisional application No. 61/368,465, filed on Jul. 28, 2010.

(51) Int. Cl.
| | |
|---|---|
| *A61K 39/395* | (2006.01) |
| *A61K 31/573* | (2006.01) |
| *A61K 45/06* | (2006.01) |
| *A61P 37/00* | (2006.01) |
| *C07K 14/47* | (2006.01) |
| *C07K 16/00* | (2006.01) |
| *A61K 39/00* | (2006.01) |

(52) U.S. Cl.
CPC ............ *C07K 14/47* (2013.01); *A61K 31/573* (2013.01); *A61K 39/395* (2013.01); *A61K 45/06* (2013.01); *A61P 37/00* (2018.01); *C07K 16/00* (2013.01); *A61K 2039/505* (2013.01); *C07K 2317/35* (2013.01); *C07K 2317/52* (2013.01); *C07K 2317/92* (2013.01); *C07K 2319/30* (2013.01); *C07K 2319/73* (2013.01); *C07K 2319/735* (2013.01)

(58) Field of Classification Search
None
See application file for complete search history.

(56) References Cited

U.S. PATENT DOCUMENTS

| | | | |
|---|---|---|---|
| 5,681,566 A | 10/1997 | Stevenson | |
| 5,877,396 A | 3/1999 | Ravetch et al. | |
| 6,004,781 A | 12/1999 | Seed | |
| 6,660,266 B1 | 12/2003 | Mosser et al. | |
| 7,148,321 B2 | 12/2006 | Gillies et al. | |
| 7,511,121 B2 | 3/2009 | Arnason et al. | |
| 7,524,487 B2 | 4/2009 | Mosser et al. | |
| 7,666,622 B2 | 2/2010 | Sharma et al. | |
| 8,258,263 B2 | 9/2012 | Morrison et al. | |
| 8,680,237 B2 | 3/2014 | Strome et al. | |
| 9,512,208 B2 | 12/2016 | Strome et al. | |
| 9,512,210 B2 | 12/2016 | Strome et al. | |
| 9,683,044 B2 | 6/2017 | Block et al. | |
| 9,926,362 B2 | 3/2018 | Strome et al. | |
| 10,208,105 B2 | 2/2019 | Strome et al. | |
| 10,851,154 B2 | 12/2020 | Strome et al. | |
| 10,941,191 B2 | 3/2021 | Strome et al. | |
| 11,034,775 B2 | 6/2021 | Olsen et al. | |
| 11,117,940 B2 | 9/2021 | Block et al. | |
| 11,331,372 B2 | 5/2022 | Block et al. | |
| 2002/0115157 A1 | 8/2002 | Davis et al. | |
| 2002/0142374 A1 | 10/2002 | Gallo et al. | |
| 2002/0147326 A1 | 10/2002 | Chaikin et al. | |
| 2003/0044423 A1 | 3/2003 | Gillies et al. | |
| 2003/0118592 A1 | 6/2003 | Ledbetter et al. | |
| 2003/0216546 A1 | 11/2003 | Tykocinski et al. | |
| 2003/0235578 A1 | 12/2003 | Stinson et al. | |
| 2004/0062763 A1 | 4/2004 | Mosser et al. | |
| 2004/0110226 A1 | 6/2004 | Lazar et al. | |
| 2004/0147731 A1 | 7/2004 | Parkos | |
| 2004/0151725 A1 | 8/2004 | Gray et al. | |
| 2004/0265321 A1 | 12/2004 | Johnson et al. | |
| 2005/0033029 A1 | 2/2005 | Lu | |
| 2005/0249723 A1 | 11/2005 | Lazar | |

(Continued)

FOREIGN PATENT DOCUMENTS

| | | |
|---|---|---|
| AU | 2015200330 B2 | 10/2016 |
| EP | 0553667 A1 | 8/1993 |

(Continued)

OTHER PUBLICATIONS

Gelfand. New Engl. J. Med. 2012;367:2015-25. (Year: 2012).*

(Continued)

*Primary Examiner* — Chun W Dahle
(74) *Attorney, Agent, or Firm* — COOLEY LLP

(57) ABSTRACT

The current invention involves a series of fully recombinant multimerized forms of immunoglobulin Fc which thereby present polyvalent immunoglobulin Fc to immune cell receptors. The fusion proteins exist as both homodimeric and highly ordered multimeric fractions, termed stradomers. In comparison to the homodimeric fraction, purified multimeric stradomers have higher affinity and avidity for FcγRs with slower dissociation and are useful in the treatment and prevention of disease. The current invention demonstrates that directly linking IgG1 Fc regions to multimerization domains leads to enhanced multimerization and biological activity.

15 Claims, 33 Drawing Sheets

Specification includes a Sequence Listing.

(56) References Cited

U.S. PATENT DOCUMENTS

| | | |
|---|---|---|
| 2006/0074225 A1 | 4/2006 | Chamberlain et al. |
| 2006/0263856 A1 | 11/2006 | Gillies et al. |
| 2006/0275254 A1 | 12/2006 | Kim et al. |
| 2007/0269369 A1 | 11/2007 | Gegg et al. |
| 2008/0260738 A1 | 10/2008 | Moore et al. |
| 2008/0267980 A1 | 10/2008 | Tomlinson et al. |
| 2009/0104210 A1 | 4/2009 | Tota et al. |
| 2009/0117133 A1 | 5/2009 | Arnason et al. |
| 2009/0136485 A1 | 5/2009 | Chu et al. |
| 2009/0175867 A1 | 7/2009 | Thompson et al. |
| 2009/0217401 A1 | 8/2009 | Korman et al. |
| 2009/0252729 A1 | 10/2009 | Farrington et al. |
| 2009/0258031 A1 | 10/2009 | Karrer et al. |
| 2009/0304696 A1 | 12/2009 | Lawson et al. |
| 2009/0304715 A1 | 12/2009 | Masuho et al. |
| 2010/0048877 A1 | 2/2010 | Ruker et al. |
| 2010/0093979 A1 | 4/2010 | Lazar |
| 2010/0143353 A1 | 6/2010 | Mosser et al. |
| 2010/0227805 A1 | 9/2010 | Karin et al. |
| 2010/0239633 A1 | 9/2010 | Strome et al. |
| 2011/0243966 A1 | 10/2011 | Farrington et al. |
| 2011/0305697 A1 | 12/2011 | Walczak |
| 2012/0283417 A1 | 11/2012 | Mosser et al. |
| 2012/0309941 A1 | 12/2012 | Strome et al. |
| 2013/0156765 A1 | 6/2013 | Block et al. |
| 2014/0072582 A1 | 3/2014 | Block et al. |
| 2014/0105913 A1 | 4/2014 | Strome et al. |
| 2014/0335075 A1 | 11/2014 | Strome et al. |
| 2014/0370012 A1 | 12/2014 | Block et al. |
| 2015/0056185 A1 | 2/2015 | Strome et al. |
| 2016/0280768 A1 | 9/2016 | Strome et al. |
| 2016/0355570 A1 | 12/2016 | Strome et al. |
| 2017/0008951 A1 | 1/2017 | Block et al. |
| 2018/0002388 A1 | 1/2018 | Block et al. |
| 2018/0094061 A1 | 4/2018 | Block et al. |
| 2018/0186862 A1 | 7/2018 | Strome et al. |
| 2019/0218275 A1 | 7/2019 | Strome et al. |
| 2021/0277091 A1 | 9/2021 | Strome et al. |
| 2022/0241372 A1 | 8/2022 | Block et al. |

FOREIGN PATENT DOCUMENTS

| | | |
|---|---|---|
| EP | 0439540 B1 | 6/1995 |
| EP | 2006305 A9 | 7/2009 |
| WO | WO 1990/004413 A1 | 5/1990 |
| WO | WO 1994/003191 A1 | 2/1994 |
| WO | WO 1994/015640 A1 | 7/1994 |
| WO | WO 2000/009560 A2 | 2/2000 |
| WO | WO 2002/056910 A1 | 7/2002 |
| WO | WO 2002/072605 A2 | 9/2002 |
| WO | WO 2002/072608 A2 | 9/2002 |
| WO | WO 2003/010202 A1 | 2/2003 |
| WO | WO 2003/051933 A1 | 6/2003 |
| WO | WO 2003/105898 A1 | 12/2003 |
| WO | WO 2004/062619 A2 | 7/2004 |
| WO | WO 2005/000895 A2 | 1/2005 |
| WO | WO 2005/007809 A2 | 1/2005 |
| WO | WO 2005/077981 A2 | 8/2005 |
| WO | WO 2005/089503 A2 | 9/2005 |
| WO | WO 2006/008739 A2 | 1/2006 |
| WO | WO 2006/061650 A2 | 6/2006 |
| WO | WO 2006/071206 A2 | 7/2006 |
| WO | WO 2006/074199 A1 | 7/2006 |
| WO | WO 2007/021129 A1 | 2/2007 |
| WO | WO 2007/100083 A1 | 9/2007 |
| WO | WO 2008/138131 A1 | 11/2008 |
| WO | WO 2008/151088 A2 | 12/2008 |
| WO | WO 2008/157378 A2 | 12/2008 |
| WO | WO 2010/065578 A2 | 6/2010 |
| WO | WO 2011/060242 A2 | 5/2011 |
| WO | WO 2011/073692 A1 | 6/2011 |
| WO | WO 2012/001647 A2 | 1/2012 |
| WO | WO 2012/016073 A2 | 2/2012 |
| WO | WO 2013/112986 A1 | 8/2013 |
| WO | WO 2014/031646 A2 | 2/2014 |
| WO | WO 2016/073917 A1 | 5/2016 |
| WO | WO-2017019565 A2 | 2/2017 |
| WO | WO-2017176651 A1 | 10/2017 |
| WO | WO-2018107082 A1 | 6/2018 |

OTHER PUBLICATIONS

Rudnick and Adams, "Affinity and Avidity in Antibody-Based Tumor Targeting." Cancer Biotherapy and Radiopharmaceuticals (2009); 24 (2): 155-161.

Stewart, R., et al., "The role of Fc gamma receptors in the activity of immunomodulatory antibodies for cancer." Journal for Immuno Therapy of Cancer (2014); 2: 29, 10 pages.

"Synthetic peptides with high biochemical activity," downloaded on Sep. 7, 2012 from http://www.genosphere-biotech.com/Long-Active-Peptides.html, 1 page.

Abaza, et al., "Effect of amino acid substitutions outside an antigenic site on protein binding to monoclonal antibodies of predetermined specificity obtained by peptide immunization: demonstration with region 94-100 (antigenic site 3) of myoglobin." Journal of Protein Chemistry (1992); 11 (5): 433-444.

Alegre and Fallarino, "Mechanisms of CTLA-4-Ig in tolerane induction." Curr. Pharmaceutical Design (2006); 12 (2): 149-160.

Anderson, C. A. et al., "Cutting Edge: Biasing immune responses by directing antigen to macrophage Fcγ receptors." J. Immunology (2002); 168: 3697-3701.

Aubin, et al., "Indirect inhibition of in vivo and in vitro T-cell responses by intravenous immunoglobulins due to impaired antigen presentation." Blood (2010); 115 (9): 1727-1734.

Augener, et al., "Are aggregates of IgG the effective part of high-dose immunoglobulin therapy in adult idiopathic thrombocytopenia purpura (ITP)?" Blut (1985); 50: 249-252.

Barrionuevo, et al., "Immune complex-FcγR interaction modulates monocyte/macrophage molecules involved in inflammation and immune response." Clin. Exp. Immunol. (2003); 133 (2): 200-207.

Bazin, et al., "Tetramolecular immune complexes are more efficient than IVIg to prevent antibody-dependent in vitro and in vivo and in in vivo phagocytosis of blood cells." British J. Haematol. (2004); 127 (1): 90-96.

Bazin, et al., "Reversal of immune thrombocytopenia in mice by cross-linking human immunoglobulin G with a high-affinity monoclonal antibody". Br J Haematol. (Oct. 2006); 135(1): 97-100. Epub Aug. 22, 2006.

Bleeker, et al., "Vasoactive side effects of intravenous immunoglobulin preparations in a rat model and their treatment with recombinant platelet-activating factor acetylhydrolase". Blood (Mar. 1, 2000);95(5): 1856-1861.

Boyle, J.J., et al., "Solid-Phase Immunoglobulins IgG and IgM Activate Macrophages with Solid-Phase IgM Acting via a Novel Scavenger Receptor A Pathway." The American Journal of Pathology (2012); 181 (1): 347-361.

Braathen, R., et al., "The Carboxyl-terminal Domains of IgA and IgM Direct Isotype-specific Polymerization and Interaction with the Polymeric Immunoglobulin Receptor." The Journal of Biological Chemistry (2002); 277 (45): 42755-42762.

Bruhns, et al., "Specificity and affinity of human Fc receptors and their polymorphic variants for human IgG subclasses." Blood (2009); 113 (16): 3716-3725.

Campbell, A. M., "Monoclonal Antibody Technology," In Laboratory Techniques in Biochemistry and Molecular Biology (1984); vol. 13, Elsevier Science Publishers, pp. 1-32.

Caron, et al., "Engineered Humanized Dimeric Forms of IgG are More Effective Antibodies." J. Exp. Med. (1992); 176: 1191-1195.

Chappel, et al., "Identification of the Fcγ receptor class I binding site in human IgG through the use of recombinant IgG1/IgG2 hybrid and point-mutated antibodies." Proc. Natl. Acad. Sci. USA (1991); 88: 9036-9040.

Chougnet, et al., "Molecular analysis of decreased interleukin-12 production in person infected with human immunodeficiency virus." J. Infectious Diseases (1996); 174: 46-53.

Clynes, Raphael, "Immune complexes as therapy for autoimmunity". J. Clin. Invest. (2005); 115(1): 25-27.

(56) References Cited

OTHER PUBLICATIONS

Cohen, P., "Systemic Autoimmunity," In Fundamental Immunology, 4th edition, Philadelphia, Lippencot-Raven Publishers, pp. 1067-1088 (1999).
Colman, et al., "Effects of amino acid sequence changes on antibody-antigen interactions," Research in Immunology (1994); 145 (1): 33-36.
Constantine, M. M., et al., "Intravenous immunoglobulin utilization in the Canadian Atlantic provinces: a report of the Atlantic Collaborative Intravenous Immune Globulin utilization working group." Transfusion (2007); 47: 2072-2080.
Czajkowsky, D.M., et al., Fc-fusion proteins: new developments and future perspectives. EMBO Molecular Medicine (Oct. 2012); 4(10): 1015-1028. Epub Jul. 26, 2012.
Davidson, et al, "T helper cell1-type CD4+ T cells, but not B cells, mediate colitis in interleukin 10-deficient mice." J. Exp. Med. (1996); 184: 241-251.
Davis, et al., "Intermolecular disulfide bonding in IgM: effects of replacing cysteine residues in the μ heavy chain." EMBO J. (1989); 8 (9): 2519-2526.
De Taeye, et al., "The Ligands for Human IgG and Their Effector Functions". Antibodies (2019); 8(2): 30, 18 pages.
Debré, et al., "Infusion of Fcγ fragments for treatment of children with acute immune thrombocytopeni purpura." Lancet (1993); 342: 945-949.
Deo, Y. M. et al., "Clinical significance of IgG Fc receptors and FcγR-directed immunotherapies." Immunology Today (1997); 18 (3) :127-135.
Dinarello, C. A., "Proinflammatory and anti-inflammatory cytokines as mediators in the pathogenesis of septic shock." Chest (1997); 112: 321S-329S.
European examination report mailed May 18, 2011 in co-pending European application No. 08769936.9, 7 pages.
Extended European Search Report for EP Application No. 13169230.3, dated Oct. 25, 2013, 15 pages.
Extended European Search Report for EP Application No. 13830394.6, dated Mar. 4, 2016, 9 pages.
Extended European Search Report for European Patent Application No. 18166541.5, dated Oct. 18, 2018, 9 pages.
Flanagan, et al., "Soluble Fc Fusion Proteins for Biomedical Research." Meth. Mol. Biol. (2007); 378: 33-52.
Gavin, et al., "Cutting Edge: Identification of the Mouse IgG3 Receptor: Implications for Antibody Effector Function at the Interface Between Innate and Adaptive Immunity." J. Immunol. (1998); 160 (1): 20-23.
Gerber, et al., "Reversing Lipopolysaccharide Toxicity by Ligating the Macrophage Fcγ Receptors." J. Immunology (2001); 166: 6861-6868.
Ghumra, et al., "Structural requirements for the interaction of human IgM and IgA with the human Fcα/μ receptor." Eur. J. Immunol. (2009); 39 (4): 1147-1156.
Gliknik website. www.gliknik.com/research/stradomer.php, 2012.
Goldenberg, "Multiple Sclerosis Review." P&T (2012); 37(3): 175-184.
Greenwood et al., "Engineering multiple domains forms of the therapeutic antibody CAMPATH-1H: Effect on complement Lysis," Ther. Immunol. (1994); 1(5):247-255.
Ha, et al., "Isolation and characterization of IgG1 with asymmetrical Fc glycosylation." Glycobiology (2011); 21 (8): 1087-1096.
Harbury, et al. "A switch between two-, three-, and four-stranded coiled coils in GCN4 leucine zipper mutants." Science (1993); 262: 1401-1407.
Hart, et al., "Comparison of the suppressive effects of interleukin-10 and interleukin-4 on synovial fluid macrophages and blood monocytes from patients with inflammatory arthritis." Immunology (1995); 84: 536-542.
Huang, et al., "In vitro study of combination of rhOPG-Fc and alendronate on inhibition osteoclast." Zhonghua Wai Ke Za Zhi (2005); 43(12):812-816. (Abstract Only, Article in Chinese).

International Preliminary Report on Patentability for International Application No. PCT/US2015/059574, dated May 9, 2017, 12 pages.
International Preliminary Report on Patentability for PCT/US2013/023404, 17 pages, mailed Jul. 29, 2014.
International Preliminary Report on Patentability for PCT/US2013/055800, 23 pages, mailed Feb. 24, 2015.
International Preliminary Report on Patentability, mailed Jan. 29, 2013 in International application No. PCT/US2011/045768, 10 pages.
International Preliminary Report on Patentability, PCT appln. No. PCT/US2008/065428, 8 pages, mailed Dec. 1, 2009.
International Search Report and Written Opinion for International Application No. PCT/US2011/045768, 15 pages, mailed Mar. 8, 2012.
International Search Report and Written Opinion for International Application No. PCT/US2015/059574, mailed Feb. 3, 2016, 14 pages.
International Search Report for PCT/US2008/065428, 5 pages, mailed Feb. 10, 2009.
International Search Report for PCT/US2013/023404, 4 pages, mailed Apr. 15, 2013.
International Search Report for PCT/US2013/055800, 7 pages, mailed Mar. 4, 2014.
Jain, et al., "Fully recombinant IgG2a Fc multimers (stradomers) effectively treat collagen-induced arthritis and prevent idiopathic thrombocytopenia purpura in mice." Arthritis Res. Ther. (2012); 14 (4): R192, 12 pages.
Jain, et al., "Tumour antigen targeted monoclonal antibodies incorporating a novel multimerisation domain significantly enhance antibody dependent cellular cytotoxicity against colon cancer." European Journal of Cancer (2013); 49 (15): 3344-3352.
Jefferis, et al., "Interaction sites on human IgG-Fc for FcγR: current models." Immunol. Lett. (2002); 82 (1-2): 57-65.
Kacskovics, et al., "Fc receptors in livestock species." Vet. Immunol. Immunopathol. (2004); 102: 351-362.
Landschulz, et al., "The Leucine Zipper: A Hypothetical Structure Common to a New Class of DNA Binding Proteins." Science (1988); 240: 1759-1764.
Lee, J. K. "Determination of the Molecular Size Distribution of Immunoglobulin G (IgG) In Intravenous IgG-Albumin Formulations By High-Performance Liquid Chromatography." Journal of Chromatography (1988); 444: 141-152.
Lemieux and Bazin, "Autoantibody-Induced Formation of Immune Complexes in Normal Human Serum." Curr. Pharm Design (2006); 12: 173-179.
Levinson, D. R., "Intravenous Immune Globulin: medicare payment and availability." Report to DHHS, OEI-03-05-00404 (2007).
Liew, "TH1 and TH2 cells: a historical perspective." Nature Reviews, Immunology (2002);2: 55-60.
Lucas, et al., "ERK activation following macrophage FcγR ligation leads to chromatin modifications at the IL-10 locus." Journal of Immunology (2005); 175: 469-477.
Lund, et al., "Multiple Interactions of IgG with Its Core Oligosaccharide Can Modulate Recognition by Complement and Human Fcγ Receptor I and Influence the Synthesis of Its Oligosaccharide Chains." J. Immunol. (1996); 157: 4963-4969.
Meijer, et al., "Pharmacokinetics of Murine Anti-Human CD3 Antibodies in Man Are Determined by the Disappearance of Target Antigen." Journal of Pharmacology and Experimental Therapeutics (2002); 300 (1): 346-353.
Mekhaiel, et al., "Polymeric human Fc-fusion proteins with modified effector functions." Scientific Reports (2011); 1: 124, pp. 1-11.
Monoclonal antibody 13-1 heavy chain-mouse, GenBank Accession # PC4436 (Date: Feb. 4, 1998).
Mosser, D. M., "The Many Faces of Macrophage Activation." J. Leukocyte Biology (2003); 73: 209-212.
Mosser, et al., "Interleukin-10: new perspectives on an old cytokine." Immunological Reviews (2008); 226 (1): 205-218.
Mössner, et al., "Increasing the efficacy of CD20 antibody therapy through the engineering of a new type II anti-CD20 antibody with enhanced direct and immune effector cell-mediated B-cell cytotoxicity." Blood (2010); 115 (22): 4393-4402.

(56) References Cited

OTHER PUBLICATIONS

Nagashima, et al., "Enhanced antibody-dependent cellular phagocytosis by chimeric monoclonal antibodies with tandemly repeated Fc domains." Journal of Bioscience and Bioengineering (2011); 111 (4): 391-396.

Nagashima, et al., "Fc Taryotaika ni yoru Kokassei Kotai." Proc. 126th Ann. Meet. Pharm. Soc. Japan 126:107 (abstract No. P28[S]am-551) (2006).

Nagashima, et al., "Tandemly repeated Fc domain augments binding avidities of antibodies for Fcγ receptors, resulting in enhanced antibody-dependent cellular cytotoxicity." Mol. Immunol. (2008); 45: 2752-2763.

Ngo, et al., "Computational complexity, protein structure prediction, and the levinthal paradox," in the Protein Folding Problem and Tertiary Structure Prediction, Boston: Birkhauser, pp. 433 and 492-495 (1994).

Nimmerjahn and Ravetch, "Antibody-mediated modulation of immune responses." Immunological Rev. (2010); 236: 265-275.

Ong, et al., "How to accelerate the endothelialization of stents." Archives de maladies du coeur et des vaisseaux (2005); 98 (2): 123-126.

Opposition Proceedings No. 2012392760, Notice of Opposition filed by Gliknik, Inc. on Oct. 2, 2018, in Australian Patent Application No. 2012392760 in the name of Liverpool School of Tropical Medicine, 2 pages.

Opposition Proceedings No. 2012392760, Statement of Grounds and Particulars of Opposition filed by Gliknik, Inc. on Jan. 2, 2019, in Australian Patent Application No. 2012392760 in the name of Liverpool School of Tropical Medicine, 11 pages.

Opposition Proceedings No. 2012392760 (Australian Patent Application No. 2012392760 in the name of Liverpool School of Tropical Medicine) filed by Gliknik, Inc. on Jan. 2, 2019, Evidence in Answer in Opposition, Declaration of Anthony Lawrence Shaw (and exhibits ALS-18 and ALS-19 and exhibits ALS-18 and ALS-19) dated and filed Sep. 4, 2019, 14 pages.

Opposition Proceedings No. 2012392760 (Australian Patent Application No. 2012392760 in the name of Liverpool School of Tropical Medicine) filed by Gliknik, Inc. on Jan. 2, 2019, Applicant's Evidence in Answer, Declaration of Sarah Cox (and Exhibit SC1), dated Jul. 2, 2019, and filed Jul. 3, 2019, 36 pages.

Opposition Proceedings No. 2012392760 (Australian Patent Application No. 2012392760 in the name of Liverpool School of Tropical Medicine) filed by Gliknik, Inc. on Jan. 2, 2019, Applicant's Evidence in Answer, Declaration of Dr Beate Peter (and Exhibits BP1-BP9) dated Jul. 2, 2019, and filed Jul. 3, 2019, 147 pages.

Partial European Search Report, EP appl. No. 13169230.3, dated Jul. 31, 2013, 8 pages.

Proceedings of the 126th Annual Meeting of the Pharmaceutical Society of Japan, No. 126 2006, p. 107 (P28[S]am-551) (and Machine translation of pertinent portions), 4 pages.

Ratcliffe et al., "Measurement of the binding activity of defined IgG aggregates to macrophage Fc receptors," Immunology Letters, 7(2):73-76 (1983).

Reeck, et al., "'Homology" in proteins and nucleic acids: a terminology muddle and a way out of it." Cell (Aug. 1987); 50(5): 667.

Reeth et al., "Positive selection vectors to generate fused genes for the expression of his-tagged proteins." BioTechniques (1998); 25: 898-904.

Reff and Heard, "A review of modifications to recombinant antibodies: attempt to increase efficacy in oncology applications." Crit. Rev. Oncol./Hematol. (2001); 40: 25-35.

Rowley, et al., "Engineered hexavalent Fc proteins with enhanced Fc-gamma receptor avidity provide insights into immune-complex interactions." Communications Biology (2018); 1: 146, pp. 1-12.

Rudikoff, et al. "Single amino acid substitution altering antigen-binding specificity." Proceedings of the National Academy of Sciences (1982); 79.6: 1979-1983.

Salfeld, "Isotype selection in antibody engineering." Nat. Biotechnol. (2007); 25: 1369-1372.

Samuelsson, A., et al., "Anti-inflammatory Activity of IVIG Mediated Through the Inhibitory Fc Receptor." Science (Jan. 2001); 291(5503): 484-486.

Schuurman, et al., "The inter-heavy chain disulfide bonds of IgG4 are in equilibrium with intra-chain disulfide bonds." Mol. Immunol. (2001); 38: 1-8.

Shields, et al., "High Resolution Mapping of the Binding Site on Human IgG1 for FcγRI, FCγRII, FCγRIII, and FcRn and Design of IgG1 Variants with Improved Binding to the FcγR," J. Biol. Chem. (2001); 276: 6591-6604.

Siragam, et al., "Can antibodies with specificity for soluble antigens mimic the therapeutic effects of intravenous IgG in the treatment of autoimmune disease?" The Journal of Clinical Investigation (2005); 115 (1): 155-160.

Siragam, et al., "Intravenous immunoglobulin ameliorates ITP via activating Fcγ receptors on dendritc cells." Nature Med. (2006); 12(6):668-692.

Smith and Morrison, "Recombinant polymeric IgG: an approach to engineering more potent antibodies." Biotechnol. (1994); 12: 683-688.

Smith, et al., "Addition of a μ-tailpiece to IgG results in polymeric antibodies with enhanced effector functions including complement-mediated cytolysis by IgG4." J. Immunol. (1995); 154: 2226-2236.

Song, et al., "Monoclonal IgG can ameliorate immune thrombocytopenia in a murine model of ITP: an alternative to IVIG." Blood (2002); 101 (9): 3708-3713.

Sørensen, et al., "Effect of the IgM and IgA secretory tailpieces on polymerization and secretion of IgM and IgG." The Journal of Immunology (Apr. 1996); 156(8): 2858-2865.

Stevenson, G. T. et al., "Engineered antibody for treating lymphoma." Recent Res. Canc. Res. (2002); 159: 104-112.

Sundaram, et al., "Lipopolysaccharide-induced suppression of erythrocyte binding and phagocytosis via FcγRI, FcγRII, FcγRIII, and CR3 receptors in murine macrophages." J. Leukocyte Biology (1993); 54: 81-88.

Supplemental European Search Report for European Application No. 08769936.9, dated May 26, 2010, 9 pages.

Supplemental European Search Report for European Application No. 11813204.2, dated Jul. 3, 2015, 6 pages.

Supplemental European Search Report for European Application No. 13741129.4, dated Nov. 4, 2015, 5 pages.

Sutterwala, et al., "Reversal of Proinflammatory Responses by Ligating the macrophage Fcγ Receptor Type I." Journal of Experimental Medicine (1998); 188 (1): 217-222.

Sutterwala, et al., "Selective Suppression of Interleukin-12 Induction After Macrophage Receptor Litigation." J. Exp. Med. (1985); 185: 1977-1985.

Tankersley, D. L., "Dimer Formation In immunoglobulin Preparations and Speculations On the Mechanism of Action of Intravenous Immune Globulin in Autoimmune Diseases." Immunological Reviews (1994); 39: 159-172.

Teeling, et al., "Therapeutic efficacy of intravenous immunoglobulin preparations depends on the immunoglobulin G dimers: studies in experimental immune thrombocytopenia." Blood (2001); 98 (4): 1095-1099.

Tha-In, et al., "Modulation of the cellular immune system by intravenous immunoglobulin." Trends Immunol. (2008); 29 (12): 608-615.

Thiruppathi, et al., "Recombinant IgG2a Fc (M045) multimers effectively suppress experimental autoimmune myasthenia gravis." J. Autoimmunity (2014); 52 (2): 64-73.

Tremblay, et al., "Picogram doses of lipopolysaccharide exacerbate antibody-mediated thrombocytopenia and reduce the therapeutic efficacy of intravenous immunoglobulins in mice." British Journal of Hematology (2007); 139: 297-302.

Vajdos, et al. "Comprehensive functional maps of the antigen-binding site of an anti-ErbB2 antibody obtained with shotgun scanning mutagenesis." Journal of Molecular Biology (2002); 320 (2): 415-428.

Van Noort and Amor, "Cell Biology of Autoimmune Diseases." International Review of Cytology (1998); 178: 127-205.

(56) References Cited

OTHER PUBLICATIONS

Vialtel, et al., "Nucleation-controlled Polymerization of human Monoclonal Immunoglobulin G Cryoglobulins." The Journal of Biological Chemistry (1982); 257 (7): 3811-3818.
Vidarsson, et al., "IgG subclasses and allotypes: from structure to effector functions." Frontiers in Immunology (2014); 5 (1): 1-17.
Weber, et al., "B-cell activation influences T-cell polarization and outcome of anti-CD20 B-cell depletion in central nervous system autoimmunity." Annals of Neurology (2010); 68 (3): 369-383.
Wei, Xiaoshan et al., "Proteomics studies of autoimmune diseases of the nervous system." Journal of Apoplexy and Nervous Diseases (2009); vol. 26, No. 5, pp. 630-632, and English summary / abstract, 4 pages.
White, D.M., et al., "Design and expression of polymeric immunoglobulin fusion proteins: a strategy for targeting low-affinity Fc gamma receptors." Protein Expression and Purification (Apr. 2001); 21(3): 446-455.
Wright, et al., "Dimeric, Trimeric and Tetrameric Complexes of Immunoglobulin G Fix Complement." Biochem. J. (1980); 187: 775-780.
Written Opinion of the International Searching Authority, PCT appl. No. PCT/US2013/0055800, 22 pages, mailed Mar. 4, 2014.
Written Opinion of the International Searching Authority, PCT appl. No. PCT/US2013/023404, 16 pages, mailed Apr. 15, 2013.
Written Opinion of the International Searching Authority, PCT appln. No. PCT/US2008/065428, 7 pages, mailed Feb. 11, 2009.
Yoo, et al. "Human IgG2 can form covalent dimers." The Journal of Immunology (2003); 170 (6): 3134-3138.
Zang, C., "Annual founders week deemed a 'huge success,'" VOICE University of Maryland, pp. 1-5, http://umvoice.com/2011/12/annual-founders-week-deemed-a-huge-success/, visited website Dec. 10, 2012.
Zhang, et al., "Alteration in the IL-2 signal peptide affects secretion of proteins in vitro and in vivo." Journal Gene Medicine (2005); 7: 354-365.
Zhang, et al., "Dynamic and transient remodeling of the macrophages IL-10 promoter during transcription." Journal of Immunology (2006); 177: 1282-1288.
Arase, et al., "Association with FcR Is Essential for Activation Signal through NKR-P1 (CD161) in Natural Killer (NK) Cells and NK1.1+ T Cells." Journal of Experimental Medicine (1997); 186 (12): 1957-1963.
Asanuma, et al., "Multimerization and collagen binding of vitronectin is modulated by its glycosylation." International Congress Series (2001); vol. 1223, pp. 97-101.
Banki, et al., "Cross-Linking of CD32 Induces Maturation of Human Monocyte-Derived Dendritic Cells Via NF-B Signaling Pathway." The Journal of Immunology (2003); 170 (8): 3963-3970.
Brønsted, et al., "Crosslinked dextran—a new capsule material for colon targeting of drugs." Journal of Controlled Release (Apr. 30, 1998); 53(1-3): 7-13.
Dalakas, et al., "A Controlled Trial of High-Dose Intravenous Immune Globulin Infusions as Treatment for Dermatomyositis." The New England Journal of Medicine (Dec. 30, 1993); 329(27): 1993-2000.
Gajdos, et al., "High-Dose Intravenous Gammaglobulin for Myasthenia Gravis." The Lancet (1984); 323 (8373): 406-407.

Gralnick, et al., "Role of carbohydrate in multimeric structure of factor VIII/von Willebrand factor protein." PNAS (1983); 80 (9): 2771-2774.
Infante, A.J., "Uses (and abuses) of IVIG in immunology, hematology, and rheumatology." Presentation, University of Texas Health Science, Pediatrics Grand Rounds, San Antonio, TX, Feb. 19, 2010, 12 pages.
Jayne, et al., "Treatment of systemic vasculitis with pooled intravenous immunoglobulin." The Lancet (May 11, 1991); 337(8750): 1137-1139.
Jin and Balthasar, "Mechanisms of Intravenous Immunoglobulin Action in Immune Thrombocytopenia Purpura." Human Immunology (Apr. 2005); 66(4): 403-410.
Jukes, et al., "A Newly Developed Chemically Crosslinked Dextran-Poly(Ethylene Glycol) Hydrogel for Cartilage Tissue Engineering." Tissue Engineering Part A (2010); 16(2): 565-573.
LeHoang, et al., "Intravenous immunoglobulin (IVIg) for the treatment of birdshot retinochoroidopathy." Journal Ocular Immunology and Inflammation (Mar. 2000); 8(1): 49-57.
Mendel and Mendel, "Non-specific' binding. The problem, and a solution." Biochemical Journal (1985); 228 (1): 269-272.
Mihaesco and Seligmann, "Papain Digestion Fragments of Human IGM Globulins." Journal of Experimental Medicine (1968); 127 (3): 431-453.
Morris, et al., "Development and characterization of recombinant human Fc:OX40L fusion protein linked via a coiled-coil trimerization domain." Molecular Immunology (2007); 44 (12): 3112-3121.
Nimmerjahn and Ravetch, "Fcγ receptors as regulators of immune responses." Nature Reviews Immunology (2008); 8: 34-47.
Nimmerjahn and Ravetch, "The antiinflammatory activity of IgG: the intravenous IgG paradox." Journal of Experimental Medicine (2007); 204 (1): 11-15.
O'Shea, et al., "Evidence that the leucine zipper is a coiled coil." Science (1989); 243 (4890): 538-542.
Rütter and Luger, "High-dose intravenous immunoglobulins: An approach to treat severe immune-mediated and autoimmune diseases of the skin". J Am Acad Dermatol. (Jun. 2001); 44(6): 1010-1024.
Shields, et al., "Lack of Fucose on Human IgG1 N-Linked Oligosaccharide Improves Binding to Human FcγRIII and Antibody-dependent Cellular Toxicity." The Journal of Biological Chemistry (2002); 277 (30): 26733-26740.
Sultan, et al., "Anti-idiotypic suppression of autoantibodies to factor VIII (antihaemophilic factor) by high-dose intravenous gammaglobulin." The Lancet (Oct. 6, 1984); 2(8406): 765-768.
Van Der Mech, et al., "A Randomized Trial Comparing Intravenous Immune Globulin and Plasma Exchange in Guillain-Barr Syndrome." The New England Journal of Medicine (Apr. 23, 1992); 326(17): 1123-1129.
Woof, et al., "Human antibody-Fc receptor interactions illuminated by crystal structures." Nat Rev Immunol. (Feb. 2004); 4(2): 89-99.
Wright and Morrison, "Effect of C2-Associated Carbohydrate Structure on Ig Effector Function: Studies with Chimeric Mouse-Human IgG1 Antibodies in Glycosylation Mutants of Chinese Hamster Ovary Cells." The Journal of Immunology (1998); 160 (7): 3393-3402.
Zafranskaya, et al., "Interferon-therapy reduces CD4+ and CD8+ T-cell reactivity in multiple sclerosis." Immunology (May 2007); 121(1): 29-39. Epub Dec. 18, 2006.

* cited by examiner

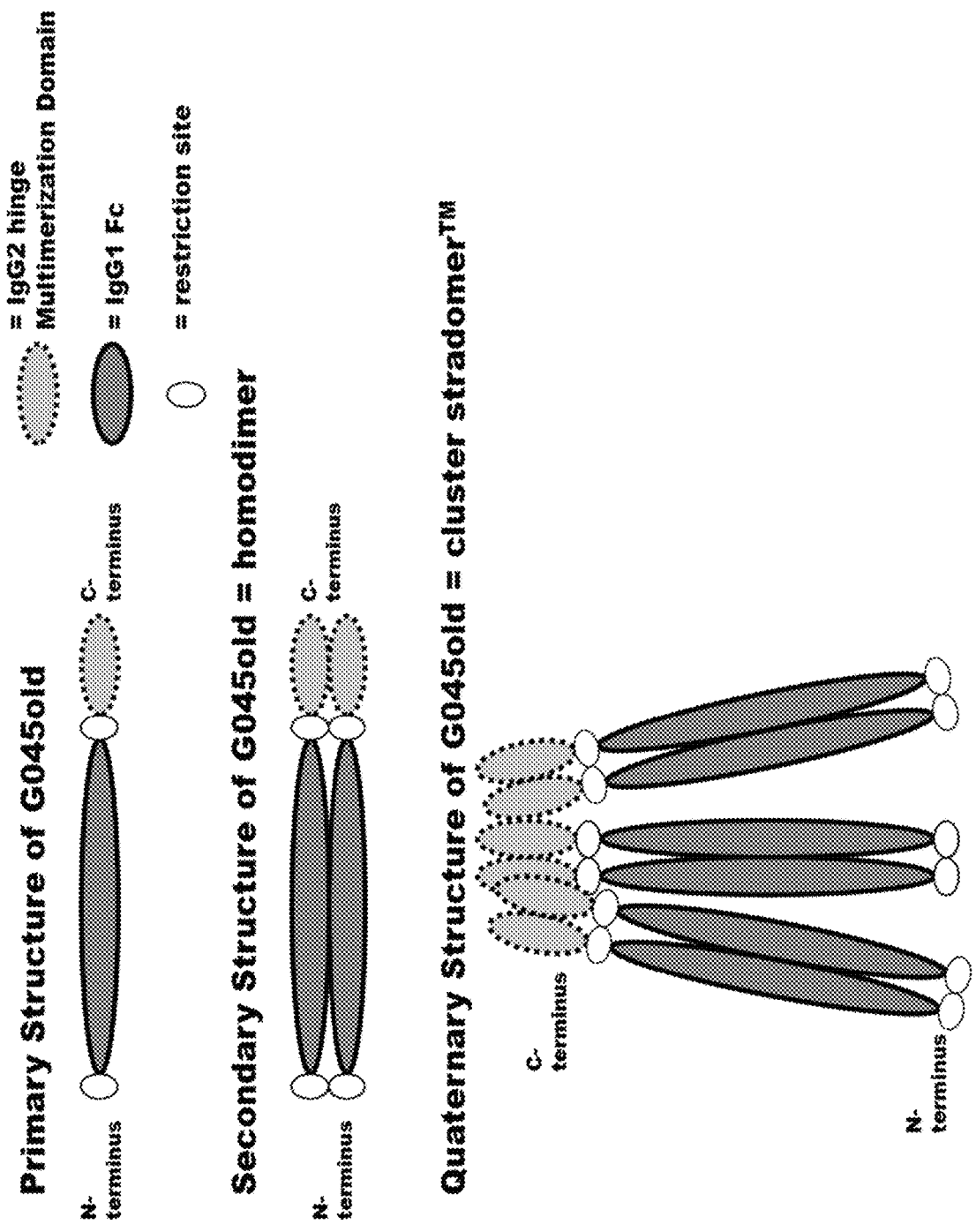

M046

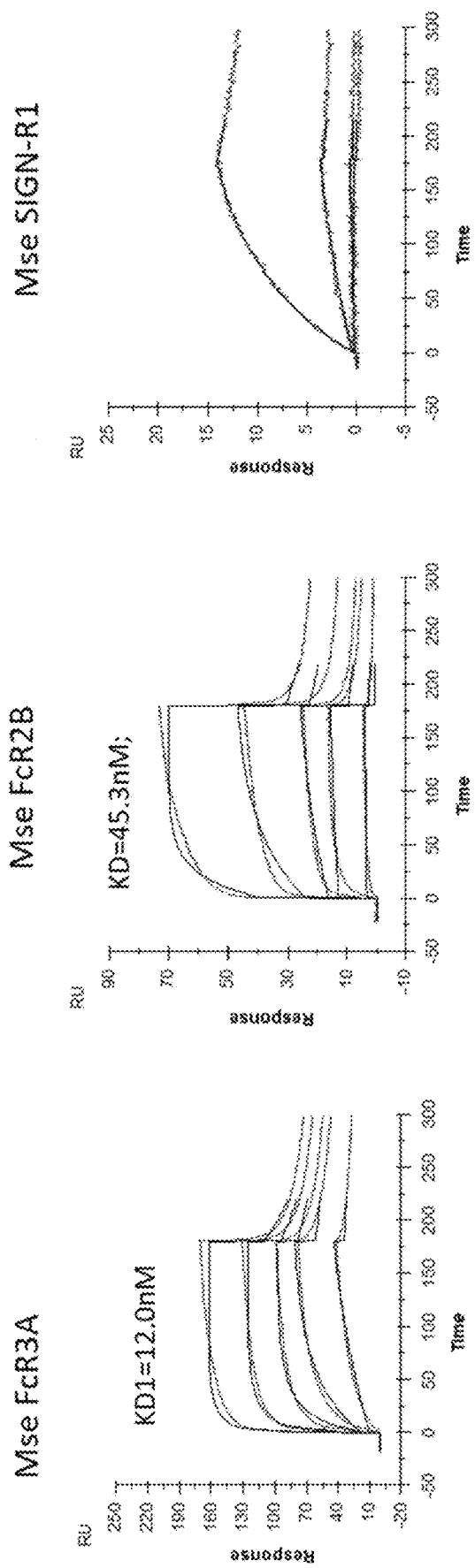

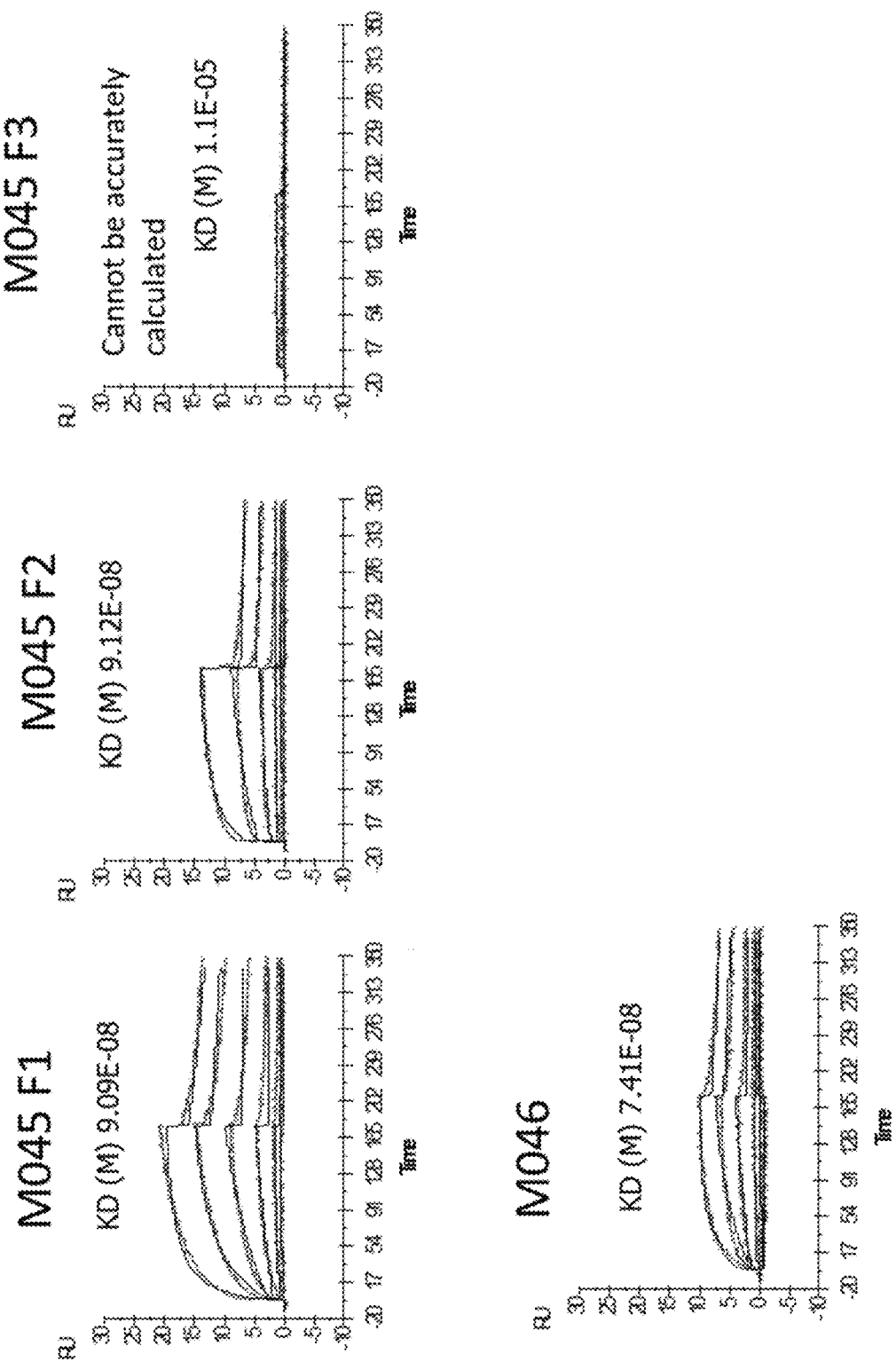

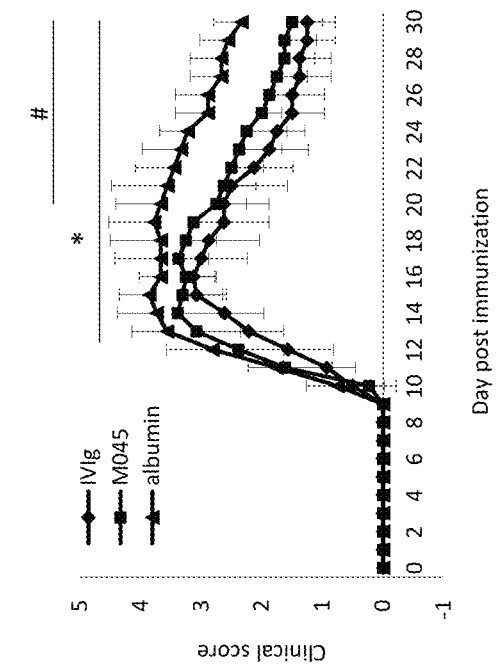
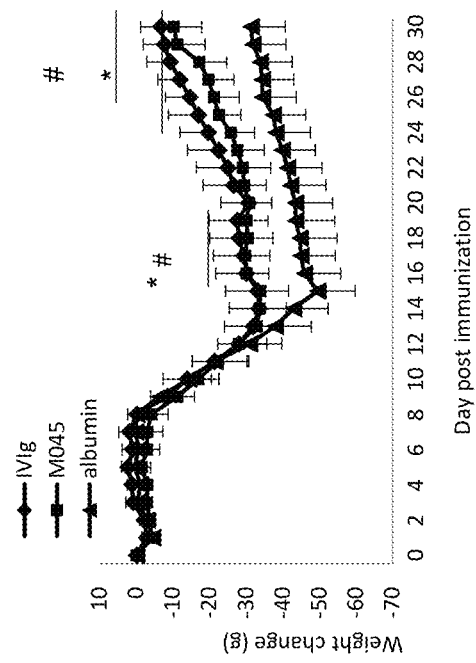
FIG. 12A
FIG. 12B

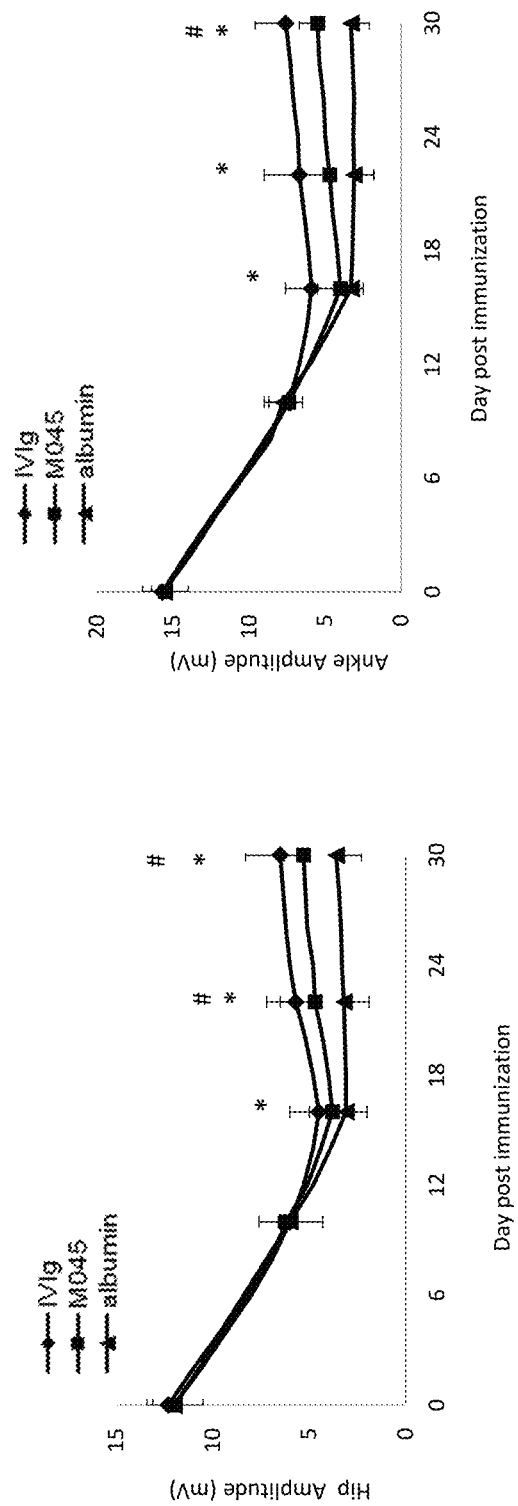

SEQUENCE LISTING

<160> NUMBER OF SEQ ID NOS: 30

<210> SEQ ID NO 1
<211> LENGTH: 20
<212> TYPE: PRT
<213> ORGANISM: Homo sapiens

<400> SEQUENCE: 1

Met Glu Thr Asp Thr Leu Leu Leu Trp Val Leu Leu Leu Trp Val Pro
1               5                   10                  15

Gly Ser Thr Gly
            20

<210> SEQ ID NO 2
<211> LENGTH: 232
<212> TYPE: PRT
<213> ORGANISM: Homo sapiens

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln

-continued

```
                85                  90                  95
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 3
<211> LENGTH: 12
<212> TYPE: PRT
<213> ORGANISM: Homo sapiens

<400> SEQUENCE: 3

Glu Arg Lys Cys Cys Val Glu Cys Pro Pro Cys Pro
1               5                   10

<210> SEQ ID NO 4
<211> LENGTH: 264
<212> TYPE: PRT
<213> ORGANISM: Homo sapiens

<400> SEQUENCE: 4

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
```

```
                165                 170                 175
Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 5
<211> LENGTH: 41
<212> TYPE: PRT
<213> ORGANISM: Homo sapiens

<400> SEQUENCE: 5

Gly Gly Gly Ser Ile Lys Gln Ile Glu Asp Lys Ile Glu Glu Ile Leu
1               5                   10                  15

Ser Lys Ile Tyr His Ile Glu Asn Glu Ile Ala Arg Ile Lys Lys Leu
            20                  25                  30

Ile Gly Glu Arg Gly His Gly Gly Gly
        35                  40

<210> SEQ ID NO 6
<211> LENGTH: 245
<212> TYPE: PRT
<213> ORGANISM: Homo sapiens

<400> SEQUENCE: 6

Asp Ala Ala Asp Ile Gln His Ser Gly Gly Arg Ser Ser Glu Pro Lys
1               5                   10                  15

Ser Cys Asp Lys Thr His Thr Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
```

```
                180               185               190
Pro Pro Val Leu Asp Ser Asp Gly Ser Phe Phe Leu Tyr Ser Lys Leu
        195               200               205

Thr Val Asp Lys Ser Arg Trp Gln Gln Gly Asn Val Phe Ser Cys Ser
        210               215               220

Val Met His Glu Ala Leu His Asn His Tyr Thr Gln Lys Ser Leu Ser
225               230               235               240

Leu Ser Pro Gly Lys
            245

<210> SEQ ID NO 7
<211> LENGTH: 260
<212> TYPE: PRT
<213> ORGANISM: Homo sapiens

<400> SEQUENCE: 7

Asp Ala Ala Asp Ile Gln His Ser Gly Gly Arg Ser Ser Glu Pro Lys
1               5                   10                  15

Ser Cys Asp Lys Thr His Thr Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys Ser Leu Glu Glu Arg Lys Cys Cys Val Glu Cys
                245                 250                 255

Pro Pro Cys Pro
            260

<210> SEQ ID NO 8
<211> LENGTH: 264
<212> TYPE: PRT
<213> ORGANISM: Homo sapiens
```

```
<400> SEQUENCE: 8

Met Glu Thr Asp Thr Leu Leu Leu Trp Val Leu Leu Leu Trp Val Pro
1               5                   10                  15

Gly Ser Thr Gly Glu Arg Lys Cys Cys Val Glu Cys Pro Pro Cys Pro
            20                  25                  30

Glu Pro Lys Ser Cys Asp Lys Thr His Thr Cys Pro Pro Cys Pro Ala
        35                  40                  45

Pro Glu Leu Leu Gly Gly Pro Ser Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Ser His Glu Asp Pro Glu Val Lys Phe Asn Trp Tyr Val
                85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Ala
    130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Pro Gly Lys
            260

<210> SEQ ID NO 9
<211> LENGTH: 294
<212> TYPE: PRT
<213> ORGANISM: Homo sapiens

<400> SEQUENCE: 9

Met Glu Thr Asp Thr Leu Leu Leu Trp Val Leu Leu Leu Trp Val Pro
1               5                   10                  15

Gly Ser Thr Gly Gly Gly Ser Ile Lys Gln Ile Glu Asp Lys Ile Glu
            20                  25                  30

Glu Ile Leu Ser Lys Ile Tyr His Ile Glu Asn Glu Ile Ala Arg Ile
        35                  40                  45

Lys Lys Leu Ile Gly Glu Arg Gly His Gly Gly Ser Ser Glu Pro
    50                  55                  60

Lys Ser Cys Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95
```

```
Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Arg Glu Glu Gln Tyr Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290

<210> SEQ ID NO 10
<211> LENGTH: 289
<212> TYPE: PRT
<213> ORGANISM: Homo sapiens

<400> SEQUENCE: 10

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175
```

```
Phe Tyr Pro Ser Asp Ile Ala Val Glu Trp Glu Ser Asn Gly Gln Pro
            180                 185                 190

Glu Asn Asn Tyr Lys Thr Thr Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Gly Gly Gly Ser
                245                 250                 255

Ile Lys Gln Ile Glu Asp Lys Ile Glu Glu Ile Leu Ser Lys Ile Tyr
            260                 265                 270

His Ile Glu Asn Glu Ile Ala Arg Ile Lys Lys Leu Ile Gly Glu Arg
        275                 280                 285

Gly

<210> SEQ ID NO 11
<211> LENGTH: 266
<212> TYPE: PRT
<213> ORGANISM: Mus sp.

<400> SEQUENCE: 11

Met Glu Thr Asp Thr Leu Leu Leu Trp Val Leu Leu Leu Trp Val Pro
1               5                   10                  15

Gly Ser Thr Gly Asp Glu Pro Arg Gly Pro Thr Ile Lys Pro Cys Pro
            20                  25                  30

Pro Cys Lys Cys Pro Ala Pro Asn Leu Leu Gly Gly Pro Ser Val Phe
        35                  40                  45

Ile Phe Pro Pro Lys Ile Lys Asp Val Leu Met Ile Ser Leu Ser Pro
50                  55                  60

Ile Val Thr Cys Val Val Val Asp Val Ser Glu Asp Asp Pro Asp Val
65                  70                  75                  80

Gln Ile Ser Trp Phe Val Asn Asn Val Glu Val His Thr Ala Gln Thr
                85                  90                  95

Gln Thr His Arg Glu Asp Tyr Asn Ser Thr Leu Arg Val Val Ser Ala
            100                 105                 110

Leu Pro Ile Gln His Gln Asp Trp Met Ser Gly Lys Glu Phe Lys Cys
        115                 120                 125

Lys Val Asn Asn Lys Asp Leu Pro Ala Pro Ile Glu Arg Thr Ile Ser
130                 135                 140

Lys Pro Lys Gly Ser Val Arg Ala Pro Gln Val Tyr Val Leu Pro Pro
145                 150                 155                 160

Pro Glu Glu Glu Met Thr Lys Lys Gln Val Thr Leu Thr Cys Met Val
                165                 170                 175

Thr Asp Phe Met Pro Glu Asp Ile Tyr Val Glu Trp Thr Asn Asn Gly
            180                 185                 190

Lys Thr Glu Leu Asn Tyr Lys Asn Thr Glu Pro Val Leu Asp Ser Asp
        195                 200                 205

Gly Ser Tyr Phe Met Tyr Ser Lys Leu Arg Val Glu Lys Lys Asn Trp
    210                 215                 220

Val Glu Arg Asn Ser Tyr Ser Cys Ser Val Val His Glu Gly Leu His
225                 230                 235                 240

Asn His His Thr Thr Lys Ser Phe Ser Arg Thr Pro Gly Lys Glu Arg
                245                 250                 255
```

```
Lys Cys Cys Val Glu Cys Pro Pro Cys Pro
            260             265
```

<210> SEQ ID NO 12
<211> LENGTH: 278
<212> TYPE: PRT
<213> ORGANISM: Mus sp.

<400> SEQUENCE: 12

```
Met Glu Thr Asp Thr Leu Leu Leu Trp Val Leu Leu Leu Trp Val Pro
1               5                   10                  15

Gly Ser Thr Gly Asp Ala Ala Asp Ile Gln His Ser Gly Gly Arg Ser
            20                  25                  30

Arg Glu Pro Arg Gly Pro Thr Ile Lys Pro Cys Pro Pro Cys Lys Cys
        35                  40                  45

Pro Ala Pro Asn Leu Leu Gly Gly Pro Ser Val Phe Ile Phe Pro Pro
    50                  55                  60

Lys Ile Lys Asp Val Leu Met Ile Ser Leu Ser Pro Ile Val Thr Cys
65                  70                  75                  80

Val Val Val Asp Val Ser Glu Asp Asp Pro Asp Val Gln Ile Ser Trp
                85                  90                  95

Phe Val Asn Asn Val Glu Val His Thr Ala Gln Thr Gln Thr His Arg
            100                 105                 110

Glu Asp Tyr Asn Ser Thr Leu Arg Val Val Ser Ala Leu Pro Ile Gln
        115                 120                 125

His Gln Asp Trp Met Ser Gly Lys Glu Phe Lys Cys Lys Val Asn Asn
    130                 135                 140

Lys Asp Leu Pro Ala Pro Ile Glu Arg Thr Ile Ser Lys Pro Lys Gly
145                 150                 155                 160

Ser Val Arg Ala Pro Gln Val Tyr Val Leu Pro Pro Pro Glu Glu Glu
                165                 170                 175

Met Thr Lys Lys Gln Val Thr Leu Thr Cys Met Val Thr Asp Phe Met
            180                 185                 190

Pro Glu Asp Ile Tyr Val Glu Trp Thr Asn Asn Gly Lys Thr Glu Leu
        195                 200                 205

Asn Tyr Lys Asn Thr Glu Pro Val Leu Asp Ser Asp Gly Ser Tyr Phe
    210                 215                 220

Met Tyr Ser Lys Leu Arg Val Glu Lys Lys Asn Trp Val Glu Arg Asn
225                 230                 235                 240

Ser Tyr Ser Cys Ser Val Val His Glu Gly Leu His Asn His His Thr
                245                 250                 255

Thr Lys Ser Phe Ser Arg Thr Pro Gly Lys Glu Arg Lys Cys Cys Val
            260                 265                 270

Glu Cys Pro Pro Cys Pro
        275
```

<210> SEQ ID NO 13
<211> LENGTH: 265
<212> TYPE: PRT
<213> ORGANISM: Mus sp.

<400> SEQUENCE: 13

```
Met Glu Thr Asp Thr Leu Leu Leu Trp Val Leu Leu Leu Trp Val Pro
1               5                   10                  15

Gly Ser Thr Gly Glu Arg Lys Cys Cys Val Glu Cys Pro Pro Cys Pro
            20                  25                  30
```

Glu Pro Arg Gly Pro Thr Ile Lys Pro Cys Pro Cys Lys Cys Pro
        35                  40                  45

Ala Pro Asn Leu Leu Gly Gly Pro Ser Val Phe Ile Phe Pro Pro Lys
 50                  55                  60

Ile Lys Asp Val Leu Met Ile Ser Leu Ser Pro Ile Val Thr Cys Val
 65                  70                  75                  80

Val Val Asp Val Ser Glu Asp Pro Asp Val Gln Ile Ser Trp Phe
                85                  90                  95

Val Asn Asn Val Glu Val His Thr Ala Gln Thr Gln Thr His Arg Glu
                100                 105                 110

Asp Tyr Asn Ser Thr Leu Arg Val Val Ser Ala Leu Pro Ile Gln His
        115                 120                 125

Gln Asp Trp Met Ser Gly Lys Glu Phe Lys Cys Lys Val Asn Asn Lys
    130                 135                 140

Asp Leu Pro Ala Pro Ile Glu Arg Thr Ile Ser Lys Pro Lys Gly Ser
145                 150                 155                 160

Val Arg Ala Pro Gln Val Tyr Val Leu Pro Pro Glu Glu Glu Met
                165                 170                 175

Thr Lys Lys Gln Val Thr Leu Thr Cys Met Val Thr Asp Phe Met Pro
            180                 185                 190

Glu Asp Ile Tyr Val Glu Trp Thr Asn Asn Gly Lys Thr Glu Leu Asn
        195                 200                 205

Tyr Lys Asn Thr Glu Pro Val Leu Asp Ser Asp Gly Ser Tyr Phe Met
    210                 215                 220

Tyr Ser Lys Leu Arg Val Glu Lys Lys Asn Trp Val Glu Arg Asn Ser
225                 230                 235                 240

Tyr Ser Cys Ser Val Val His Glu Gly Leu His Asn His His Thr Thr
                245                 250                 255

Lys Ser Phe Ser Arg Thr Pro Gly Lys
            260                 265

<210> SEQ ID NO 14
<211> LENGTH: 287
<212> TYPE: PRT
<213> ORGANISM: Mus sp.

<400> SEQUENCE: 14

Met Glu Thr Asp Thr Leu Leu Leu Trp Val Leu Leu Leu Trp Val Pro
1               5                   10                  15

Gly Ser Thr Gly Ser Ile Lys Gln Ile Glu Asp Lys Ile Glu Glu Ile
            20                  25                  30

Leu Ser Lys Ile Tyr His Ile Glu Asn Glu Ile Ala Arg Ile Lys Lys
        35                  40                  45

Leu Ile Gly Glu Arg Gly Glu Pro Arg Gly Pro Thr Ile Lys Pro Cys
 50                  55                  60

Pro Pro Cys Lys Cys Pro Ala Pro Asn Leu Leu Gly Gly Pro Ser Val
65                  70                  75                  80

Phe Ile Phe Pro Pro Lys Ile Lys Asp Val Leu Met Ile Ser Leu Ser
                85                  90                  95

Pro Ile Val Thr Cys Val Val Asp Val Ser Glu Asp Asp Pro Asp
                100                 105                 110

Val Gln Ile Ser Trp Phe Val Asn Asn Val Glu Val His Thr Ala Gln
        115                 120                 125

Thr Gln Thr His Arg Glu Asp Tyr Asn Ser Thr Leu Arg Val Val Ser

```
                130                 135                 140
Ala Leu Pro Ile Gln His Gln Asp Trp Met Ser Gly Lys Glu Phe Lys
145                 150                 155                 160

Cys Lys Val Asn Asn Lys Asp Leu Pro Ala Pro Ile Glu Arg Thr Ile
                165                 170                 175

Ser Lys Pro Lys Gly Ser Val Arg Ala Pro Gln Val Tyr Val Leu Pro
                180                 185                 190

Pro Pro Glu Glu Glu Met Thr Lys Lys Gln Val Thr Leu Thr Cys Met
                195                 200                 205

Val Thr Asp Phe Met Pro Glu Asp Ile Tyr Val Glu Trp Thr Asn Asn
210                 215                 220

Gly Lys Thr Glu Leu Asn Tyr Lys Asn Thr Glu Pro Val Leu Asp Ser
225                 230                 235                 240

Asp Gly Ser Tyr Phe Met Tyr Ser Lys Leu Arg Val Glu Lys Lys Asn
                245                 250                 255

Trp Val Glu Arg Asn Ser Tyr Ser Cys Ser Val Val His Glu Gly Leu
                260                 265                 270

His Asn His His Thr Thr Lys Ser Phe Ser Arg Thr Pro Gly Lys
                275                 280                 285

<210> SEQ ID NO 15
<211> LENGTH: 291
<212> TYPE: PRT
<213> ORGANISM: Mus sp.

<400> SEQUENCE: 15

Met Glu Thr Asp Thr Leu Leu Leu Trp Val Leu Leu Leu Trp Val Pro
1               5                   10                  15

Gly Ser Thr Gly Asp Glu Pro Arg Gly Pro Thr Ile Lys Pro Cys Pro
                20                  25                  30

Pro Cys Lys Cys Pro Ala Pro Asn Leu Leu Gly Gly Pro Ser Val Phe
            35                  40                  45

Ile Phe Pro Pro Lys Ile Lys Asp Val Leu Met Ile Ser Leu Ser Pro
50                  55                  60

Ile Val Thr Cys Val Val Val Asp Val Ser Glu Asp Asp Pro Asp Val
65                  70                  75                  80

Gln Ile Ser Trp Phe Val Asn Asn Val Glu Val His Thr Ala Gln Thr
                85                  90                  95

Gln Thr His Arg Glu Asp Tyr Asn Ser Thr Leu Arg Val Val Ser Ala
                100                 105                 110

Leu Pro Ile Gln His Gln Asp Trp Met Ser Gly Lys Glu Phe Lys Cys
                115                 120                 125

Lys Val Asn Asn Lys Asp Leu Pro Ala Pro Ile Glu Arg Thr Ile Ser
130                 135                 140

Lys Pro Lys Gly Ser Val Arg Ala Pro Gln Val Tyr Val Leu Pro Pro
145                 150                 155                 160

Pro Glu Glu Glu Met Thr Lys Lys Gln Val Thr Leu Thr Cys Met Val
                165                 170                 175

Thr Asp Phe Met Pro Glu Asp Ile Tyr Val Glu Trp Thr Asn Asn Gly
                180                 185                 190

Lys Thr Glu Leu Asn Tyr Lys Asn Thr Glu Pro Val Leu Asp Ser Asp
                195                 200                 205

Gly Ser Tyr Phe Met Tyr Ser Lys Leu Arg Val Glu Lys Lys Asn Trp
                210                 215                 220
```

```
Val Glu Arg Asn Ser Tyr Ser Cys Ser Val Val His Glu Gly Leu His
225                 230                 235                 240

Asn His His Thr Thr Lys Ser Phe Ser Arg Thr Pro Gly Lys Gly Gly
                245                 250                 255

Gly Ser Ile Lys Gln Ile Glu Asp Lys Ile Glu Glu Ile Leu Ser Lys
            260                 265                 270

Ile Tyr His Ile Glu Asn Glu Ile Ala Arg Ile Lys Lys Leu Ile Gly
        275                 280                 285

Glu Arg Gly
    290

<210> SEQ ID NO 16
<211> LENGTH: 299
<212> TYPE: PRT
<213> ORGANISM: Mus sp.

<400> SEQUENCE: 16

Met Glu Thr Asp Thr Leu Leu Leu Trp Val Leu Leu Leu Trp Val Pro
1               5                   10                  15

Gly Ser Thr Gly Asp Ala Ala Asp Ile Gln His Ser Gly Gly Arg Ser
            20                  25                  30

Ser Ile Lys Gln Ile Glu Asp Lys Ile Glu Glu Ile Leu Ser Lys Ile
        35                  40                  45

Tyr His Ile Glu Asn Glu Ile Ala Arg Ile Lys Lys Leu Ile Gly Glu
    50                  55                  60

Arg Gly Glu Pro Arg Gly Pro Thr Ile Lys Pro Cys Pro Pro Cys Lys
65                  70                  75                  80

Cys Pro Ala Pro Asn Leu Leu Gly Gly Pro Ser Val Phe Ile Phe Pro
                85                  90                  95

Pro Lys Ile Lys Asp Val Leu Met Ile Ser Leu Ser Pro Ile Val Thr
            100                 105                 110

Cys Val Val Val Asp Val Ser Glu Asp Asp Pro Asp Val Gln Ile Ser
        115                 120                 125

Trp Phe Val Asn Asn Val Glu Val His Thr Ala Gln Thr Gln Thr His
    130                 135                 140

Arg Glu Asp Tyr Asn Ser Thr Leu Arg Val Val Ser Ala Leu Pro Ile
145                 150                 155                 160

Gln His Gln Asp Trp Met Ser Gly Lys Glu Phe Lys Cys Lys Val Asn
                165                 170                 175

Asn Lys Asp Leu Pro Ala Pro Ile Glu Arg Thr Ile Ser Lys Pro Lys
            180                 185                 190

Gly Ser Val Arg Ala Pro Gln Val Tyr Val Leu Pro Pro Pro Glu Glu
        195                 200                 205

Glu Met Thr Lys Lys Gln Val Thr Leu Thr Cys Met Val Thr Asp Phe
    210                 215                 220

Met Pro Glu Asp Ile Tyr Val Glu Trp Thr Asn Asn Gly Lys Thr Glu
225                 230                 235                 240

Leu Asn Tyr Lys Asn Thr Glu Pro Val Leu Asp Ser Asp Gly Ser Tyr
                245                 250                 255

Phe Met Tyr Ser Lys Leu Arg Val Glu Lys Lys Asn Trp Val Glu Arg
            260                 265                 270

Asn Ser Tyr Ser Cys Ser Val Val His Glu Gly Leu His Asn His His
        275                 280                 285

Thr Thr Lys Ser Phe Ser Arg Thr Pro Gly Lys
    290                 295
```

<210> SEQ ID NO 17
<211> LENGTH: 753
<212> TYPE: DNA
<213> ORGANISM: Homo sapiens

<400> SEQUENCE: 17

```
atggagacag acacactcct gctatgggta ctgctgctct gggttccagg ttccactggt    60
gagcgcaaat gttgtgtgga gtgcccaccg tgcccagcac ctgaactcct ggggggaccg   120
tcagtcttcc tcttcccccc aaaacccaag gacaccctca tgatctcccg acccctgag   180
gtcacatgcg tggtggtgga cgtgagccac gaagaccctg aggtcaagtt caactggtac   240
gtggacggcg tggaggtgca taatgccaag acaaagccgc gggaggagca gtacaacagc   300
acgtaccgtg tggtcagcgt cctcaccgtc ctgcaccagg actggctgaa tggcaaggag   360
tacaagtgca aggtctccaa caaagccctc ccagccccca tcgagaaaac catctccaaa   420
gccaaagggc agccccgaga accacaggtg tacaccctgc ccccatcccg ggaggagatg   480
accaagaacc aggtcagcct gacctgcctg gtcaaaggct tctatcccag cgacatcgcc   540
gtggagtggg agagcaatgg gcagccggag aacaactaca agaccacgcc tcccgtgctg   600
gactccgacg gctccttctt cctctatagc aagctcaccg tggacaagag caggtggcag   660
caggggaacg tcttctcatg ctccgtgatg catgaggctc tgcacaacca ctacacgcag   720
aagagcctct ccctgtcccc gggtaaatga taa                                753
```

<210> SEQ ID NO 18
<211> LENGTH: 249
<212> TYPE: PRT
<213> ORGANISM: Homo sapiens

<400> SEQUENCE: 18

Met Glu Thr Asp Thr Leu Leu Leu Trp Val Leu Leu Leu Trp Val Pro
1               5                   10                  15

Gly Ser Thr Gly Glu Arg Lys Cys Cys Val Glu Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
        50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Glu Glu Met
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

```
Tyr Lys Thr Thr Pro Pro Val Leu Asp Ser Asp Gly Ser Phe Phe Leu
            195                 200                 205

Tyr Ser Lys Leu Thr Val Asp Lys Ser Arg Trp Gln Gln Gly Asn Val
        210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245
```

<210> SEQ ID NO 19
<211> LENGTH: 217
<212> TYPE: PRT
<213> ORGANISM: Homo sapiens

<400> SEQUENCE: 19

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 20
<211> LENGTH: 264
<212> TYPE: PRT
<213> ORGANISM: Homo sapiens

<400> SEQUENCE: 20

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45
```

```
Pro Pro Lys Pro Lys Asp Thr Leu Met Ile Ser Arg Thr Pro Glu Val
    50                  55                  60
Thr Cys Val Val Val Asp Val Ser His Glu Asp Pro Glu Val Lys Phe
65                  70                  75                  80
Asn Trp Tyr Val Asp Gly Val Glu Val His Asn Ala Lys Thr Lys Pro
                85                  90                  95
Arg Glu Glu Gln Tyr Asn Ala Thr Tyr Arg Val Val Ser Val Leu Thr
            100                 105                 110
Val Leu His Gln Asp Trp Leu Asn Gly Lys Glu Tyr Lys Cys Lys Val
        115                 120                 125
Ser Asn Lys Ala Leu Pro Ala Pro Ile Glu Lys Thr Ile Ser Lys Ala
130                 135                 140
Lys Gly Gln Pro Arg Glu Pro Gln Val Tyr Thr Leu Pro Pro Ser Arg
145                 150                 155                 160
Glu Glu Met Thr Lys Asn Gln Val Ser Leu Thr Cys Leu Val Lys Gly
                165                 170                 175
Phe Tyr Pro Ser Asp Ile Ala Val Glu Trp Glu Ser Asn Gly Gln Pro
            180                 185                 190
Glu Asn Asn Tyr Lys Thr Thr Pro Pro Val Leu Asp Ser Asp Gly Ser
        195                 200                 205
Phe Phe Leu Tyr Ser Lys Leu Thr Val Asp Lys Ser Arg Trp Gln Gln
210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys Glu Arg Lys Cys
                245                 250                 255
Cys Val Glu Cys Pro Pro Cys Pro
            260

<210> SEQ ID NO 21
<211> LENGTH: 264
<212> TYPE: PRT
<213> ORGANISM: Homo sapiens

<400> SEQUENCE: 21

Met Glu Thr Asp Thr Leu Leu Leu Trp Val Leu Leu Trp Val Pro
1               5                   10                  15
Gly Ser Thr Gly Glu Pro Lys Ser Cys Asp Lys Thr His Thr Cys Pro
            20                  25                  30
Pro Cys Pro Ala Pro Glu Leu Leu Gly Gly Pro Ser Val Phe Leu Phe
        35                  40                  45
Pro Pro Lys Pro Lys Asp Thr Leu Met Ile Ser Arg Thr Pro Glu Val
    50                  55                  60
Thr Cys Val Val Val Asp Val Ser His Glu Asp Pro Glu Val Lys Phe
65                  70                  75                  80
Asn Trp Tyr Val Asp Gly Val Glu Val His Asn Ala Lys Thr Lys Pro
                85                  90                  95
Arg Glu Glu Gln Tyr Asn Ser Thr Tyr Ala Val Val Ser Val Leu Thr
            100                 105                 110
Val Leu His Gln Asp Trp Leu Asn Gly Lys Glu Tyr Lys Cys Lys Val
        115                 120                 125
Ser Asn Lys Ala Leu Pro Ala Pro Ile Glu Lys Thr Ile Ser Lys Ala
130                 135                 140
Lys Gly Gln Pro Arg Glu Pro Gln Val Tyr Thr Leu Pro Pro Ser Arg
145                 150                 155                 160
```

```
Glu Glu Met Thr Lys Asn Gln Val Ser Leu Thr Cys Leu Val Lys Gly
            165                 170                 175

Phe Tyr Pro Ser Asp Ile Ala Val Glu Trp Glu Ser Asn Gly Gln Pro
        180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 22
<211> LENGTH: 266
<212> TYPE: PRT
<213> ORGANISM: Mus sp.

<400> SEQUENCE: 22

Met Glu Thr Asp Thr Leu Leu Leu Trp Val Leu Leu Leu Trp Val Pro
1               5                   10                  15

Gly Ser Thr Gly Asp Glu Pro Arg Gly Pro Thr Ile Lys Pro Cys Pro
            20                  25                  30

Pro Cys Lys Cys Pro Ala Pro Asn Leu Leu Gly Gly Pro Ser Val Phe
        35                  40                  45

Ile Phe Pro Pro Lys Ile Lys Asp Val Leu Met Ile Ser Leu Ser Pro
    50                  55                  60

Ile Val Thr Cys Val Val Val Asp Val Ser Glu Asp Asp Pro Asp Val
65                  70                  75                  80

Gln Ile Ser Trp Phe Val Asn Asn Val Glu Val His Thr Ala Gln Thr
                85                  90                  95

Gln Thr His Arg Glu Asp Tyr Asn Ala Thr Leu Arg Val Val Ser Ala
            100                 105                 110

Leu Pro Ile Gln His Gln Asp Trp Met Ser Gly Lys Glu Phe Lys Cys
        115                 120                 125

Lys Val Asn Asn Lys Asp Leu Pro Ala Pro Ile Glu Arg Thr Ile Ser
    130                 135                 140

Lys Pro Lys Gly Ser Val Arg Ala Pro Gln Val Tyr Val Leu Pro Pro
145                 150                 155                 160

Pro Glu Glu Glu Met Thr Lys Lys Gln Val Thr Leu Thr Cys Met Val
                165                 170                 175

Thr Asp Phe Met Pro Glu Asp Ile Tyr Val Glu Trp Thr Asn Asn Gly
            180                 185                 190

Lys Thr Glu Leu Asn Tyr Lys Asn Thr Glu Pro Val Leu Asp Ser Asp
        195                 200                 205

Gly Ser Tyr Phe Met Tyr Ser Lys Leu Arg Val Glu Lys Lys Asn Trp
    210                 215                 220

Val Glu Arg Asn Ser Tyr Ser Cys Ser Val Val His Glu Gly Leu His
225                 230                 235                 240

Asn His His Thr Thr Lys Ser Phe Ser Arg Thr Pro Gly Lys Glu Arg
                245                 250                 255

Lys Cys Cys Val Glu Cys Pro Pro Cys Pro
```

```
<210> SEQ ID NO 23
<211> LENGTH: 266
<212> TYPE: PRT
<213> ORGANISM: Mus sp.

<400> SEQUENCE: 23
```

Met Glu Thr Asp Thr Leu Leu Leu Trp Val Leu Leu Leu Trp Val Pro
1               5                   10                  15

Gly Ser Thr Gly Asp Glu Pro Arg Gly Pro Thr Ile Lys Pro Cys Pro
            20                  25                  30

Pro Cys Lys Cys Pro Ala Pro Asn Leu Leu Gly Gly Pro Ser Val Phe
        35                  40                  45

Ile Phe Pro Pro Lys Ile Lys Asp Val Leu Met Ile Ser Leu Ser Pro
50                  55                  60

Ile Val Thr Cys Val Val Val Asp Val Ser Glu Asp Asp Pro Asp Val
65                  70                  75                  80

Gln Ile Ser Trp Phe Val Asn Asn Val Glu Val His Thr Ala Gln Thr
                85                  90                  95

Gln Thr His Arg Glu Asp Tyr Asn Ser Thr Leu Ala Val Val Ser Ala
            100                 105                 110

Leu Pro Ile Gln His Gln Asp Trp Met Ser Gly Lys Glu Phe Lys Cys
        115                 120                 125

Lys Val Asn Asn Lys Asp Leu Pro Ala Pro Ile Glu Arg Thr Ile Ser
130                 135                 140

Lys Pro Lys Gly Ser Val Arg Ala Pro Gln Val Tyr Val Leu Pro Pro
145                 150                 155                 160

Pro Glu Glu Glu Met Thr Lys Lys Gln Val Thr Leu Thr Cys Met Val
                165                 170                 175

Thr Asp Phe Met Pro Glu Asp Ile Tyr Val Glu Trp Thr Asn Asn Gly
            180                 185                 190

Lys Thr Glu Leu Asn Tyr Lys Asn Thr Glu Pro Val Leu Asp Ser Asp
        195                 200                 205

Gly Ser Tyr Phe Met Tyr Ser Lys Leu Arg Val Glu Lys Lys Asn Trp
    210                 215                 220

Val Glu Arg Asn Ser Tyr Ser Cys Ser Val Val His Glu Gly Leu His
225                 230                 235                 240

Asn His His Thr Thr Lys Ser Phe Ser Arg Thr Pro Gly Lys Glu Arg
                245                 250                 255

Lys Cys Cys Val Glu Cys Pro Cys Pro
            260                 265

```
<210> SEQ ID NO 24
<211> LENGTH: 282
<212> TYPE: PRT
<213> ORGANISM: Homo sapiens

<400> SEQUENCE: 24
```

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ala Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Gly Pro Pro Gly
                245                 250                 255

Pro Pro Gly Pro Pro Gly Pro Pro Gly Pro Pro Gly Pro Pro Gly Pro
            260                 265                 270

Pro Gly Pro Pro Gly Pro Gly Pro Pro
        275                 280

<210> SEQ ID NO 25
<211> LENGTH: 284
<212> TYPE: PRT
<213> ORGANISM: Mus sp.

<400> SEQUENCE: 25

Met Glu Thr Asp Thr Leu Leu Leu Trp Val Leu Leu Leu Trp Val Pro
1               5                   10                  15

Gly Ser Thr Gly Asp Glu Pro Arg Gly Pro Thr Ile Lys Pro Cys Pro
            20                  25                  30

Pro Cys Lys Cys Pro Ala Pro Asn Leu Leu Gly Gly Pro Ser Val Phe
        35                  40                  45

Ile Phe Pro Pro Lys Ile Lys Asp Val Leu Met Ile Ser Leu Ser Pro
    50                  55                  60

Ile Val Thr Cys Val Val Val Asp Val Ser Glu Asp Asp Pro Asp Val
65                  70                  75                  80

Gln Ile Ser Trp Phe Val Asn Asn Val Glu Val His Thr Ala Gln Thr
                85                  90                  95

Gln Thr His Arg Glu Asp Tyr Asn Ala Thr Leu Arg Val Val Ser Ala
            100                 105                 110

Leu Pro Ile Gln His Gln Asp Trp Met Ser Gly Lys Glu Phe Lys Cys
        115                 120                 125

Lys Val Asn Asn Lys Asp Leu Pro Ala Pro Ile Glu Arg Thr Ile Ser
    130                 135                 140

```
Lys Pro Lys Gly Ser Val Arg Ala Pro Gln Val Tyr Val Leu Pro Pro
145                 150                 155                 160

Pro Glu Glu Met Thr Lys Lys Gln Val Thr Leu Thr Cys Met Val
                165                 170                 175

Thr Asp Phe Met Pro Glu Asp Ile Tyr Val Glu Trp Thr Asn Asn Gly
            180                 185                 190

Lys Thr Glu Leu Asn Tyr Lys Asn Thr Glu Pro Val Leu Asp Ser Asp
        195                 200                 205

Gly Ser Tyr Phe Met Tyr Ser Lys Leu Arg Val Glu Lys Lys Asn Trp
    210                 215                 220

Val Glu Arg Asn Ser Tyr Ser Cys Ser Val Val His Glu Gly Leu His
225                 230                 235                 240

Asn His His Thr Thr Lys Ser Phe Ser Arg Thr Pro Gly Lys Gly Pro
                245                 250                 255

Pro Gly Pro Pro Gly Pro Pro Gly Pro Pro Gly Pro Pro Gly Pro Pro
            260                 265                 270

Gly Pro Pro Gly Pro Pro Gly Pro Pro Gly Pro Pro
        275                 280
```

<210> SEQ ID NO 26
<211> LENGTH: 30
<212> TYPE: PRT
<213> ORGANISM: Artificial Sequence
<220> FEATURE:
<223> OTHER INFORMATION: GPP multimerization domain

<400> SEQUENCE: 26

```
Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro
            20                  25                  30
```

<210> SEQ ID NO 27
<211> LENGTH: 282
<212> TYPE: PRT
<213> ORGANISM: Homo sapiens

<400> SEQUENCE: 27

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
                20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
```

```
                145                 150                 155                 160
        Glu Glu Met Thr Lys Asn Gln Val Ser Leu Thr Cys Leu Val Lys Gly
                        165                 170                 175

Phe Tyr Pro Ser Asp Ile Ala Val Glu Trp Glu Ser Asn Gly Gln Pro
                        180                 185                 190

Glu Asn Asn Tyr Lys Thr Thr Pro Val Leu Asp Ser Asp Gly Ser
                        195                 200                 205

Phe Phe Leu Tyr Ser Lys Leu Thr Val Asp Lys Ser Arg Trp Gln Gln
                        210                 215                 220

Gly Asn Val Phe Ser Cys Ser Val Met His Glu Ala Leu His Asn His
        225                 230                 235                 240

Tyr Thr Gln Lys Ser Leu Ser Leu Ser Pro Gly Lys Gly Pro Pro Gly
                        245                 250                 255

Pro Pro Gly Pro Gly Pro Gly Pro Pro Gly Pro Gly Pro
                        260                 265                 270

Pro Gly Pro Pro Gly Pro Pro Gly Pro Pro
                        275                 280

<210> SEQ ID NO 28
<211> LENGTH: 282
<212> TYPE: PRT
<213> ORGANISM: Homo sapiens

<400> SEQUENCE: 28

Met Glu Thr Asp Thr Leu Leu Leu Trp Val Leu Leu Leu Trp Val Pro
        1               5                   10                  15

Gly Ser Thr Gly Gly Pro Pro Gly Pro Gly Pro Pro Gly Pro Gly Pro Pro
                        20                  25                  30

Gly Pro Pro Gly Pro Pro Gly Pro Gly Pro Pro Gly Pro Pro Gly
                        35                  40                  45

Pro Pro Glu Pro Lys Ser Cys Asp Lys Thr His Thr Cys Pro Pro Cys
                        50                  55                  60

Pro Ala Pro Glu Leu Leu Gly Gly Pro Ser Val Phe Leu Phe Pro Pro
        65                  70                  75                  80

Lys Pro Lys Asp Thr Leu Met Ile Ser Arg Thr Pro Glu Val Thr Cys
                        85                  90                  95

Val Val Val Asp Val Ser His Glu Asp Pro Glu Val Lys Phe Asn Trp
                        100                 105                 110

Tyr Val Asp Gly Val Glu Val His Asn Ala Lys Thr Lys Pro Arg Glu
                        115                 120                 125

Glu Gln Tyr Asn Ser Thr Tyr Arg Val Val Ser Val Leu Thr Val Leu
                        130                 135                 140

His Gln Asp Trp Leu Asn Gly Lys Glu Tyr Lys Cys Lys Val Ser Asn
        145                 150                 155                 160

Lys Ala Leu Pro Ala Pro Ile Glu Lys Thr Ile Ser Lys Ala Lys Gly
                        165                 170                 175

Gln Pro Arg Glu Pro Gln Val Tyr Thr Leu Pro Pro Ser Arg Glu Glu
                        180                 185                 190

Met Thr Lys Asn Gln Val Ser Leu Thr Cys Leu Val Lys Gly Phe Tyr
                        195                 200                 205

Pro Ser Asp Ile Ala Val Glu Trp Glu Ser Asn Gly Gln Pro Glu Asn
                        210                 215                 220

Asn Tyr Lys Thr Thr Pro Pro Val Leu Asp Ser Asp Gly Ser Phe Phe
        225                 230                 235                 240
```

Leu Tyr Ser Lys Leu Thr Val Asp Lys Ser Arg Trp Gln Gln Gly Asn
            245                 250                 255

Val Phe Ser Cys Ser Val Met His Glu Ala Leu His Asn His Tyr Thr
        260                 265                 270

Gln Lys Ser Leu Ser Leu Ser Pro Gly Lys
    275                 280

<210> SEQ ID NO 29
<211> LENGTH: 284
<212> TYPE: PRT
<213> ORGANISM: Mus sp.

<400> SEQUENCE: 29

Met Glu Thr Asp Thr Leu Leu Leu Trp Val Leu Leu Leu Trp Val Pro
1               5                   10                  15

Gly Ser Thr Gly Asp Glu Pro Arg Gly Pro Thr Ile Lys Pro Cys Pro
            20                  25                  30

Pro Cys Lys Cys Pro Ala Pro Asn Leu Leu Gly Gly Pro Ser Val Phe
        35                  40                  45

Ile Phe Pro Pro Lys Ile Lys Asp Val Leu Met Ile Ser Leu Ser Pro
    50                  55                  60

Ile Val Thr Cys Val Val Val Asp Val Ser Glu Asp Asp Pro Asp Val
65                  70                  75                  80

Gln Ile Ser Trp Phe Val Asn Asn Val Glu Val His Thr Ala Gln Thr
                85                  90                  95

Gln Thr His Arg Glu Asp Tyr Asn Ser Thr Leu Arg Val Val Ser Ala
            100                 105                 110

Leu Pro Ile Gln His Gln Asp Trp Met Ser Gly Lys Glu Phe Lys Cys
        115                 120                 125

Lys Val Asn Asn Lys Asp Leu Pro Ala Pro Ile Glu Arg Thr Ile Ser
    130                 135                 140

Lys Pro Lys Gly Ser Val Arg Ala Pro Gln Val Tyr Val Leu Pro Pro
145                 150                 155                 160

Pro Glu Glu Glu Met Thr Lys Lys Gln Val Thr Leu Thr Cys Met Val
                165                 170                 175

Thr Asp Phe Met Pro Glu Asp Ile Tyr Val Glu Trp Thr Asn Asn Gly
            180                 185                 190

Lys Thr Glu Leu Asn Tyr Lys Asn Thr Glu Pro Val Leu Asp Ser Asp
        195                 200                 205

Gly Ser Tyr Phe Met Tyr Ser Lys Leu Arg Val Glu Lys Lys Asn Trp
    210                 215                 220

Val Glu Arg Asn Ser Tyr Ser Cys Ser Val Val His Glu Gly Leu His
225                 230                 235                 240

Asn His His Thr Thr Lys Ser Phe Ser Arg Thr Pro Gly Lys Gly Pro
                245                 250                 255

Pro Gly Pro Pro Gly Pro Pro Gly Pro Pro Gly Pro Pro Gly Pro Pro
            260                 265                 270

Gly Pro Pro Gly Pro Pro Gly Pro Pro Gly Pro Pro
        275                 280

<210> SEQ ID NO 30
<211> LENGTH: 283
<212> TYPE: PRT
<213> ORGANISM: Mus sp.

<400> SEQUENCE: 30

-continued

```
Met Glu Thr Asp Thr Leu Leu Leu Trp Val Leu Leu Leu Trp Val Pro
1               5                   10                  15

Gly Ser Thr Gly Gly Pro Pro Gly Pro Pro Gly Pro Pro Gly Pro Pro
            20                  25                  30

Gly Pro Pro Gly Pro Pro Gly Pro Pro Gly Pro Pro Gly Pro Pro Gly
        35                  40                  45

Pro Pro Glu Pro Arg Gly Pro Thr Ile Lys Pro Cys Pro Pro Cys Lys
    50                  55                  60

Cys Pro Ala Pro Asn Leu Leu Gly Gly Pro Ser Val Phe Ile Phe Pro
65                  70                  75                  80

Pro Lys Ile Lys Asp Val Leu Met Ile Ser Leu Ser Pro Ile Val Thr
                85                  90                  95

Cys Val Val Val Asp Val Ser Glu Asp Asp Pro Asp Val Gln Ile Ser
            100                 105                 110

Trp Phe Val Asn Asn Val Glu Val His Thr Ala Gln Thr Gln Thr His
        115                 120                 125

Arg Glu Asp Tyr Asn Ser Thr Leu Arg Val Val Ser Ala Leu Pro Ile
        130                 135                 140

Gln His Gln Asp Trp Met Ser Gly Lys Glu Phe Lys Cys Lys Val Asn
145                 150                 155                 160

Asn Lys Asp Leu Pro Ala Pro Ile Glu Arg Thr Ile Ser Lys Pro Lys
                165                 170                 175

Gly Ser Val Arg Ala Pro Gln Val Tyr Val Leu Pro Pro Pro Glu Glu
            180                 185                 190

Glu Met Thr Lys Lys Gln Val Thr Leu Thr Cys Met Val Thr Asp Phe
        195                 200                 205

Met Pro Glu Asp Ile Tyr Val Glu Trp Thr Asn Asn Gly Lys Thr Glu
    210                 215                 220

Leu Asn Tyr Lys Asn Thr Glu Pro Val Leu Asp Ser Asp Gly Ser Tyr
225                 230                 235                 240

Phe Met Tyr Ser Lys Leu Arg Val Glu Lys Lys Asn Trp Val Glu Arg
                245                 250                 255

Asn Ser Tyr Ser Cys Ser Val Val His Glu Gly Leu His Asn His His
            260                 265                 270

Thr Thr Lys Ser Phe Ser Arg Thr Pro Gly Lys
        275                 280
```

FUSION PROTEINS OF NATURAL HUMAN PROTEIN FRAGMENTS TO CREATE ORDERLY MULTIMERIZED IMMUNOGLOBULIN Fc COMPOSITIONS

CROSS REFERENCE TO RELATED APPLICATIONS

This application is a divisional application of U.S. patent application Ser. No. 15/642,175, filed Jul. 5, 2017, which is a divisional of U.S. patent application Ser. No. 13/812,269, filed Mar. 6, 2013 (abandoned), which claims priority under 35 U.S.C. § 371 to, and is a U.S. National Phase Application of, International PCT Application No. PCT/US2011/045768, filed Jul. 28, 2011, which claims the benefit of priority to U.S. Provisional Patent Application No. 61/368,465, filed Jul. 28, 2010, the contents of which are incorporated by reference herein in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GLIK_006_04US_SeqList_ST25.txt, date recorded: Mar. 30, 2020, file size 61 kilobytes).

FIELD OF THE INVENTION

This invention relates generally to the fields of immunology, autoimmunity, inflammation, and tumor immunology. More specifically, the present invention relates to biologically active biomimetic molecules comprising naturally linked immunoglobulin Fc domains, compositions comprising such biomimetics, and methods of making and using such biomimetics.

The invention also relates to the treatment and prophylaxis of pathological conditions mediated by lymphocytes, NK cells, monocyte-derived cells and immune cells that interact with monocyte-derived cells, and more particularly to the use of stabilized functional portions of linked IgG Fc fragments for such treatment and prophylaxis.

Immunoglobulin products from human plasma have been used since the early 1950's to treat immune deficiency disorders and more recently, and more commonly, for autoimmune and inflammatory diseases.

Initially, immune globulin products were administered by intramuscular injection. More recently, intravenous immune globulin (IVIG) has been used and was initially shown to be effective in treatment of the autoimmune disease idiopathic thrombocytopenia purpura (ITP) (Imbach P, Barandun S, d'Apuzzo V, et al: High-dose intravenous gammaglobulin for idiopathic thrombocytopenia purpura in childhood. Lancet 1981 Jun. 6; 1(8232): 1228-31). Human IVIG (referred to herein as "hIVIG") is a formulation of sterile, purified immunoglobulin G (IgG) products manufactured from pooled human plasma that typically contains more than 95% unmodified IgG, with only small and variable amounts of immunoglobulin A (IgA) or immunoglobulin M (IgM) (see, for example, Rutter A, Luger T A: High-dose intravenous immunoglobulins: an approach to treat severe immune-mediated and autoimmune diseases of the skin. J Am Acad Dermatol 2001 Jun; 44(6): 1010-24). Today the single most common clinical use of hIVIG is in the treatment of Chronic Inflammatory Demyelinating Polyneuropathy.

While hIVIG has been an effective clinical treatment, there are several shortcomings to hIVIG treatments, including the potential for inadequate sterility, the presence of impurities or infectious agents including viruses and prions, lack of availability of this pooled human blood product, lot-to-lot variation, high expense, large protein load affecting renal function, and long administration time, generally over many hours and sometimes two consecutive days monthly. In particular hIVIG preparations can vary greatly in their immunoglobulin A (IgA) content which can be of concern because IgA can cause allergic and anaphylactic reactions in IgA-deficient recipients. In view of the negative aspects of hIVIG, there exists a need for an improved means of treating autoimmune and inflammatory diseases and in particular a need for a plentiful source of recombinantly produced product with at least that equivalent efficacy, greater potency, shorter administration time and greater purity.

In addition, multiple pathological conditions of a wide variety of types are mediated by cells derived from monocytes, lymphocytes and NK cells. A novel therapeutic and/or prophylactic agent for use in many, if not all, such conditions would fulfill an important unmet medical need and be commercially valuable.

Many of the immuno-regulatory properties of hIVIG reside in the Fc domain of IgG molecules. For example, in murine models of ITP, both unmodified hIVIG and the Fc fragment alone demonstrate therapeutic efficacy in restoring platelet counts, while isolated hIVIG Fab fragments are not therapeutic (Samuelsson, A., Towers, T. L. & Ravetch, J. V. Anti-inflammatory Activity of hIVIG Mediated Through the Inhibitory Fc Receptor. Science 291, 484-486 (2001)). Moreover Fc, but not Fab fragments of hIVIG, is also therapeutically effective in the treatment of both childhood and adult idiopathic thrombocytopeniaurpura (Follea, G. et al. Intravenous plasmin-treated gamma globulin therapy in idiopathic thrombocytopenia purpura. Nouv Rev Fr Hematol 27, 5-10 (1985); Solal-Celigny, P., Bernard, J., Herrera, A. & Biovin, P. Treatment of adult autoimmune thrombocytopeniaurpura with high-dose intravenous plasmin-cleaved gammaglobulins. Scand J Haematol 31, 39-44 (1983); Debre, M. & Bonnet, M.- C. Infusion of Fc gamma fragments for treatment of children with acute immune thrombocytopeni purpura. Lancet 342, 945-49 (1993); Burdach, S. E., Evers, K. & Geurson, R. Treatment of acute idiopathic thrombocytopenia purpura of childhood with intravenous immunoglobulin G: Comparative efficacy of 7S and 5S preparations. J Pediatr 109, 770-775 (1986)).

Besides the family of classical Fc gamma-receptors, which can be distinguished into activating and inhibitory members, the neonatal Fc-receptor (FcRn), which belongs to the family of major histocompatibility class I (MHC-I) molecules and SignR1/DC-SIGN, which belong to the family of C-type lectins, can bind to the IgG Fc-fragment (Nimmerjahn and Ravetch, Antibody-mediated modulation of immune responses, Immunological Reviews, 236: 265-275 (2010). Additionally, there are Fc gamma receptor-like receptors to which immunoglobulin Fc molecules and bind and exert physiological effect (Davis R S. "Fc Receptor-like molecules" Annu. Rev. Immunol. 2007. 25:525-60). The therapeutic effect of hIVIG is initially mediated through the Fc gamma receptor (FcγR) and relies on Dendritic Cell (DC)-macrophage cross-talk for its long term tolerogenic effects. FcγRIIIa plays a requisite role in the initiator phase and FcγRIIb is required for the effector phase in murine models of ITP (Samuelsson, A., Towers, T. L. & Ravetch, J. V. Anti-inflammatory Activity of hIVIG Mediated Through the Inhibitory Fc Receptor. Science 291, 484-486 (2001); Siragam, V. et al. Intravenous immunoglobulin ameliorates ITP via activating Fcγ receptors on dendritic cells. Nat Med 12, 688 (2006)). Similarly, human studies demonstrate that anti-Fcγ receptor antibodies are effective in the treatment of refractory ITP (Clarkson, S. et al. Treatment of refractory immune thrombocytopenia purpura with an anti-Fc gamma-receptor antibody. N Engl J Med 314, 1236-1239 (1986)). Importantly, long term tolerogenic effects are mediated by cell-cell interactions, as adoptive transfer of hIVIG-treated DCs is effective in treating murine models of ITP (Siragam, V. et al. Intravenous immunoglobulin ameliorates ITP via activating Fcγ receptors on dendritic cells. Nat Med 12, 688 (2006)).

The immunomodulatory effects of hIVIG require aggregation of the FcγR. Aggregation of FcγR is mediated by IgG "dimers" present in hIVIG (5-15% of the total hIVIG) (Bleeker, W. K. et al. Vasoactive side effects of intravenous immunoglobulin preparations in a rat model and their treatment with recombinant platelet-activating factor acetylhydrolase. Blood 95, 1856-1861 (2000)). For example, the known immunocirculatory clinical hypotensive effects of IVIG correlates with the presence of "dimers" in IVIG (Kroez M et. al. Hypotension with Intravenous Immunoglobulin Therapy: importance of pH and dimer formation. Biologicals 31 (2003) 277-286.) For example, in a murine model of ITP, treatment with hIVIG with a high content of "dimers" (dimers of whole homodimeric immunoglobulin molecules) enhanced platelet counts while hIVIG "monomers" (whole homodimeric immunoglobulin molecules) were not effective (Teeling, J. L. et al. Therapeutic efficacy of intravenous immunoglobulin preparations depends on the immunoglobulin G dimers: studies in experimental immune thrombocytopenia. Blood 98, 1095-1099 (2001)). Furthermore, despite the fact that ion exchange resin and polyethylene glycol fractionation are routinely used in the manufacture of hIVIG to remove IgG aggregates, the clinical efficacy of hIVIG correlates with the presence of aggregates in the patient's sera (Augener, W., Friedman, B. & Brittinger, G. Are aggregates of IgG the effective part of high-dose immunoglobulin therapy in adult idiopathic thrombocytopeni purpura (ITP)? Blut 50, 249-252 (1985)). Importantly, the percentage of dimers also correlates with vasoactive side effects, which are treatable with acetylhydrolase (Bleeker, W. K. et al. Vasoactive side effects of intravenous immunoglobulin preparations in a rat model and their treatment with recombinant platelet-activating factor acetylhydrolase. Blood 95, 1856-1861 (2000)).

SUMMARY OF THE INVENTION

There is a need for an alternative to IVIG that solves the problems of high protein load, inconvenient patient dosing, infectious risk, IgA anaphylaxis, and limited availability while maintaining and enhancing the efficacy of the aggregate fraction of IVIG. The present invention relates to biologically active fusion protein biomimetic molecules comprising human immunoglobulin Fc and a single naturally occurring multimerization domain, compositions comprising the same, and methods of using the same. These biomimetics have broad application for treating immunological and inflammatory disorders including but not limited to autoimmune diseases, just like hIVIG after which these biomimetics were modeled. Further, certain of these biomimetics also have utility as laboratory reagents, such as for use in immunological assays for testing immune cell function, in the diagnosis of disease and in blocking non-specific binding of Fc in antibody-based immunoassays. Moreover, the biomimetics and compositions of the present invention have the advantage of overcoming the above-listed limitations of hIVIG as well as the multimerization limitations of the precursor biomimetic stradomers.

WO 2008/151088 discloses using linked immunoglobulin Fc domains to create orderly multimerized immunoglobulin Fc biomimetics of hIVIG (biologically active ordered multimers known as stradomers) for the treatment of pathological conditions including autoimmune diseases and other inflammatory conditions. See WO 2008/151088, incorporated by reference in its entirety. The disclosed molecules were designed to contain extraneous, relative to native immunoglobulin Fc, sequences including restriction sites and affinity tags in the immunoglobulin Fc monomer. These extraneous sequences accounted in total for a small fraction of the overall amino acid composition of the stradomer (approximately 16 total amino acids) and were placed between domains with separable and distinct functions, i.e. FcR binding function and multimerization function. Generally speaking, it is common practice to include small linking sequences between domains with independent structures and/or functions in order to avoid any steric constraints or diminish the independent functions of the flanking domains. However, as disclosed herein, removal of these short segments can provide a dramatic enhancement of multimer formation, receptor binding, and/or overall biological activity.

In one embodiment, the current invention relates to a stradomer unit comprising a leader sequence, an IgG1 Fc domain and a multimerization domain. In a further embodiment of the present invention, the leader sequence is directly linked to the IgG1 Fc domain and the IgG1 Fc domain is directly linked to the multimerization domain.

In another embodiment, the current invention relates to a stradomer unit wherein the amino acid sequence of the IgG1 Fc domain is at least 80% homologous to SEQ ID NO:2. In a further embodiment the amino acid sequence of the IgG1 Fc domain is at least 90% homologous to SEQ ID NO:2. In yet a further embodiment, the amino acid sequence of the IgG1 Fc domain is at least 95% homologous to SEQ ID NO: 2. In still a further embodiment, the amino acid sequence of the IgG1 Fc domain is at least 99% homologous to SEQ ID NO:2. In a further embodiment the amino acid sequence of the IgG1 Fc domain of SEQ ID NO: 2 is directly linked to a leader sequence and/or a multimerization domain. In some embodiments, the stradomer unit of the current invention binds FcγRIIIa or DC-SIGN/SIGN-R1 when multimerized.

In another embodiment, the current invention relates to a the stradomer unit wherein the amino acid sequence of the multimerization domain is at least 80% homologous to SEQ ID NO:3. In a further embodiment, the multimerization domain is at least 90% homologous to SEQ ID NO:3. In yet a further embodiment, the stradomer unit of the current invention wherein the amino acid sequence of the multimerization domain is at least 95% homologous to SEQ ID NO:3. In still a further embodiment, the stradomer unit of the current invention wherein the amino acid sequence of the multimerization domain is at least 99% homologous to SEQ ID NO:3. In another embodiment, the multimerization domain is capable of multimerizing the stradomer units. In a further embodiment, the multimerization domain is directly linked to the carboxy terminus of the IgG1 Fc domain. In some embodiments, the multimerization domain is directly linked to the amino terminus of the IgG1 Fc domain.

In another embodiment, the current invention relates to a stradomer unit wherein the amino acid sequence of the multimerization domain is at least 80% homologous to SEQ ID NO:5 In a further embodiment, the multimerization domain is at least 90% homologous to SEQ ID NO:5 In yet a further embodiment, the stradomer unit of the current invention wherein the amino acid sequence of the multimerization domain is at least 95% homologous to SEQ ID NO:5 In still a further embodiment, the stradomer unit of the current invention wherein the amino acid sequence of the multimerization domain is at least 99% homologous to SEQ ID NO:5 In another embodiment, the multimerization domain is capable of multimerizing the stradomer units. In a further embodiment, the multimerization domain is directly linked to the carboxy terminus to of the IgG1 Fc domain. In some embodiments, the multimerization domain is directly linked to the amino terminus of the IgG1 Fc domain.

In another embodiment, the current invention relates to a stradomer unit wherein the amino acid sequence of the multimerization domain is at least 80% homologous to SEQ ID NO:26 In a further embodiment, the multimerization domain is at least 90% homologous to SEQ ID NO:26 In yet a further embodiment, the stradomer unit of the current invention wherein the amino acid sequence of the multimerization domain is at least 95% homologous to SEQ ID NO:26 In still a further embodiment, the stradomer unit of the current invention wherein the amino acid sequence of the multimerization domain is at least 99% homologous to SEQ ID NO:26 In another embodiment, the multimerization domain is capable of multimerizing the stradomer units. In a further embodiment, the multimerization domain is directly linked to the carboxy terminus to of the IgG1 Fc domain. In some embodiments, the multimerization domain is directly linked to the amino terminus of the IgG1 Fc domain.

In one embodiment, the current invention relates to a stradomer unit comprising a leader sequence directly linked to an IgG1 Fc domain which is directly linked to an IgG2 hinge multimerization domain wherein the IgG2 hinge creates multimers of the stradomer units. In one embodiment, the amino acid sequence of the stradomer unit is at least 80% homologous to SEQ ID NO: 4 In a further embodiment, the amino acid sequence of the stradomer unit is at least 90% homologous to SEQ ID NO: 4. In still a further embodiment, the amino acid sequence of the stradomer unit is at least 95% homologous to SEQ ID NO: 4. In yet another embodiment, the amino acid sequence of the stradomer unit is at least 99% homologous to SEQ ID NO: 4. In a further embodiment, the leader sequence (SEQ ID NO: 1) is cleaved from the mature protein.

In one embodiment, the current invention relates to a stradomer unit comprising a leader sequence directly linked to an IgG1 Fc domain which is directly linked to an isoleucine zipper multimerization domain wherein the isoleucine zipper creates multimers of the stradomer units. In one embodiment, the amino acid sequence of the stradomer unit is at least 80% homologous to SEQ ID NO: 10 In a further embodiment, the amino acid sequence of the stradomer unit is at least 90% homologous to SEQ ID NO: 10. In still a further embodiment, the amino acid sequence of the stradomer unit is at least 95% homologous to SEQ ID NO: 10. In yet another embodiment, the amino acid sequence of the stradomer unit is at least 99% homologous to SEQ ID NO: 10. In a further embodiment, the leader sequence (SEQ ID NO: 1) is cleaved from the mature protein.

In one embodiment, the current invention relates to a stradomer unit comprising a leader sequence directly linked to an IgG1 Fc domain which is directly linked to a GPP multimerization domain wherein the GPP multimerization domain creates multimers of the stradomer units. In one embodiment, the amino acid sequence of the stradomer unit is at least 80% homologous to SEQ ID NO: 27 In a further embodiment, the amino acid sequence of the stradomer unit is at least 90% homologous to SEQ ID NO: 27. In still a further embodiment, the amino acid sequence of the stradomer unit is at least 95% homologous to SEQ ID NO: 27. In yet another embodiment, the amino acid sequence of the stradomer unit is at least 99% homologous to SEQ ID NO: 27. In a further embodiment, the leader sequence (SEQ ID NO: 1) is cleaved from the mature protein.

In one embodiment, the current invention relates to a stradomer unit comprising a leader sequence directly linked to an IgG2 hinge multimerization domain which is in turn directly linked to an IgG1 Fc domain wherein the IgG2 hinge creates multimers of the stradomer units. In one embodiment, the amino acid sequence of the stradomer unit is at least 80% homologous to SEQ ID NO: 8 In a further embodiment, the amino acid sequence of the stradomer unit is at least 90% homologous to SEQ ID NO: 8. In still a further embodiment, the amino acid sequence of the stradomer unit is at least 95% homologous to SEQ ID NO: 8. In yet another embodiment, the amino acid sequence of the stradomer unit is at least 99% homologous to SEQ ID NO: 8. In a further embodiment, the leader sequence (SEQ ID NO: 1) is cleaved from the mature protein.

In one embodiment, the current invention relates to a stradomer unit comprising a leader sequence directly linked to an isoleucine zipper multimerization domain which is in turn directly linked to an IgG1 Fc domain wherein the isoleucine zipper creates multimers of the stradomer units. In one embodiment, the amino acid sequence of the stradomer unit is at least 80% homologous to SEQ ID NO: 9 In a further embodiment, the amino acid sequence of the stradomer unit is at least 90% homologous to SEQ ID NO: 9. In still a further embodiment, the amino acid sequence of the stradomer unit is at least 95% homologous to SEQ ID NO: 9. In yet another embodiment, the amino acid sequence of the stradomer unit is at least 99% homologous to SEQ ID NO: 9. In a further embodiment, the leader sequence (SEQ ID NO: 1) is cleaved from the mature protein.

In one embodiment, the current invention relates to a stradomer unit comprising a leader sequence directly linked to a GPP multimerization domain which is in turn directly linked to an IgG1 Fc domain wherein the GPP multimerization domain creates multimers of the stradomer units. In one embodiment, the amino acid sequence of the stradomer unit is at least 80% homologous to SEQ ID NO: 28 In a further embodiment, the amino acid sequence of the stradomer unit is at least 90% homologous to SEQ ID NO: 28. In still a further embodiment, the amino acid sequence of the stradomer unit is at least 95% homologous to SEQ ID NO: 28. In yet another embodiment, the amino acid sequence of the stradomer unit is at least 99% homologous to SEQ ID NO: 28. In a further embodiment, the leader sequence (SEQ ID NO: 1) is cleaved from the mature protein.

In another embodiment, the current invention relates to a stradomer unit comprising a leader sequence directly linked to an IgG1 Fc domain which in turn is directly linked to a multimerization domain wherein the multimerization domain creates multimers of the stradomer units. In a further embodiment, the multimerization domain creates high order multimers of the stradomer units. In still a further embodiment, at least about 35% of the resulting stradomer composition contains multimers of the stradomer units. In still a further embodiment, at least about 55% of the resulting stradomer composition contains multimers of the stradomer units. In still a further embodiment, at least about 65% of the resulting stradomer composition contains multimers of the stradomer units. In still a further embodiment, at least about 70% of the resulting stradomer composition contains multimers of the stradomer units. In still a further embodiment, at least about 75% of the resulting stradomer composition contains multimers of the stradomer units.

In one embodiment, the current invention relates to a stradomer unit comprising a leader sequence, an IgG1 Fc domain with one or more mutations and a multimerization domain. In a further embodiment of the present invention, the leader sequence is directly linked to the IgG1 Fc domain with one or more mutations and the IgG1 Fc domain with one or more mutations is directly linked to the multimerization domain.

In one embodiment, the current invention relates to a stradomer unit wherein the amino acid sequence of the stradomer unit comprises SEQ ID NO:20. In a further embodiment, the invention relates to a cluster stradomer comprising at least two stradomer units comprising SEQ ID NO:20. In a further embodiment, the leader sequence (SEQ ID NO: 1) is cleaved from the mature protein.

In one embodiment, the current invention relates to a stradomer unit wherein the amino acid sequence of the stradomer unit comprises SEQ ID NO:24. In a further embodiment, the invention relates to a cluster stradomer comprising at least two stradomer units comprising SEQ ID NO:24. In a further embodiment, the leader sequence (SEQ ID NO: 1) is cleaved from the mature protein.

In one embodiment, the current invention relates to a stradomer unit wherein the amino acid sequence of the stradomer unit comprises SEQ ID NO:21. In a further embodiment, the invention relates to a cluster stradomer comprising at least two stradomer units comprising SEQ ID NO:21. In a further embodiment, the leader sequence (SEQ ID NO: 1) is cleaved from the mature protein.

In one embodiment, the current invention relates to a stradomer unit comprising a leader sequence directly linked to a multimerization domain wherein the multimerization domain is directly linked to an IgG1 Fc domain which lacks the IgG1 hinge domain, wherein the multimerization domain creates multimers of the stradomer units. In another embodiment, the current invention relates to a stradomer unit comprising a leader sequence directly linked to a multimerization domain wherein the multimerization domain is directly linked to a portion of an IgG1 Fc that is capable of binding an FcR or wherein the multimerization domain directly linked to a portion of an IgG1 Fc together are capable of binding an FcR.

In one embodiment, the current invention relates to a stradomer unit comprising a leader sequence directly linked to a multimerization domain which in turn is directly linked to an IgG1 Fc domain which consists of IgG1 hinge, CH2 and CH3 domains, wherein the multimerization domain creates multimers of the stradomer units.

In one embodiment, the current invention relates to a stradomer unit comprising a leader sequence directly linked to a multimerization domain which in turn is directly linked to an IgG1 Fc domain which consists of IgG1 CH2 and CH3 domains, wherein the multimerization domain creates multimers of the stradomer units.

In one embodiment, the current invention relates to a stradomer unit comprising a leader sequence directly linked to an Fc domain comprising an IgG2 hinge, which is directly linked to an IgG1 CH2 and IgG1 CH3 domain wherein the IgG2 hinge creates multimers of the stradomer units. In one embodiment, the amino acid sequence of the stradomer unit is at least 80% homologous to SEQ ID NO: 18. In a further embodiment, the amino acid sequence of the stradomer unit is at least 90% homologous to SEQ ID NO: 18. In still a further embodiment, the amino acid sequence of the stradomer unit is at least 95% homologous to SEQ ID NO: 18. In yet another embodiment, the amino acid sequence of the stradomer unit is at least 99% homologous to SEQ ID NO: 18. In a further embodiment, the leader sequence (SEQ ID NO: 1) is cleaved from the mature protein.

In one embodiment, the current invention relates to a stradomer unit comprising an IgG1 Fc domain directly linked to a multimerizationdomain. In one embodiment the IgG1 Fc domain is at least about 80%, or at least about 90% or at least about 95% or at least about 99% homologous to SEQ ID NO:2. In another embodiment, the IgG1 Fc domain is at least about 80%, or at least about 90% or at least about 95% or at least about 99% homologous to SEQ ID NO:19. In a further embodiment, the IgG1 Fc domain contains one or more mutations. In one embodiment, the mutlimerization domain is at least about 80%, or at least about 90% or at least about 95% or at least about 99% homologous to SEQ ID NO:3. In another embodiment, the multimerization domain is at least about 80%, or at least about 90% or at least about 95% or at least about 99% homologous to SEQ ID NO:5. In still another embodiment, the mutimerization domain is at least about 80%, or at least about 90% or at least about 95% or at least about 99% homologous to SEQ ID NO:26. In one embodiment, the multimerization domain is directly linked to the N terminus of the IgG1 Fc domain. In another embodiment, the multimerization domain is directly linked to the C terminus of the IgG1 Fc domain.

In one embodiment, the current invention relates to a cluster stradomer comprising at least two stradomer monomers each comprising a leader sequence directly linked to an IgG1 Fc domain which in turn is directly linked to a multimerization domain. In a further embodiment, the cluster stradomer binds to FcγRIIIa. In a further embodiment, the cluster stradomer binds to FcγRIIb.

In another embodiment, the current invention relates to a method of modulating an immune response to a subject comprising administering to the subject an effective amount of a cluster stradomer comprising at least two stradomer monomers each comprising a leader sequence directly linked to an IgG1 Fc domain which in turn is directly linked to a multimerization domain. In a further embodiment, the cluster stradomer binds to FcγRIIIa. In a further embodiment, the cluster stradomer binds to FcγRIIb. In a further embodiment, the modulation of the immune responses comprises induction of CD86 on immature dendritic cells.

In a further embodiment, the modulation of the immune responses is associated with selective apoptosis of certain memory B cells with a decrease in antibody production. In a further embodiment, the modulation is associated with selective apoptosis of activated memory B cells with a decrease in antibody production. In another embodiment, the immune modulation may be modulation of NK cells leading to an increase in antibody dependent cellular cytotoxicity. In still another embodiment, the modulation of the immune response may result in an increase in cellular populations expressing CD8beta and CD11c. In yet another embodiment, the immune modulation may lead to a decrease in proinflammatory cytokines or cytokines that are commonly elevated in autoimmune diseases such as IL-6 and IL-8. In another embodiment, the immune modulation may lead to activation of NKT cells and secretion and cleavage of TGF-beta.

In an additional embodiment, the current invention relates to a method of treating an inflammatory or autoimmune disease in a subject in need thereof comprising administering an effective amount of a stradomer comprising at least two stradomer units each comprising a leader sequence directly linked to an IgG1 Fc domain which in turn is directly linked to a multimerization domain or alternatively comprising a leader sequence directly linked to a multimerization domain which in turn is directly linked to a an IgG1 Fc domain. In a further embodiment, the inflammatory disease is an autoimmune disease. In yet a further embodiment, the autoimmune disease is selected from the group consisting of rheumatoid arthritis, multiple sclerosis, type I diabetes mellitus, autoimmune thyroiditis, idiopathic thrombocytopenia purpura, autoimmune anemia, chronic inflammatory demyelinating polyneuropathy, *scleroderma*, systemic lupus erythematosus, psoriasis, inflammatory bowel disease, autoimmune uveitis, ANCA positive vasculitis, celiac disease, *pemphigus*, dermatopolymyositis, Goodpasture's Disease, Myasthenia *gravis*, Grave's Disease, Kawasaki Disease, sickle cell crisis and atopic dermatitis. In yet a further embodiment, the autoimmune disease is associated with the transplantation of an organ from a donor to a recipient. In yet a further embodiment, the autoimmune disease is a disease that is not classically characterized as an autoimmune disease but in which cells of the immune system play an important role such as Alzheimer's disease, Parkinson's disease, Huntingdon's disease, osteopenia, and osteoporosis.

In a further embodiment the stradomer is administered intravenously, subcutaneously, orally, nasally, intraperitoneally, sublingually, bucally, transdermally, by subcutaneous or subdermal implantation, or intramuscularly. In one embodiment, the cluster stradomer is administered intravenously. Because of the enhanced efficacy of the stradomers of the current invention, in some embodiments the stradomers may be administered at a lower dose intravenously compared with the predecessor molecules and/or IVIG. In one embodiment, the cluster stradomer is administered intravenously at a dose of about 0.01 mg/Kg to about 1000 mg/Kg IV. In a further embodiment, the cluster stradomer is administered at about 0.1 mg/Kg to about 100 mg/Kg IV. In yet a further embodiment, the cluster stradomer is administered at about 0.5 mg/Kg to about 50 mg/Kg IV. In still a further embodiment, the cluster stradomer is administered at about 1 mg/Kg to about 25 mg/Kg IV. In still a further embodiment, the cluster stradomer is administered at about 5 mg/Kg to about 15 mg/Kg IV. In one embodiment, the cluster stradomer is administered subcutaneously. Because of the enhanced efficacy of the stradomers of the current invention, in some embodiments the stradomers may be administered at a lower dose subcutaneously compared with the predecessor molecules and/or IVIG. In one embodiment, the cluster stradomer is administered subcutaneously at a dose of about 0.01 mg/Kg to about 1000 mg/Kg SQ. In a further embodiment, the cluster stradomer is administered at about 0.2 mg/Kg to about 150 mg/Kg SQ. In yet a further embodiment, the cluster stradomer is administered at about 0.5 mg/Kg to about 80 mg/Kg SQ. In still a further embodiment, the cluster stradomer is administered at about 2 mg/Kg to about 50 mg/Kg SQ. In still a further embodiment, the cluster stradomer is administered at about 5 mg/Kg to about 30 mg/Kg SQ.

In one embodiment, the cluster stradomer is administered covalently fixed to an implantable device. In one embodiment the cluster stradomer is fixed to a suture. In another embodiment the cluster stradomer is fixed to a graft or stent. In another embodiment the cluster stradomer is fixed to a heart valve, an orthopedic joint replacement, or implanted electronic lead. In another embodiment the cluster stradomer is fixed to and embedded within an implantable matrix. In a preferred embodiment the cluster stradomer is fixed to and embedded within an implantable hydrogel. In one embodiment the hydrogel is comprised of dextran, polyvinyl alcohol, sodium polyacrylate, or acrylate polymers. In a further embodiment, the cluster stradomer is administered fixed in a hydrogel with pore sizes large enough to allow entry of immune cells to interact with the fixed cluster stradomer and then return to circulation. In a further embodiment, the pore size of the hydrogel is 5 to 50 microns. In a preferred embodiment, the pore size of the hydrogel is 25-30 microns.

In a further embodiment, the stradomer is administered before, during or after administration of one or more additional pharmaceutical and/or therapeutic agents. In a further embodiment the additional pharmaceutically active agent comprises a steroid; a biologic anti-autoimmune drug such as a monoclonal antibody, a fusion protein, or an anti-cytokine; a non-biologic anti-autoimmune drug; an immunosuppressant; an antibiotic; and anti-viral agent; a cytokine; or an agent otherwise capable of acting as an immune-modulator. In still a further embodiment, the steroid is prednisone, prednisolone, cortisone, dexamethasone, mometasone testosterone, estrogen, oxandrolone, fluticasone, budesonide, beclamethasone, albuterol, or levalbuterol. In still a further embodiment, the monoclonal antibody is infliximab, adalimumab, rituximab, tocilizumab, golimumab, ofatumumab, LY2127399, belimumab, veltuzumab, or certolizumab. In still a further embodiment, the fusion protein is etanercept or abatacept. In still a further embodiment, the anti-cytokine biologic is anakinra. In still a further embodiment, the anti-rheumatic non-biologic drug is cyclophophamide, methotrexate, azathioprine, hydroxychloroquine, leflunomide, minocycline, organic gold compounds, fostamatinib, tofacitinib, etoricoxib, or sulfasalazine. In still a further embodiment, the immunosuppressant is cyclosporine A, tacrolimus, sirolimus, mycophenolate mofetil, everolimus, OKT3, antithymocyte globulin, basiliximab, daclizumumab, or alemtuzumab. In still a further embodiment, the stradomer is administered before, during or after administration of a chemotherapeutic agent. In still a further embodiment, the stradomer and the additional therapeutic agent display therapeutic synergy when administered together. In one embodiment, the stradomer is administered prior to the administration of the additional therapeutic againt. In another embodiment, the stradomer is administered at the same time as the administration of the additional therapeutic agent. In still another embodiment, the stradomer is administered after the administration with the additional therapeutic agent.

In still another embodiment the invention relates to a method of treating an infectious disease in a subject in need thereof comprising administering an effective amount of a cluster stradomer comprising at least two stradomer units each comprising a leader sequence directly linked to an IgG1 Fc domain which in turn is directly linked to a multimerization domain or alternatively comprising a leader sequence directly linked to a multimerization domain which in turn is directly linked to a an IgG1 Fc domain. In yet a further embodiment, the infectious disease is a bacterial infection. In still another embodiment, the infectious disease is a viral infection. In a further embodiment, the infectious disease is bacterial or viral sepsis. In a further embodiment the cluster stradomer is administered intravenously, subcutaneously, orally, intraperitoneally, sublingually, bucally, transdermally, by subcutaneous or subdermal implantation, or intramuscularly. In one embodiment, the cluster stradomer is administered intravenously. In one embodiment, the cluster stradomer is administered intravenously. In one embodiment, the cluster stradomer is administered at a dose of about 0.01 mg/Kg to about 1000 mg/Kg. In a further embodiment, the cluster stradomer is administered at about 0.1 mg/Kg to about 100 mg/Kg. In yet a further embodiment, the cluster stradomer is administered at about 0.5 mg/Kg to about 50 mg/Kg. In still a further embodiment, the cluster stradomer is administered at about 1 mg/Kg to about 25 mg/Kg. In still a further embodiment, the cluster stradomer is administered at about 5 mg/Kg to about 15 mg/Kg.

In another embodiment, the cluster stradomer is administered to treat humans, non-human primates (e.g., monkeys, baboons, and chimpanzees), mice, rats, bovines, horses, cats, dogs, pigs, rabbits, goats, deer, sheep, ferrets, gerbils, guinea pigs, hamsters, bats, birds (e.g., chickens, turkeys, and ducks), fish and reptiles with species-specific or chimeric stradomer molecules. In yet another embodiment, the human is an adult or a child. In still another embodiment, the cluster stradomer is administered to prevent autoimmune disease. In a further embodiment the cluster stradomer is administered to prevent vaccine-associated autoimmune conditions in companion animals and livestock.

In yet another embodiment, the current invention relates to a method for blocking non-specific binding of antibodies in an in vitro or ex vivo assay comprising incubating target tissue or target cells with a composition comprising an effective amount of a cluster stradomer comprising at least two stradomer units each comprising a leader sequence directly linked to an IgG1 Fc domain which in turn is directly linked to a multimerization domain or alternatively comprising a leader sequence directly linked to a multimerization domain which in turn is directly linked to a an IgG1 Fc domain. In one embodiment, the antibodies are monoclonal antibodies. In another embodiment, the antibodies are polyclonal antibodies. In one embodiment, the in vitro or ex vivo assay is immunohistochemistry, flow cytometry, western blot or an immunofluorescent assay. In a further embodiment, the cluster stradomer is species-specific for the species of the target tissue or cells.

In still another embodiment, the current invention relates to a method for reducing endotoxin levels in a composition with an effective amount of a cluster stradomer comprising at least two stradomer units each comprising a leader sequence directly linked to an IgG1 Fc domain which in turn is directly linked to a multimerization domain or alternatively comprising a leader sequence directly linked to a multimerization domain which in turn is directly linked to a an IgG1 Fc domain. In a further embodiment, the cluster stradomer complexes with the endotoxin in the composition. In still a further embodiment, the method includes removing the stradomer-complexed-endotoxin from the composition. In one embodiment, the stradomer-complexed-endotoxin is removed by filtration from the composition. In one embodiment, the composition is a pharmaceutical composition.

In one embodiment, the current invention relates to a method of producing a cluster stradomer comprising expressing a stradomer unit comprising a leader sequence directly linked to an IgG1 Fc domain which in turn is directly linked to a multimerization domain or a leader sequence directly linking to a multimerization domain which is directly linked to an IgG1 Fc domain wherein the multimerization domain creates multimers of the stradomer units from a transfected cell comprising cloning the DNA sequence encoding the stradomers of SEQ ID NO:4, SEQ ID NO:8, SEQ ID NO: 9, SEQ ID NO: 10 or SEQ ID NO: 18 into an expression vector, transfecting the expression vector into a bacterial host, isolating the plasmid DNA containing DNA encoding the stradomer of SEQ ID NO:4, SEQ ID NO:8, SEQ ID NO: 9, SEQ ID NO: 10 or SEQ ID NO: 18 from the bacterial culture, linearizing the plasmid DNA containing DNA encoding the stradomer of SEQ ID NO:4, SEQ ID NO:8, SEQ ID NO: 9, SEQ ID NO: 10 or SEQ ID NO: 18 transfecting the linearized DNA into mammalian cells, expanding the positively transfected cells to obtain a pool of stably transected cells, harvesting the stradomer protein from the media, and purifying the stradomer protein, wherein the stradomer protein contains no extraneous sequences. In one embodiment, the expression vector contains a selectable marker. In a further embodiment, the selectable marker is an antibiotic resistance gene. In still a further embodiment, the antibiotic resistance gene is a neomycin resistance gene. In one embodiment, the mammalian cells are CHO cells, HEK293 cells, PER.C6 cells, CAP cells or other commercially relevant mammalian cells used for protein production. In one embodiment, the stradomer protein is purified by affinity chromatography. In a further embodiment, the protein is further purified by gel filtration. In a further embodiment, the protein is further purified by ion-exchange chromatography. In a further embodiment the protein is further purified by hydrophobic interaction chromatography.

BRIEF DESCRIPTION OF THE FIGURES

FIG. 1A-FIG. 1H illustrate schematics of the preferred stradomer of the current inventions. FIG. 1A is a schematic of the G045c stradomer; FIG. 1B is a schematic of the G045old stradomer; FIG. 1C is a schematic of the G046 stradomer; FIG. 1D is a schematic of the G019 stradomer; FIG. 1E is a schematic of the G028 stradomer; FIG. 1F is a schematic of the G051 stradomer; FIG. 1G is a schematic of the G089 stradomer; and FIG. 1H is a schematic of the G096 stradomer.

FIG. 4 shows the synergistic effect of the direct naturally linked stradomer compounds of the current invention has when administered with prednisolone in a collagen-induced arthritis.

FIG. 5A-FIG. 5E show the enhanced binding affinity of IgG2A (FIG. 5A), M046 (FIG. 5B), M045 (FIG. 5C), M019 (FIG. 5D) and M028 (FIG. 5E) compounds of the current invention to FcγRIIIa, FcγRIIb and SIGN-R1 compared to IgG2a controls.

Figure 6A:
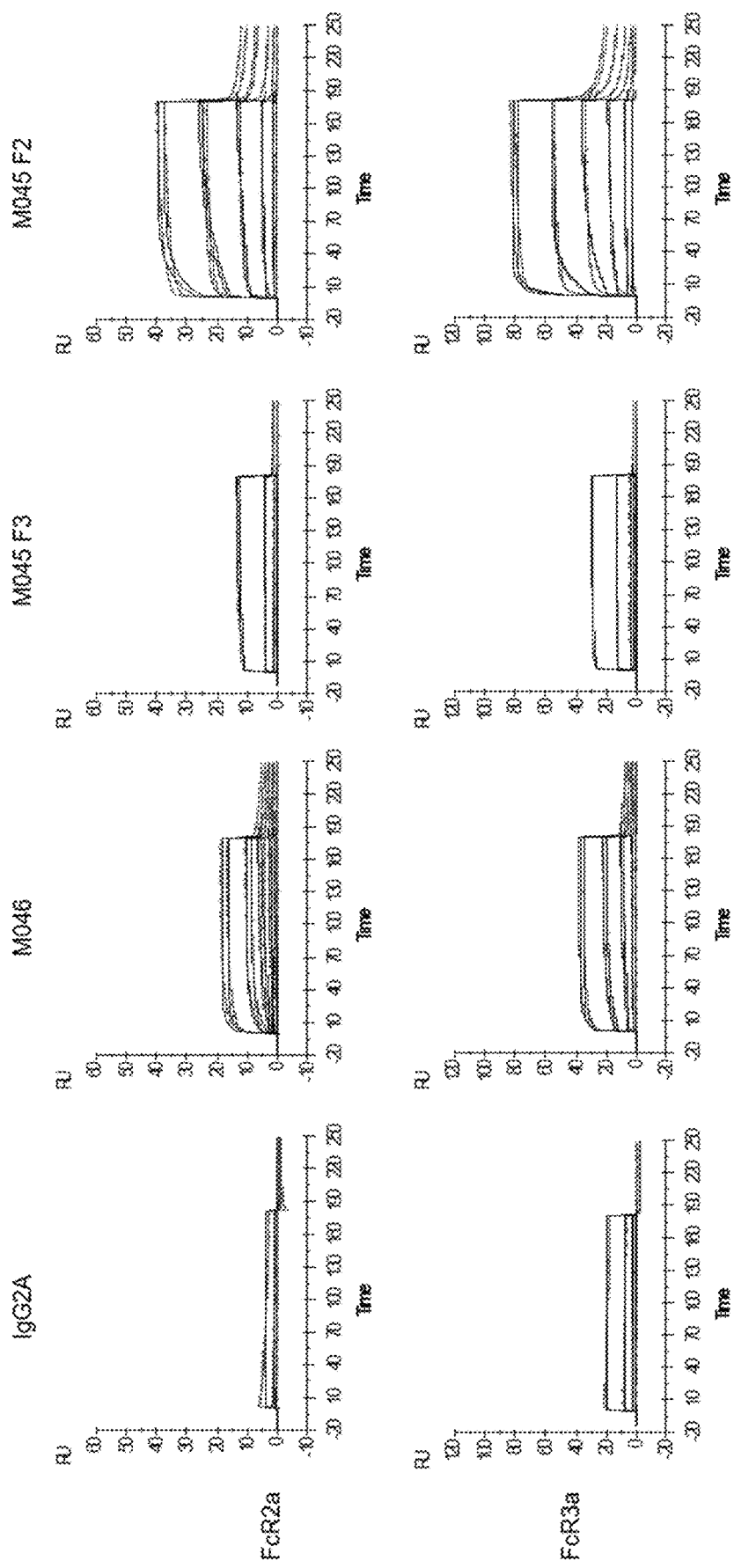
Figure 6B:
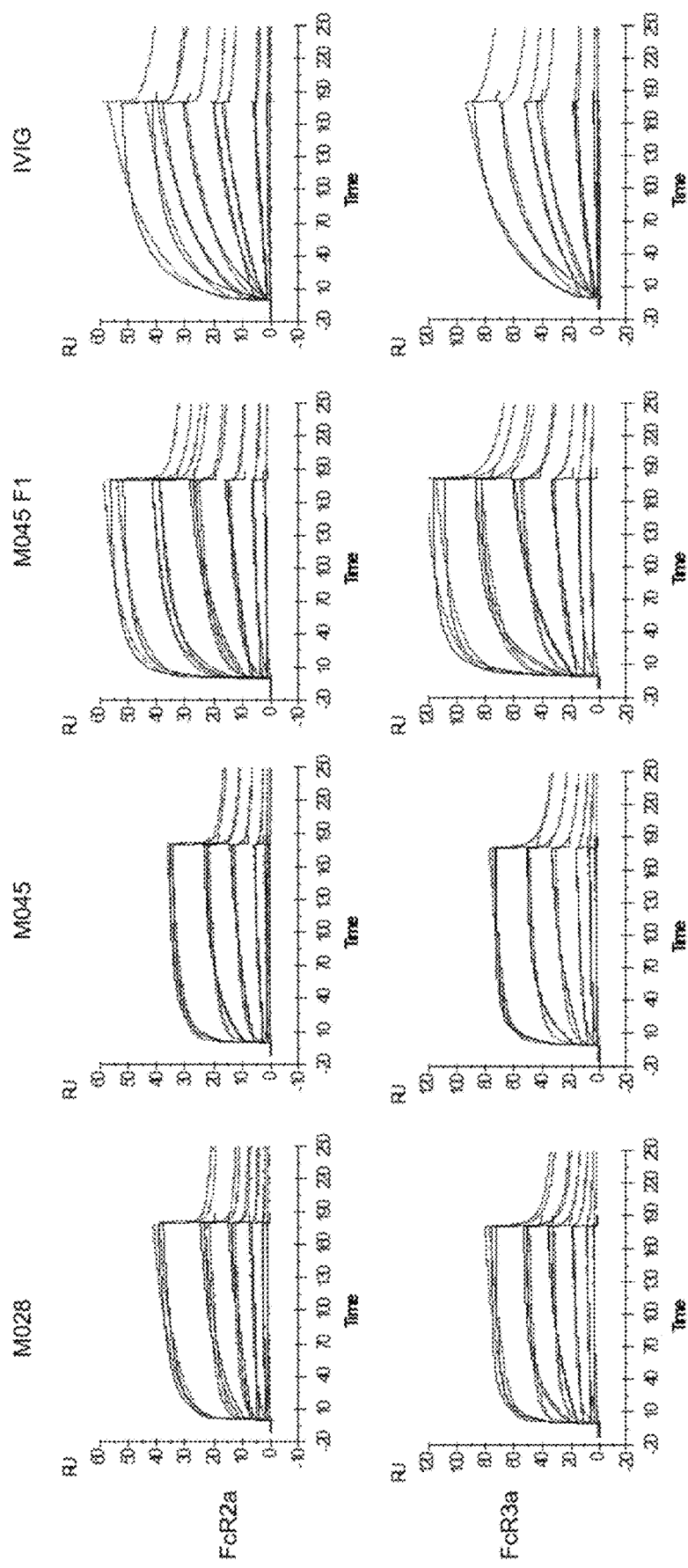
Figure 6C:
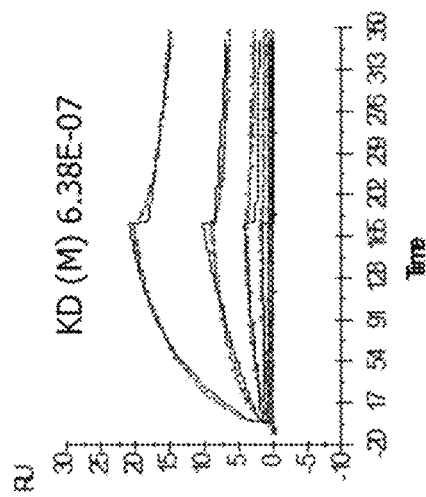
Figure 6C:
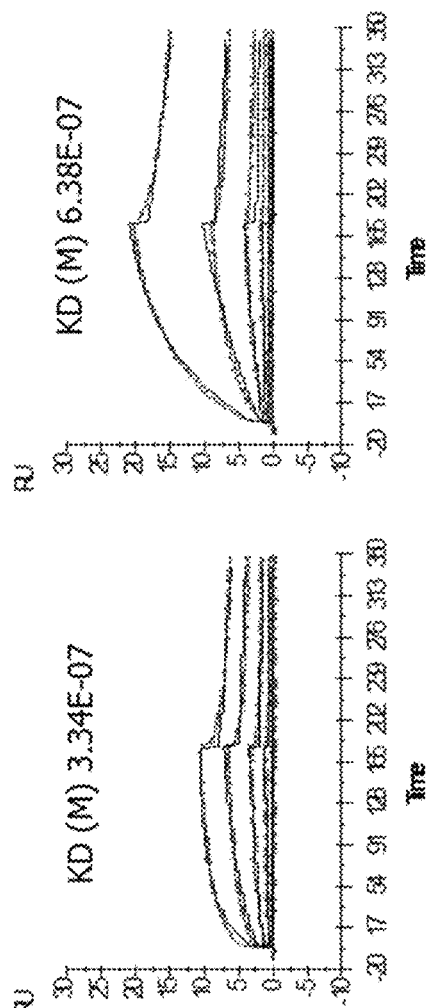
Figure 6C:
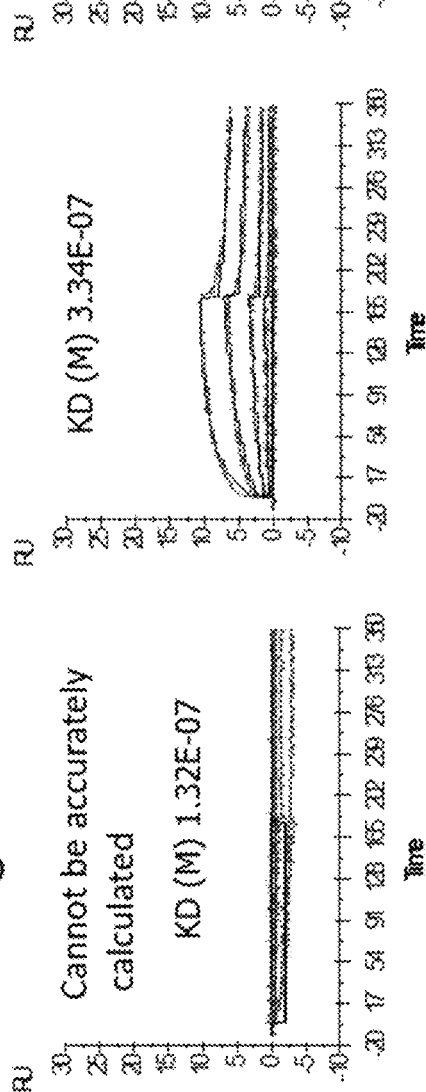

FIG. 6A-FIG. 6D show the enhanced binding affinity of the compounds of the current invention to FcγRIIb and FcγRIIIa (FIG. 6A and FIG. 6B) and SIGN-R1 (FIG. 6C and FIG. 6D). M045 F1 is a higher molecular weight multimer fraction of the stradomer while M045 F2 is the lower molecular weight multimer fraction of the stradomer. M045 F3 is the homodimer fraction of the stradomer.

Figure 7:
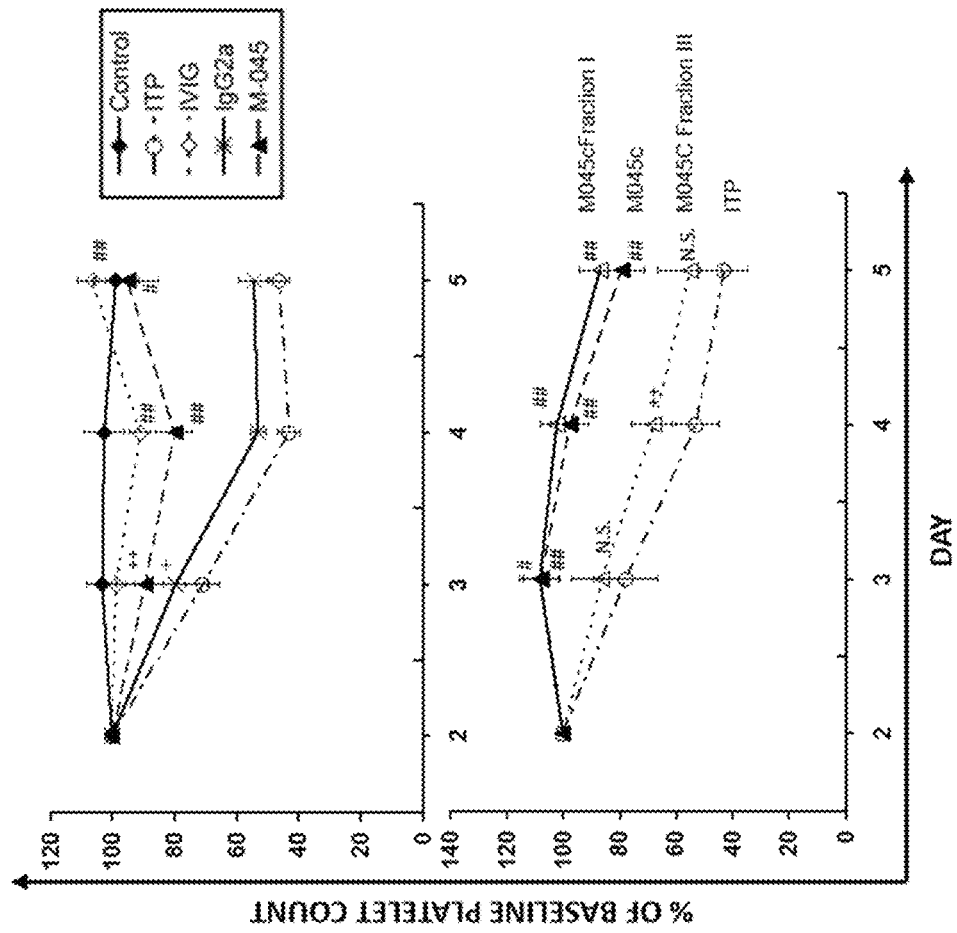

FIG. 7 shows the effect of the direct naturally linked stradomer M045c on the severity of idiopathic thrombocytopenia purpura (ITP).

Figure 8A:
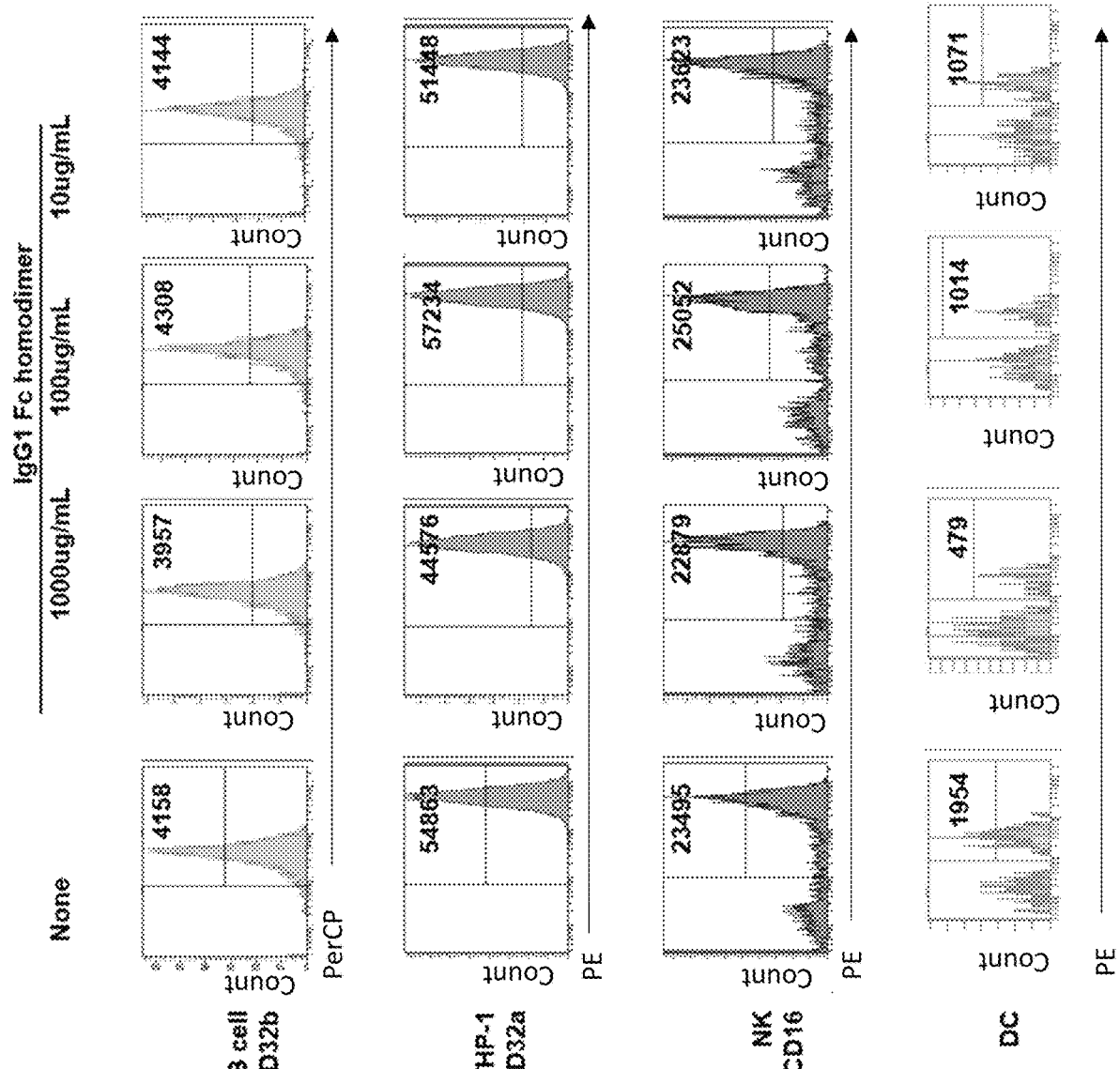
Figure 8B:
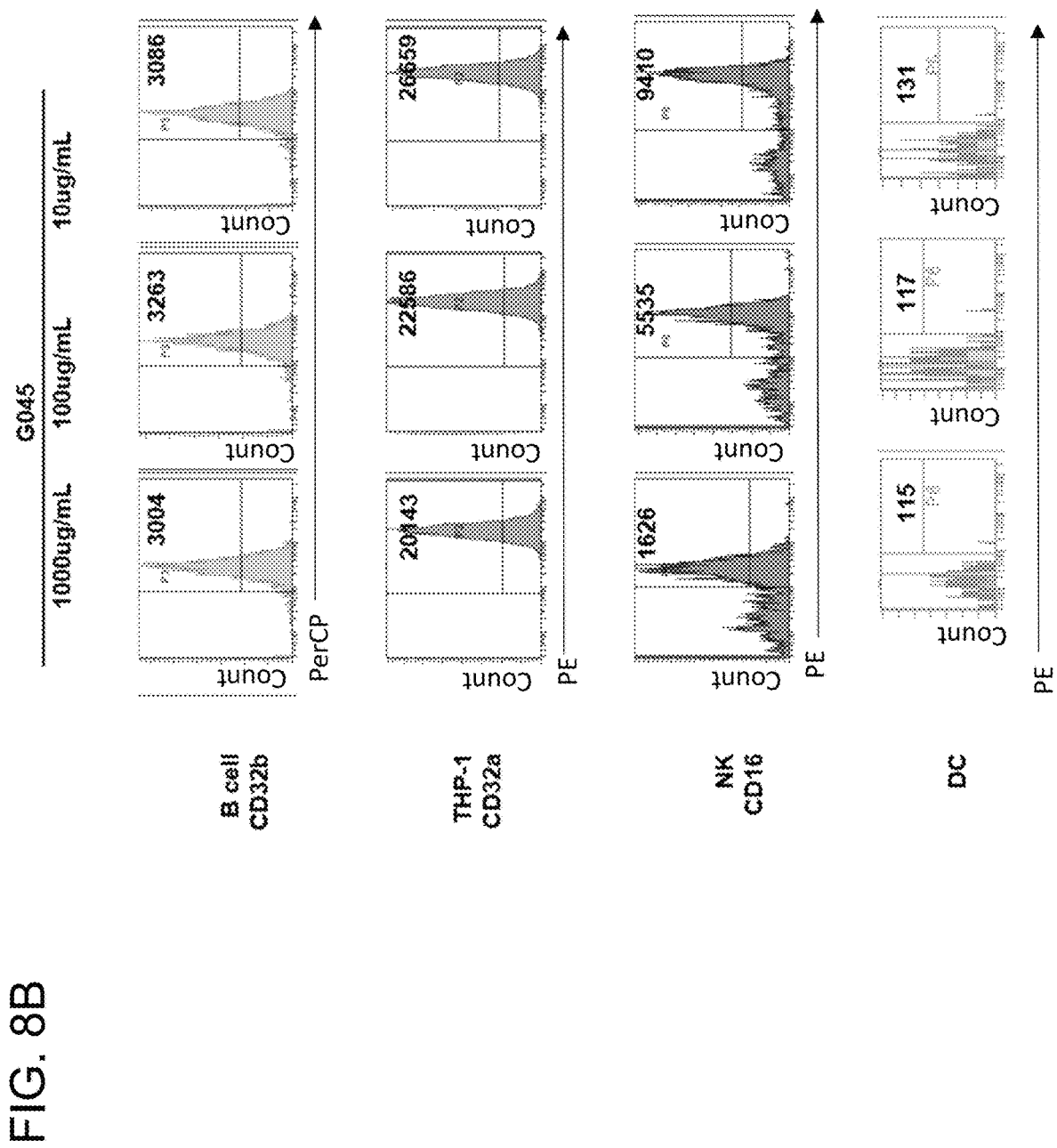

FIG. 8A-FIG. 8B show that stradomers (FIG. 8B) more effectively block the binding of anti-FcγR antibodies to FcγRs relative to IgG1 Fc control (FIG. 8A).

Figure 9:
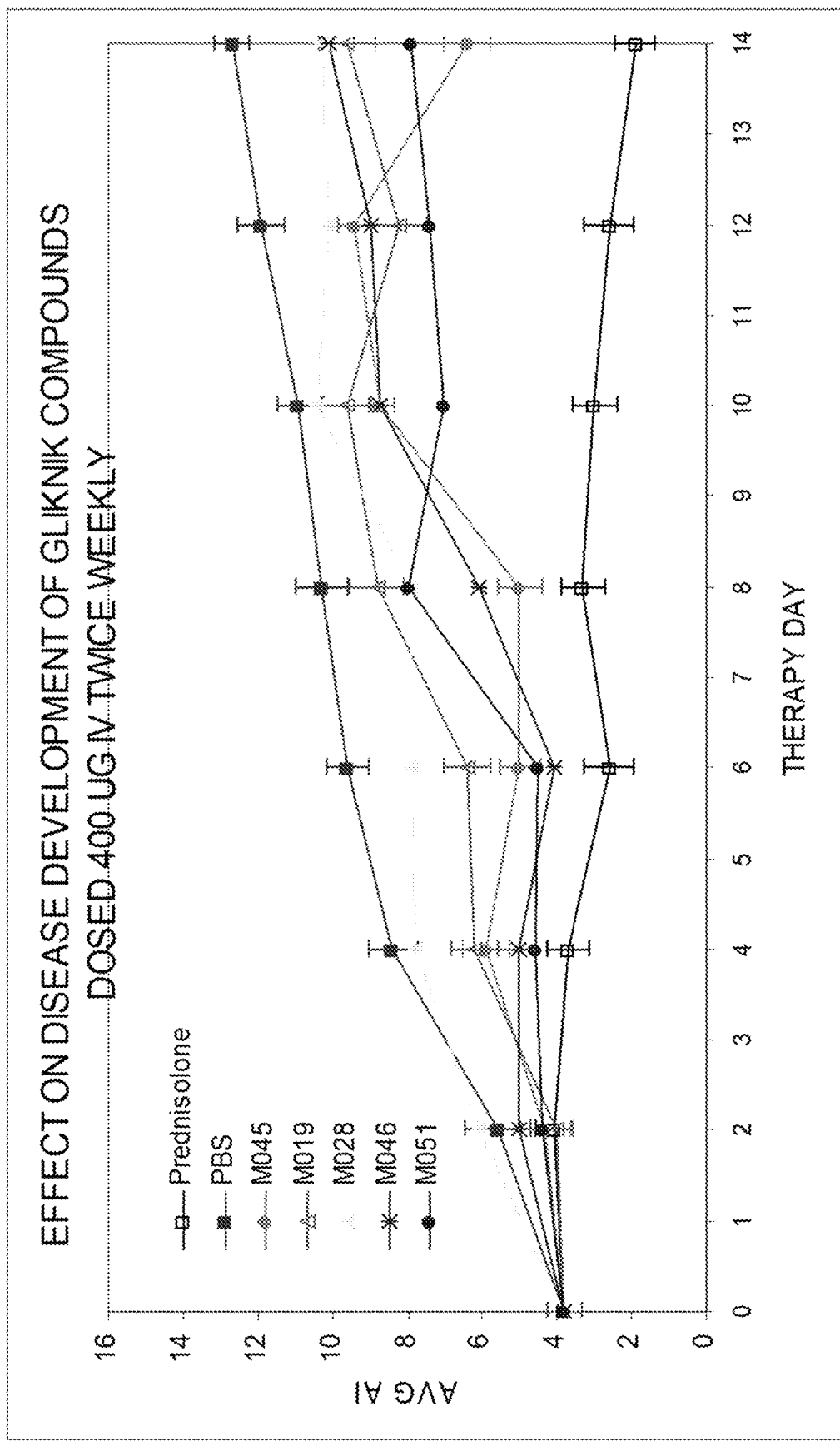

FIG. 9 shows the effect of the naturally linked stradomers M045c, M019, M028, M046 and M051 on the severity of a collagen induced arthritis mouse model.

Figure 10B:
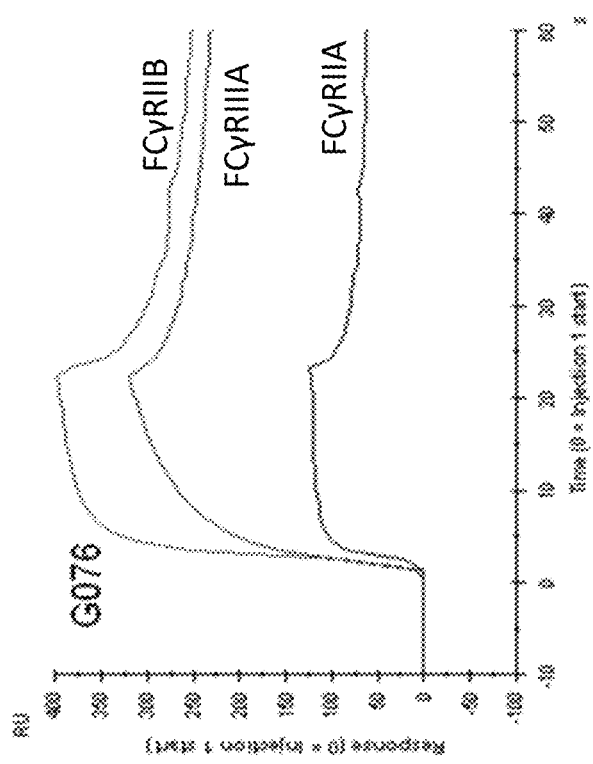
Figure 10A:
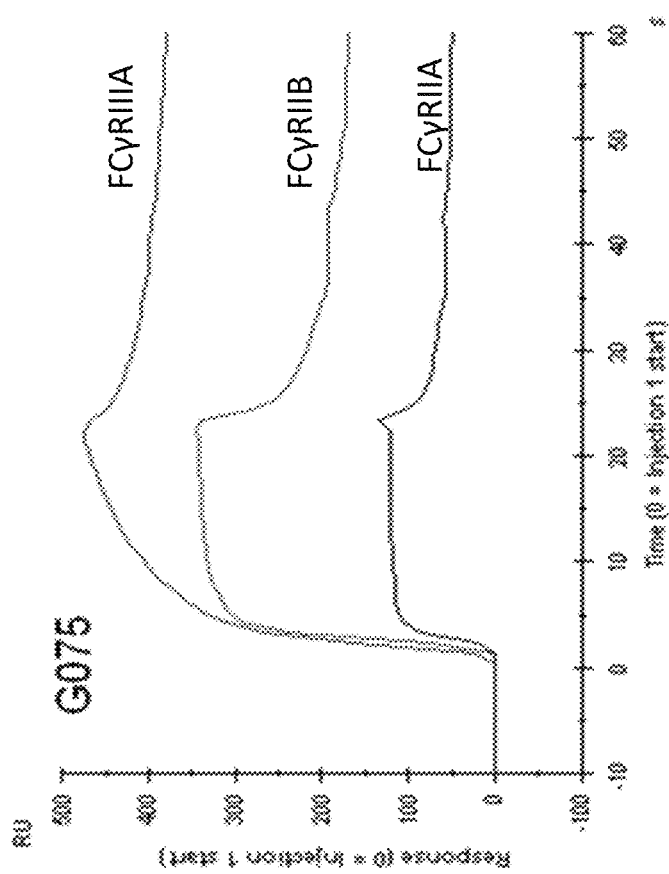

FIG. 10A-FIG. 10B shows the increased binding of the G075 stradomer to FcγRIIIa and decreased binding of the G075 stradomer to FcγRIIa and FcγRIIb (FIG. 10A) and the increased binding affinity of the G076 stradomer to FcγRIIa and FcγRIIb and decreased binding of the G076 stradomer to FcγRIIIa (FIG. 10B).

Figure 11A:
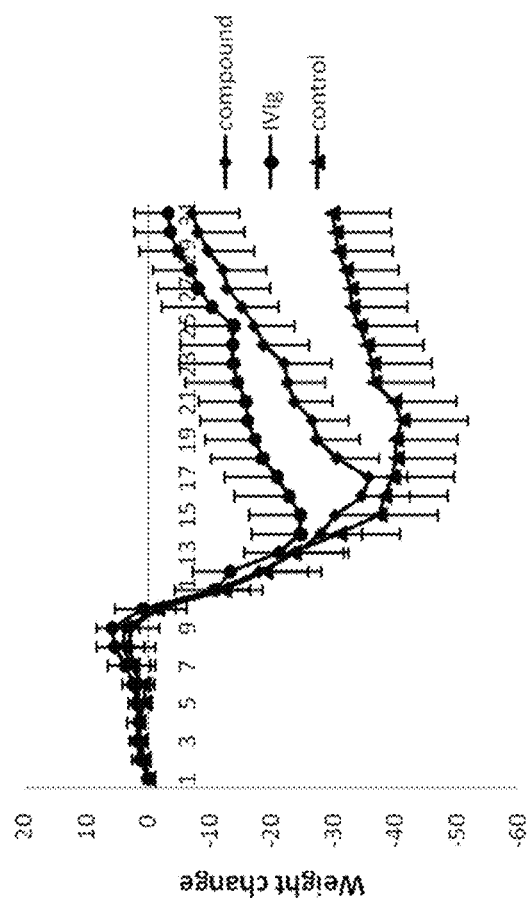
Figure 11B:
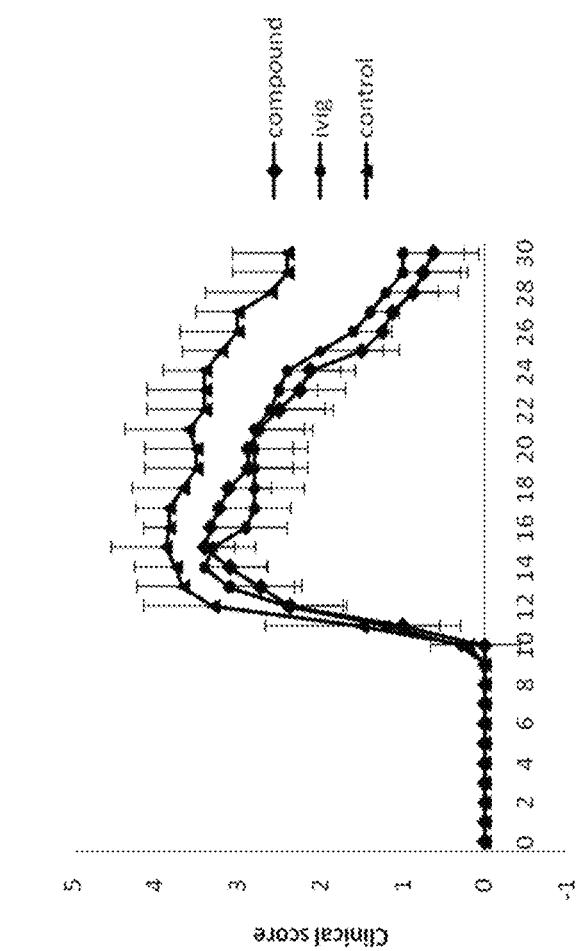
Figure 11C:
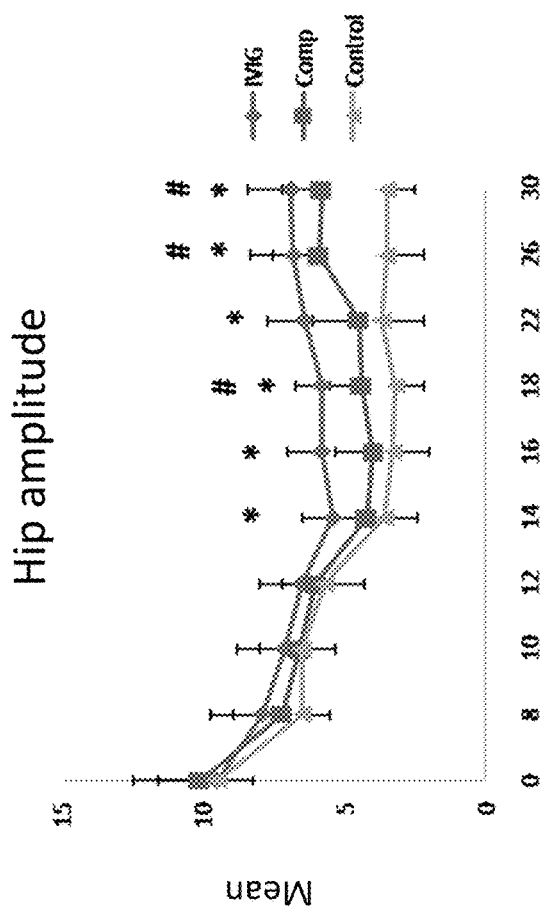
Figure 11D:
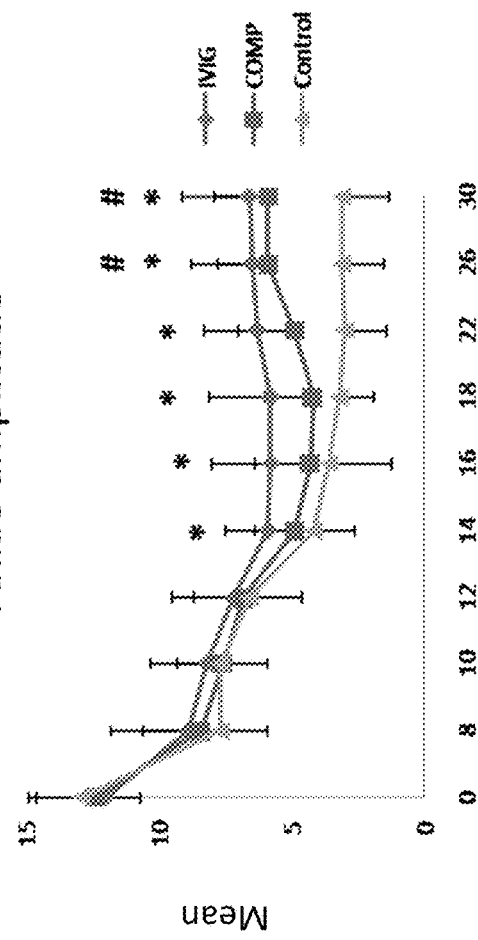
Figure 11E:
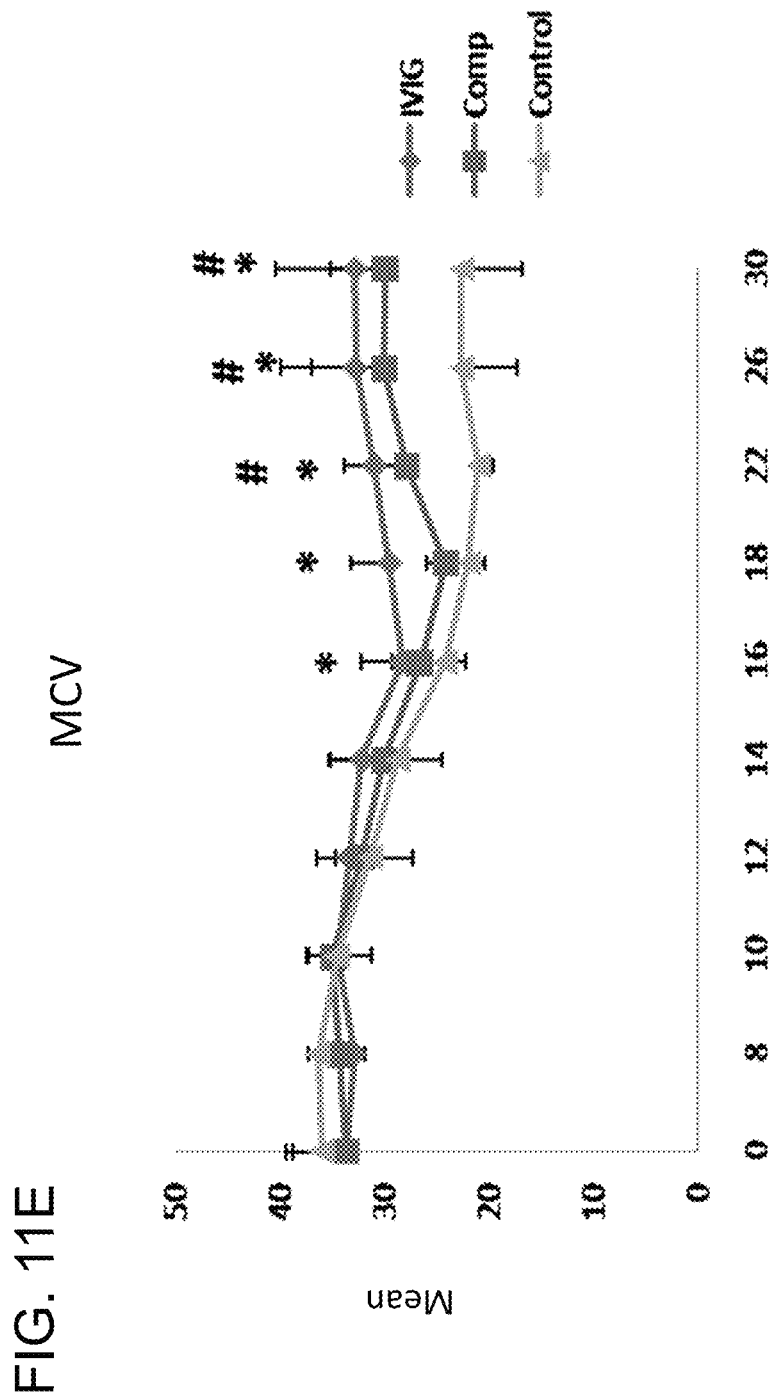

FIG. 11A-FIG. 11E shows the effect of M051 (compound) compared to IVIg and albumin controls in an animal model of experimental autoimmune neuritis in rats (EAN). FIG. 11A shows weight loss associated with experimental autoimmune neuritis in rats (EAN); FIG. 11B shows clinical score in EAN rats; FIG. 11C shows hip amplitude in EAN rats;

FIG. 11D shows ankle amplitude in EAN rats; and FIG. 11E shows motor nerve conduction velocity in EAN rats.

Figure 12E:
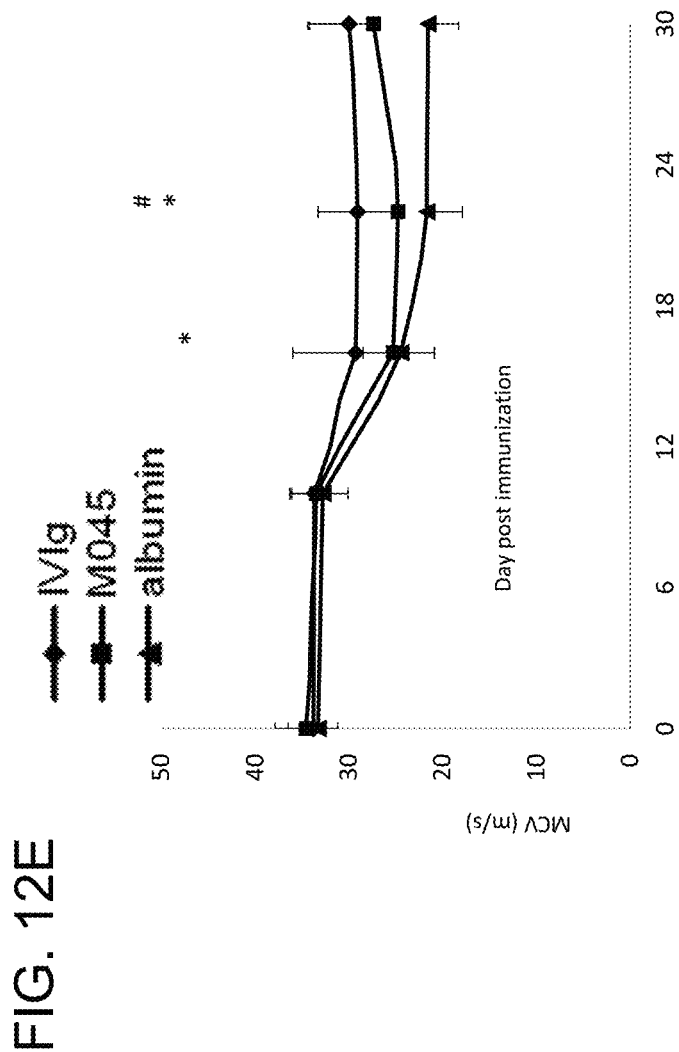

FIG. 12A-FIG. 12E shows the effect of M045c compared to IVIg and albumin controls in an animal model of experimental autoimmune neuritis in rats (EAN). FIG. 12A shows weight loss associated with experimental autoimmune neuritis in rats (EAN); FIG. 12B shows clinical score in EAN rats; FIG. 12C shows hip amplitude in EAN rats; FIG. 12D shows ankle amplitude in EAN rats; and FIG. 12E shows motor nerve conduction velocity in EAN rats.

Figure 13A:
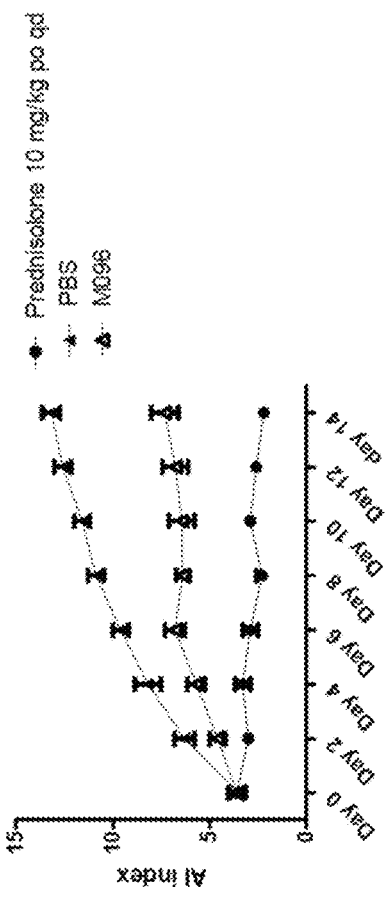
Figure 13B:
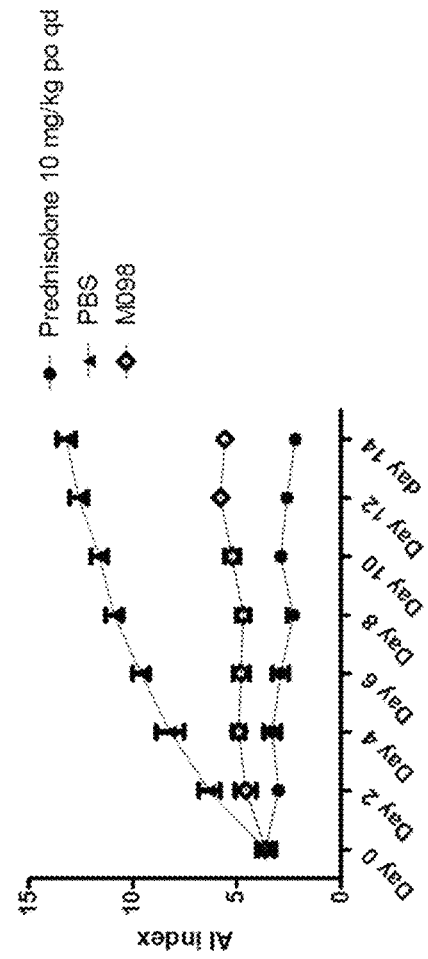
Figure 13C:
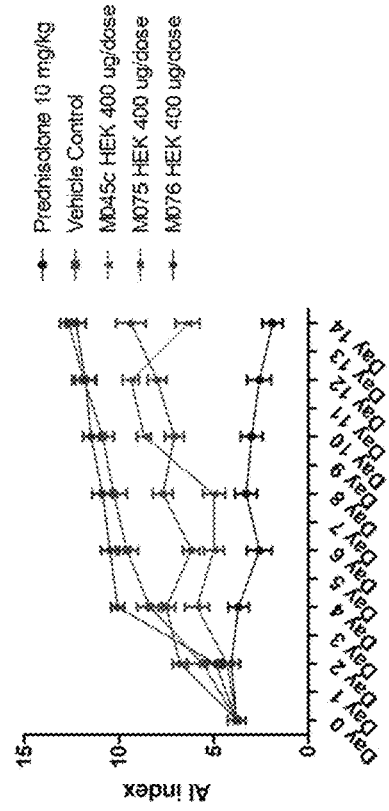

FIG. 13A-FIG. 13C shows the greater effect of the M075 (FIG. 13A), M096 (FIG. 13B) and M098 (FIG. 13C) but not M076 (FIG. 13A) naturally linked stradomers of the current invention compared with that of vehicle control and M045c positive control on the severity of collagen induced arthritis.

DETAILED DESCRIPTION OF THE INVENTION

The approach to rational molecular design for hIVIG replacement compounds described herein includes recombinant and/or biochemical creation of immunologically active biomimetic(s) which are surprisingly more efficient at multimerization and consequently binding to Fc gamma receptors than previously described molecules aimed to achieve this goal. The replacement compounds have utility for treating, for example, autoimmune diseases, inflammatory diseases, cancer and sepsis. Because of superior binding affinity to Fc gamma receptors relative to native immunoglobulin, the compositions also have utility as Fc blocking reagents in antibody-based immunoassays and in endotoxin removal from pharmaceutical and laboratory compositions. Each embodiment is described in detail below along with specific exemplary embodiments.

As used herein, the use of the word "a" or "an" when used in conjunction with the term "comprising" in the claims and/or the specification may mean "one," but it is also consistent with the meaning of "one or more," "at least one," and "one or more than one."

As used herein, the terms "biomimetic", "biomimetic molecule", "biomimetic compound", and related terms, refer to a human made compound that imitates the function of another compound, such as pooled hIVIG, a monoclonal antibody or the Fc fragment of an antibody. "Biologically active" biomimetics are compounds which possess biological activities that are the same as or similar to their naturally occurring counterparts. By "naturally occurring" is meant a molecule or portion thereof that is normally found in an organism. By naturally occurring is also meant substantially naturally occurring. "Immunologically active" biomimetics are biomimetics which exhibit immunological activity the same as or similar to naturally occurring immunologically active molecules, such as antibodies, cytokines, interleukins and other immunological molecules known in the art. In preferred embodiments, the biomimetics of the present invention are stradomers, as defined herein.

By "directly linked" is meant two sequences connected to each other without intervening or extraneous sequences, for example, restriction enzyme recognition sites or cloning fragments. One of ordinary skill in the art will understand that "directly linked" encompasses the addition or removal of amino acids so long as the multimerization capacity is substantially unaffected.

By "homologous" is meant identity over the entire sequence of a given nucleic acid or amino acid sequence. For example, by "80% homologous" is meant that a given sequence shares about 80% identity with the claimed sequence and can include insertions, deletions, substitutions, and frame shifts. One of ordinary skill in the art will understand that sequence alignments can be done to take into account insertions and deletions to determine identity over the entire length of a sequence.

The immunologically active biomimetics of the present invention are designed to possess one or more immune modulating activities of the IgG Fc domain and have at least (i) a first Fc domain capable of binding FcRn, DC-SIGN, SIGN-R1 and/or an FcγR including FcγR1, FcγRII, FcγRIII and FcγRIV, and (ii) a second Fc domain capable of binding FcRn, DC-SIGN, SIGN-R1 and/or an FcγR, including FcγR1, FcγRII, FcγRIII and FcγRIV. Specifically, the immunologically active compounds of the current invention are multimers of homodimers. Each homodimer possessing the ability to bind to FcRn, DC-SIGN, SIGN-R1 and/or and FCγR. Thus, when multimerized, the immunologically active biomimetics contain at least two homodimers each possessing the ability to bind to FcRn, DC-SIGN, SIGN-R1 and/or and FCγR.

The following paragraphs define the building blocks of the biomimetics of the present invention, both structurally and functionally, and then define biomimetics themselves. However, it is first helpful to note that, as indicated above, each of the biomimetics of the present invention has at least two Fc domains. At a minimum, an Fc domain is a dimeric polypeptide (or a dimeric region of a larger polypeptide) that comprises two peptide chains or arms (monomers) that associate to form a functional Fcγ receptor binding site. Therefore, the functional form of the individual fragments and domains discussed herein generally exist in a dimeric (or multimeric) form. The monomers of the individual fragments and domains discussed herein are the single chains or arms that must associate with a second chain or arm to form a functional dimeric structure.

Fc Fragment

"Fc fragment" is a term of art that is used to describe the protein region or protein folded structure that is routinely found at the carboxy terminus of immunoglobulins. The Fc fragment can be isolated from the Fab fragment of a monoclonal antibody through the use of enzymatic digestion, for example papain digestion, which is an incomplete and imperfect process (see Mihaesco C and Seligmann M. Papain Digestion Fragments Of Human IgM Globulins. Journal of Experimental Medicine, Vol 127, 431-453 (1968)). In conjunction with the Fab fragment (containing the antigen binding domain) the Fc fragment constitutes the holo-antibody, meaning here the complete antibody. The Fc fragment consists of the carboxy terminal portions of the antibody heavy chains. Each of the chains in an Fc fragment is between about 220-265 amino acids in length and the chains are often linked via a disulfide bond. The Fc fragment often contains one or more independent structural folds or functional subdomains. In particular, the Fc fragment encompasses an Fc domain, defined herein as the minimum structure that binds an Fcγ receptor. An isolated Fc fragment is comprised of two Fc fragment monomers (e.g., the two carboxy terminal portions of the antibody heavy chains; further defined herein) that are dimerized. When two Fc fragment monomers associate, the resulting Fc fragment has Fcγ receptor binding activity.

Fc Partial Fragment

An "Fc partial fragment" is a domain comprising less than the entire Fc fragment of an antibody, yet which retains sufficient structure to have the same activity as the Fc fragment, including Fcγ receptor binding activity. An Fc partial fragment may therefore lack part or all of a hinge region, part or all of a CH2 domain, part or all of a CH3 domain, and/or part or all of a CH4 domain, depending on the isotype of the antibody from which the Fc partial domain is derived. An example of a Fc partial fragment includes a molecule comprising the upper, core and lower hinge regions plus the CH2 domain of IgG3 (Tan, L K, Shopes, R J, Oi, V T and Morrison, S L, Influence of the hinge region on complement activation, CIq binding, and segmental flexibility in chimeric human immunoglobulins, Proc Natl Acad Sci USA. 1990 January; 87(1): 162-166). Thus, in this example the Fc partial fragment lacks the CH3 domain present in the Fc fragment of IgG3. Another example of an Fc partial fragment includes a molecule comprising the CH2 and CH3 domains of IgG1. In this example, the Fc partial fragment lacks the hinge domain present in IgG1. Fc partial fragments are comprised of two Fc partial fragment monomers. As further defined herein, when two such Fc partial fragment monomers associate, the resulting Fc partial fragment has Fcγ receptor binding activity.

Fc Domain

As used herein, "Fc domain" describes the minimum region (in the context of a larger polypeptide) or smallest protein folded structure (in the context of an isolated protein) that can bind to or be bound by an Fc receptor (FcR). In both an Fc fragment and an Fc partial fragment, the Fc domain is the minimum binding region that allows binding of the molecule to an Fc receptor. While an Fc domain can be limited to a discrete polypeptide that is bound by an Fc receptor, it will also be clear that an Fc domain can be a part or all of an Fc fragment, as well as part or all of an Fc partial fragment. When the term "Fc domains" is used in this invention it will be recognized by a skilled artisan as meaning more than one Fc domain. An Fc domain is comprised of two Fc domain monomers. As further defined herein, when two such Fc domain monomers associate, the resulting Fc domain has Fc receptor binding activity. Thus an Fc domain is a dimeric structure that can bind an Fc receptor.

Fc Partial Domain

As used herein, "Fc partial domain" describes a portion of an Fc domain. Fc partial domains include the individual heavy chain constant region domains (e.g., CH1, CH2, CH3 and CH4 domains) and hinge regions of the different immunoglobulin classes and subclasses. Thus, human Fc partial domains of the present invention include the CH1 domains of IgG1, IgG2, IgG3, IgG4, IgM, IgA1, IgA2, IgD and IgE, the CH2 domains of IgG1, IgG2, IgG3, IgG4, IgM, IgA1, IgA2, IgD and IgE, the CH3 domains of IgG1, IgG2, IgG3, IgG4, IgM, IgA1, IgA2, IgD and IgE, the CH4 domains of IgM and IgE, and the hinge regions of IgG1, IgG2, IgG3, IgG4, IgM, IgA1, IgA2, IgD and IgE. The corresponding Fc partial domains in other species will depend on the immunoglobulins present in that species and the naming thereof. Preferably, the Fc partial domains of the current invention include CH1, CH2 and hinge domains of IgG1 and the hinge domain of IgG2. The Fc partial domain of the present invention may further comprise a combination of more than one of these domains and hinges. However, the individual Fc partial domains of the present invention and combinations thereof lack the ability to bind an FcγR. Therefore, the Fc partial domains and combinations thereof comprise less than an Fc domain. Fc partial domains may be linked together to form a peptide that has Fcγ receptor binding activity, thus forming an Fc domain. In the present invention, Fc partial domains are used with Fc domains as the building blocks to create the biomimetics of the present invention, as defined herein. Each Fc partial domain is comprised of two Fc partial domain monomers. When two such Fc partial domain monomers associate, an Fc partial domain is formed.

As indicated above, each of Fc fragments, Fc partial fragments, Fc domains and Fc partial domains are dimeric proteins or domains. Thus, each of these molecules is comprised of two monomers that associate to form the dimeric protein or domain. While the characteristics and activity of the homodimeric forms was discussed above the monomeric peptides are discussed as follows.

Fc Fragment Monomer

As used herein, an "Fc fragment monomer" is a single chain protein that, when associated with another Fc fragment monomer, comprises an Fc fragment. The Fc fragment monomer is thus the carboxy terminal portion of one of the antibody heavy chains that make up the Fc fragment of a holo-antibody (e.g., the contiguous portion of the heavy chain that includes the hinge region, CH2 domain and CH3 domain of IgG). In one embodiment, the Fc fragment monomer comprises, at a minimum, one chain of a hinge region (a hinge monomer), one chain of a CH2 domain (a CH2 domain monomer) and one chain of a CH3 domain (a CH3 domain monomer), contiguously linked to form a peptide. In another embodiment, the Fc fragment monomer comprises at least one chain of a hinge region, one chain of a CH2 domain, one chain of a CH3 domain, and one chain of a CH4 domain (a CH4 domain monomer) contiguously linked to form a peptide. In one embodiment, the CH2, CH3 and hinge domains are from different isotypes. In a particular embodiment, the Fc fragment monomer contains an IgG2 hinge domain and IgG1 CH2 and CH3 domains.

Fc Domain Monomer

As used herein, "Fc domain monomer" describes the single chain protein that, when associated with another Fc domain monomer, comprises an Fc domain that can bind to an Fcγ receptor. The association of two Fc domain monomers creates one Fc domain. An Fc domain monomer alone, comprising only one side of an Fc domain, cannot bind an Fcγ receptor. The Fc domain monomers of the present invention do not contain extraneous sequences as did the previously described Fc domain monomers (See e.g. WO 2008/151088, FIGS. 17 and 18). Instead the Fc domain monomers of the current invention (SEQ ID NO: 2) are linked directly to the leader sequence (SEQ ID NO: 1) on one terminus (for example, the N-terminus of the Fc monomer) and to the multimerization domain (SEQ ID NO: 3) on the other terminus (for example, the C terminus of the Fc monomer). The resulting stradomer monomer of SEQ ID NO:4 is herein termed G045c. In another embodiment, the Fc domain monomer comprises an IgG2 hinge domain and IgG1 CH2 and CH3 domains are linked directly to the leader sequence (SEQ ID NO:1) on the N-terminus. The resulting stradomer monomer of SEQ ID NO:18 is herein termed G051. Alternatively, the multimerization domain (SEQ ID NO:3) can be placed at the amino terminus of the Fc domain monomer (SEQ ID NO:2). The resulting stradomer monomer of SEQ ID NO:8 is herein termed G019. Alternatively, the multimerization domain can comprise SEQ ID NO:5 instead of SEQ ID NO:3 and can be placed at the carboxy terminus of the Fc domain monomer, resulting in SEQ ID NO: 10 or it can be placed at the amino terminus of the Fc domain monomer, resulting in SEQ ID NO:9. These stradomers are herein termed G046 and G028, respectively.

Fc Partial Domain Monomer

As used herein, "Fc partial domain monomer" describes the single chain protein that, when associated with another Fc partial domain monomer, comprises an Fc partial domain. The association of two Fc partial domain monomers creates one Fc partial domain.

Stradomers

In particular embodiments, the biomimetics of the present invention include stradomers. Stradomers are biomimetic compounds capable of binding two or more Fc receptors, preferably two or more Fcγ receptors, and more preferably demonstrating significantly improved binding relative to an Fc Domain and most preferably demonstrating slow dissociation characteristic of avidity. In a preferred embodiment, the stradomers of the present invention are used to bind FcRn, DC-SIGN, SIGN-R1 and/or Fcγ receptors on effector cells such as NK cells and immature dendritic cells and other monocyte-derived cells. In one embodiment, the Fcγ receptors are low affinity Fcγ receptors. A stradomer can have four different physical conformations: serial, cluster, core or Fc fragment. The stradomers of the current invention are preferably cluster stradomers. As will be evident, the Fc fragments, Fc partial fragments, Fc domains and Fc partial domains discussed above are used in the construction of the various stradomer conformations. Further, it is the individual Fc domain monomers and Fc partial domain monomers, also discussed above, that are first produced, and that then self-associate to form the dimeric structures that are the stradomers of the present invention.

As used herein, a "stradomer dimer" is a specific form of a stradomer, composed of only two stradomer monomers. In one embodiment, the stradomer dimers are molecules formed by self-aggregation of relevant stradomer monomers. In another embodiment, stradomer monomers in the stradomer dimers are physically linked through an inter-stradomer monomer linkage, as defined herein. A "multimeric stradomer" is comprised of three or more stradomers, formed either by self-aggregation of stradomer monomers or through an inter-stradomer monomer linkage, as defined herein in.

Stradomer Monomer

As used herein, the term "stradomer monomer" or "stradomer unit" refers to a single, contiguous peptide molecule that, when associated with at least a second stradomer monomer, forms a polypeptide comprising at least two Fc domains. While in preferred embodiments cluster stradomer are comprised of two associated stradomer monomers, a cluster stradomer may also contain three or more stradomer monomers. Stradomer monomers may be associated to form stradomers by inter-stradomer monomer linkages or they may form stradomers through self-aggregation.

A stradomer monomer may have an amino acid sequence that will form one, two, three, four, five, six, seven, eight, nine, ten, eleven, twelve, thirteen, fourteen or more Fc domains when associated with another stradomer monomer to form a stradomer. A stradomer monomer may further have an amino acid sequence that will form one, two, three, four, five, six, seven, eight, nine, ten, eleven, twelve, thirteen, fourteen or more Fc partial domains when associated with another stradomer monomer to form a stradomer.

The regions of stradomer monomers that will form Fc domains and Fc partial domains in the context of a stradomer may simply be arranged from carboxy terminal to amino terminal of successive regions of the stradomer monomer molecule. The arrangement of the particular Fc domain monomers and Fc partial domain monomers comprising a stradomer monomer is not critical. However, the arrangement must permit formation of two functional Fc domains upon association of two stradomer monomers. In a preferred embodiment, the stradomer of the current invention contains a direct linkage between the N-terminus of the IgG1 Fc monomer (SEQ ID NO:2) and the C terminus of the leader peptide (SEQ ID NO:1) and the C terminus of the IgG1 Fc (SEQ ID NO:2) and the N terminus of the multimerization domain IgG2 hinge (SEQ ID NO:3) or the isoleucine zipper (SEQ ID NO:5) or the GPP domain (SEQ ID NO: 26) to form the G045c stradomer of SEQ ID NO:4, the G046 stradomer of SEQ ID NO: 10, or the G089 stradomer of SEQ ID NO: 27, respectively (Table 1). In another preferred embodiment, the stradomer of the current invention contains a direct linkage between the C terminus of the leader peptide (SEQ ID NO:1) and the N-terminus of the multimerization domain IgG2 hinge (SEQ ID NO:3), isoleucine zipper (SEQ ID NO:5) or the GPP domain (SEQ ID NO: 26) and a direct linkage between the C terminus of the multimerization domain (SEQ ID NOs: 3,5 or 26) and N terminus of the IgG1 Fc to form the G019 stradomer of SEQ ID NO: 8, the G028 stradomer of SEQ ID NO: 9 or the G096 stradomer of SEQ ID NO: 28, respectively (Table 1) or a direct linkage between the leader peptide (SEQ ID NO:1) and the N terminus of the multimerization domain (SEQ ID NO: 3) and direct linkage between the C terminus of the multimerization domain (SEQ ID NOs: 3) and N terminus of the IgG1 Fc partial domain containing the CH2 and CH3 portions of IgG1 to form the G051 stradomer of SEQ ID NO:18 (Table 1).

TABLE 1

| Stradomer | Sequence |
|---|---|
| G045c (SEQ ID NO: 4) | METDTLLLWVLLLWVPGSTGEPKSCDKTHTCPPCPAPELLGG PSVFLFPPKPKDTLMISRTPEVTCVVVDVSHEDPEVKFNWYV DGVEVHNAKTKPREEQYNSTYRVVSVLTVLHQDWLNGKEY KCKVSNKALPAPIEKTISKAKGQPREPQVYTLPPSREEMTKN |

TABLE 1-continued

| Stradomer | Sequence |
|---|---|
| | QVSLTCLVKGFYPSDIAVEWESNGQPENNYKTTPPVLDSDGS<br>FFLYSKLTVDKSRWQQGNVFSCSVMHEALHNHYTQKSLSLS<br>PGKERKCCVECPPCP |
| G019<br>(SEQ ID NO: 8) | METDTLLLWVLLLWVPGSTGERKCCVECPPCPEPKSCDKTH<br>TCPPCPAPELLGGPSVFLFPPKPKDTLMISRTPEVTCVVVDVS<br>HEDPEVKFNWYVDGVEVHNAKTKPREEQYNSTYRVVSVLT<br>VLHQDWLNGKEYKCKVSNKALPAPIEKTISKAKGQPREPQV<br>YTLPPSREEMTKNQVSLTCLVKGFYPSDIAVEWESNGQPENN<br>YKTTPPVLDSDGSFFLYSKLTVDKSRWQQGNVFSCSVMHEA<br>LHNHYTQKSLSLSPGK |
| G028<br>(SEQ ID NO: 9) | METDTLLLWVLLLWVPGSTGGGSIKQIEDKIEEILSKIYHIENE<br>IARIKKLIGERGHGGGSSEPKSCDKTHTCPPCPAPELLGGPSVF<br>LFPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQVSL<br>TCLVKGFYPSDIAVEWESNGQPENNYKTTPPVLDSDGSFFLY<br>SKLTVDKSRWQQGNVFSCSVMHEALHNHYTQKSLSLSPGK |
| G046<br>(SEQ ID NO: 10) | METDTLLLWVLLLWVPGSTGEPKSCDKTHTCPPCPAPELLGG<br>PSVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPSREEMTKN<br>QVSLTCLVKGFYPSDIAVEWESNGQPENNYKTTPPVLDSDGS<br>FFLYSKLTVDKSRWQQGNVFSCSVMHEALHNHYTQKSLSLS<br>PGKGGGSIKQIEDKIEEILSKIYHIENEIARIKKLIGERG |
| G051<br>(SEQ ID NO: 18) | METDTLLLWVLLLWVPGSTGERKCCVECPPCPAPELLGGPSV<br>FLFPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVYTLPPSREEMTKNQVSL<br>TCLVKGFYPSDIAVEWESNGQPENNYKTTPPVLDSDGSFFLY<br>SKLTVDKSRWQQGNVFSCSVMHEALHNHYTQKSLSLSPGK. |
| G075<br>(SEQ ID NO: 20) | METDTLLLWVLLLWVPGSTGEPKSCDKTHTCPPCPAPELLGG<br>PSVFLFPPKPKDTLMISRTPEVTCVVVDVSHEDPEVKFNWYV<br>DGVEVHNAKTKPREEQYNATYRVVSVLTVLHQDWLNGKEY<br>KCKVSNKALPAPIEKTISKAKGQPREPQVYTLPPSREEMTKN<br>QVSLTCLVKGFYPSDIAVEWESNGQPENNYKTTPPVLDSDGS<br>FFLYSKLTVDKSRWQQGNVFSCSVMHEALHNHYTQKSLSLS<br>PGKERKCCVECPPCP. |
| G076<br>(SEQ ID NO: 21) | METDTLLLWVLLLWVPGSTGEPKSCDKTHTCPPCPAPELLGG<br>PSVFLFPPKPKDTLMISRTPEVTCVVVDVSHEDPEVKFNWYV<br>DGVEVHNAKTKPREEQYNSTYAVVSVLTVLHQDWLNGKEY<br>KCKVSNKALPAPIEKTISKAKGQPREPQVYTLPPSREEMTKN<br>QVSLTCLVKGFYPSDIAVEWESNGQPENNYKTTPPVLDSDGS<br>FFLYSKLTVDKSRWQQGNVFSCSVMHEALHNHYTQKSLSLS<br>PGKERKCCVECPPCP. |
| G096<br>(SEQ ID NO: 28) | METDTLLLWVLLLWVPGSTGGPPGPPGPPGPPGPPGPPGPPG<br>PPGPPGPPEPKSCDKTHTCPPCPAPELLGGPSVFLFPPKPKDTL<br>MISRTPEVTCVVVDVSHEDPEVKFNWYVDGVEVHNAKTKPR<br>EEQYNSTYRVVSVLTVLHQDWLNGKEYKCKVSNKALPAPIE<br>KTISKAKGQPREPQVYTLPPSREEMTKNQVSLTCLVKGFYPS<br>DIAVEWESNGQPENNYKTTPPVLDSDGSFFLYSKLTVDKSRW<br>QQGNVFSCSVMHEALHNHYTQKSLSLSPGK |
| G098<br>(SEQ ID NO: 24) | METDTLLLWVLLLWVPGSTGEPKSCDKTHTCPPCPAPELLGG<br>PSVFLFPPKPKDTLMISRTPEVTCVVVDVSHEDPEVKFNWYV<br>DGVEVHNAKTKPREEQYNATYRVVSVLTVLHQDWLNGKEY<br>KCKVSNKALPAPIEKTISKAKGQPREPQVYTLPPSREEMTKN<br>QVSLTCLVKGFYPSDIAVEWESNGQPENNYKTTPPVLDSDGS<br>FFLYSKLTVDKSRWQQGNVFSCSVMHEALHNHYTQKSLSLS<br>PGKGPPGPPGPPGPPGPPGPPGPPGPPGPPGPP |
| G089<br>(SEQ ID NO: 27) | METDTLLLWVLLLWVPGSTGEPKSCDKTHTCPPCPAPELLGG<br>PSVFLFPPKPKDTLMISRTPEVTCVVVDVSHEDPEVKFNWYV<br>DGVEVHNAKTKPREEQYNSTYRVVSVLTVLHQDWLNGKEY<br>KCKVSNKALPAPIEKTISKAKGQPREPQVYTLPPSREEMTKN<br>QVSLTCLVKGFYPSDIAVEWESNGQPENNYKTTPPVLDSDGS<br>FFLYSKLTVDKSRWQQGNVFSCSVMHEALHNHYTQKSLSLS<br>PGKGPPGPPGPPGPPGPPGPPGPPGPPGPP |

As a clarifying example, the skilled artisan will understand that the stradomer molecules of the present invention may be constructed by preparing a polynucleotide molecule that encodes various combinations of Fc domain monomers and Fc partial domain monomers, each with or without select point mutations, but with a combination that will form a minimum of two Fc domain monomers. Such a polynucleotide molecule, for example polynucleotides encoding the stradomers of SEQ ID NOs: 4,8, 9, 10 or 18, may be inserted into an expression vector, which can be used to transform a population of bacteria or transfect a population of mammalian cells. Stradomer monomers can then be produced by culturing the transformed bacteria or transfected mammalian cells under appropriate culture conditions. For example, a clonal cell line continuing a pool of stably transfected cells can be achieved by selecting cells with genetecin/G418. Alternatively, cells can be transiently transfected with DNA encoding the stradomer of the current invention, i.e. G045c (SEQ ID NO:4), G019 (SEQ ID NO:8), G028 (SEQ ID NO:9) G046 (SEQ ID NO: 10) or G051 (SEQ ID NO: 18) under the control of the CMV promoter. The expressed stradomer monomers can then form functional stradomers upon either self-aggregation of the stradomer monomers or association of stradomer monomers using inter-stradomer monomer linkages. The expressed stradomers can then be purified from the cell culture media by affinity chromatography using, for example, Protein A or Protein G columns. The present invention encompasses both stradomers formed through the association of stradomer monomers having identical amino acid sequences, stradomer monomers having substantially similar amino acid sequences, or stradomer monomers having dissimilar sequences. In the latter embodiment the amino acid sequence of the stradomer monomers comprising a stradomer need only be of such similarity that two or more functional FcγR binding sites are formed.

Surprisingly, the G045c (SEQ ID NO:4) produced by the methods of the current invention containing the claimed sequences of the leader sequence (SEQ ID NO:1) directly linked to the N terminus of IgG1 Fc (SEQ ID NO:2) which in turn is directly linked via its terminus to the IgG2 hinge multimerization domain (SEQ ID NO:3) leads to higher order multimer formation than was observed with the predecessor molecules containing extraneous sequences not previously thought to be of functional importance, such as restriction sites in the IgG1 Fc monomer, as shown in SEQ ID NOs: 6 and 7. In fact, nearly 74% of the resulting G045c stradomer preparation contains multimers whereas only about 26% of the composition contains monomers. This is in contrast to preparations containing the molecules with the extraneous sequences. These preparations contain only about 27% multimers and 72% of the composition is present as monomers. Furthermore, the higher order multimers produced by the stradomer monomers of SEQ ID NO:4 had surprisingly superior efficacy when compared with the old extraneous sequence containing stradomers previously described. Therefore, in one embodiment of the current invention, the multimerization domain creates high order multimers of the stradomer units. In still a further embodiment, at least about 35% of the resulting stradomer composition contains multimers of the stradomer units. In still a further embodiment, at least about 55% of the resulting stradomer composition contains multimers of the stradomer units. In still a further embodiment, at least about 65% of the resulting stradomer composition contains multimers of the stradomer units. In still a further embodiment, at least about 70% of the resulting stradomer composition contains multimers of the stradomer units. In still a further embodiment, at least about 75% of the resulting stradomer composition contains multimers of the stradomer units.

As indicated above, an Fc domain can be functionally defined by its ability to bind FcRn, DC-SIGN, SIGN-R1 and/or an Fcγ receptor. The compounds of the current invention bind to cognate receptors including, FcγRIIIa, FcγRIIb and/or SIGN-R1 with much higher affinity than IgG2a controls (FIGS. 5 and 6). As a result, the particular amino acid sequence of an Fc domain will vary based on the Fc partial domains that comprise the Fc domain. However, in one embodiment of the present invention the Fc domain comprises the hinge region and a CH2 domain of an immunoglobulin molecule. In a further preferred embodiment the Fc domain comprises the hinge region, a CH2 domain and CH3 domain of an immunoglobulin molecule. In a further embodiment, the Fc domain comprises the hinge region, a CH2 domain, CH3 domain and CH4 domain of an immunoglobulin molecule. In yet another embodiment, the Fc domain comprises the hinge region, a CH2 domain and CH4 domain of an immunoglobulin molecule. In a further preferred embodiment, the Fc domain comprises a CH2 domain and CH3 domain. In a preferred embodiment, the Fc domain contains the hinge, CH2 and CH3 domain of IgG1 (SEQ ID NO:2). In another preferred embodiment, the Fc domain contains the CH2 and CH3 domains of IgG1 (SEQ ID NO: 19).

Inter-Stradomer Monomer Linkage

A separate linkage found in the biomimetic compounds of the present invention is the "inter-stradomer monomer linkage" that occurs between two or more individual stradomer monomers that comprise the stradomers of the present invention. While the domain linkages are short amino acid sequences that serve to link the Fc domain monomers and partial Fc domain monomers that comprise individual stradomer monomers of the biomimetic compounds to each other, the inter-stradomer monomer linkages serve to join two or more individual stradomer monomers that comprise the biomimetic compounds. The inter-stradomer monomer linkage may be any linkage capable of stably associating the individual stradomer monomers. In some embodiments, the inter-stradomer monomer linkage may be a covalent link between the stradomer monomers. Alternatively, the inter-stradomer monomer linkage between stradomer monomers may be by direct chemical cross-linking. In preferred embodiments, the stradomer monomer structures take advantage of the natural self-aggregation properties between Fc domain monomers to create self-aggregating stradomers. In certain of such embodiments, the self-aggregation occurs without covalent disulfide bond linkages normally found in nature. Without being bound by theory, intact IgG1, for example, has 2 cysteine bonds in the hinge region (Dorai H. Role of inter-heavy and light chain disulfide bonds in the effector functions of human immunoglobulin IgG1. Molecular Immunology. 29;12, 1992, 1487-1491; Meulenbroek A J and Zeijlemaker W P. Human IgG Subclasses: Useful diagnostic markers for immunocompetence. ISBN 90-5267-011-0) whereas the IgG1 hinge, IgG1 CH2, and IgG1 CH3 domains of G045 demonstrate no intermonomer linkages; in G045 all intermonomer linkages occur in the C-terminal of the IgG2 hinge domain. In other such embodiments disulfide bonds form between the individual stradomer monomers to form the stradomers. The disulfide bonds form between cysteine residues of the Fc domain monomers that comprise the biomimetic molecules, using either cysteine residues occurring in the natural Fc domain monomer sequence or cysteine residues incorporated into an Fc domain monomer by site-directed mutagenesis. Such natural self-aggregation properties can also be used to form the inter-stradomer monomer linkages between individual stradomer monomers in stradomer multimers. In a preferred embodiment, the cysteine residues that form the inter-stradomer monomer linkage are at positions 236, 237, 240, and 243 of the IgG2 hinge domain of the mature protein of G045. In a preferred embodiment, the cysteine residues that form the inter-stradomer monomer linkage are at positions 4, 5, 8, and 11 of the IgG2 hinge domain of the mature protein of G051. Alternative embodiments include inter-stradomer monomer linkages where disulfide bonds form between cysteine residues introduced through site-directed mutagenesis into the amino acid sequence comprising the individual stradomer monomers.

As discussed above, in a preferred embodiment, the inter-stradomer monomer linkage that forms a stradomer is a linkage that results from self-aggregation of stradomer monomers. In one embodiment, the two stradomer monomers that comprise the stradomer are identical peptides, such that the two individual stradomer monomers that comprise the stradomer are identical in sequence. However, the skilled artisan will understand that other embodiments include stradomers where the stradomer monomers differ from each other in amino acid sequence.

Two stradomer monomers can form a stradomer by, for example, aligning in parallel such that pairing takes place between identical Fc partial domain monomers in the stradomer monomers. However, the present invention also includes embodiments where pairing occurs between non-identical Fc partial domain monomers, and embodiments where pairing occurs between identical Fc partial domain monomers in the stradomer monomers but where the alignment of the two stradomer monomers is offset.

Cluster Stradomer

A "cluster stradomer" is a biomimetic that has a radial form with a central moiety "head" and two or more "legs", wherein each leg comprises one or more Fc domains that is capable of binding at least one Fc gamma receptor, thus creating a biomimetic capable of binding two or more Fc gamma receptors. Each cluster stradomer is comprised of more than one dimeric protein, each called a "cluster stradomer unit." Each cluster stradomer unit is comprised of a region that multimerizes and a "leg" region that comprises at least one functional Fc domain. The multimerizing region creates a cluster stradomer "head" once multimerized with another cluster stradomer unit. The leg region is capable of binding as many Fcγ receptors as there are Fc domains in each leg region. Thus a cluster stradomer is a biomimetic compound capable of binding two or more Fcγ receptors, increasing binding affinity and avidity.

The multimerizing region may be a peptide sequence that causes dimeric proteins to further multimerize or alternatively the multimerizing region may be a glycosylation that enhances the multimerization of dimeric proteins. Examples of peptide multimerizing regions include IgG2 hinge, IgE CH2 domain, isoleucine zipper, collagen Glycine-Proline-Proline repeat ("GPP") and zinc fingers. The influence of glycosylation on peptide multimerization is well described in the art (e.g., Role of Carbohydrate in Multimeric Structure of Factor VIII/V on Willebrand Factor Protein. Harvey R. Gralnick, Sybil B. Williams and Margaret E. Rick. Proceedings of the National Academy of Sciences of the United States of America, Vol. 80, No. 9, [Part 1: Biological Sciences] (May 1, 1983), pp. 2771-277 '4; Multimerization and collagen binding of vitronectin is modulated by its glycosylation. Kimie Asanuma, Fumio Arisaka and Haruko Ogawa. International Congress Series Volume 1223, December 2001, Pages 97-101).

The multimerizing region may be a peptide sequence that causes peptides to dimerize or multimerize and includes the IgG2 hinge, the IgE CH2 domain, an isoleucine zipper, collagen GPP, and a zinc finger. As is known in the art, the hinge region of human IgG2 can form covalent dimers (Yoo, E. M. et al. J. Immunol. 170, 3134-3138 (2003); Salfeld Nature Biotech. 25, 1369-1372 (2007)). The dimer formation of IgG2 is potentially mediated through the IgG2 hinge structure by C—C bonds (Yoo et al 2003), suggesting that the hinge structure alone can mediate dimer formation. The amount of IgG2 dimers found in human serum, however, is limited. It is estimated that the amount of IgG2 existing as a dimer of the homodimer is less than 10% of the total IgG2 (Yoo et al. 2003). Furthermore, there is no quantitative evidence of the multimerization domain of IgG2 beyond the dimer of the homodimer. (Yoo et al. 2003). That is, native IgG2 has not been found to form higher order multimers in human serum. Therefore, the results presented herein are particularly surprising in that the IgG2 hinge-containing stradomers (i.e. G045c, G019 and G051) are present in high order multimers and unlike native IgG2 in human serum in which the IgG2 hinge interactions are variable and dynamic, G045c has been demonstrated to form highly stable multimers evidenced on non-reducing SDS-PAGE gels, by analytical ultracentrifugation and by 3 month stability studies at 100% humidity at 37° C. Furthermore, it is also surprising that the amount of multimers in the IgG2 hinge-containing stradomer preparations are significantly higher than the 10% observed for IgG2 in human serum. For example, the amount of multimers, including dimers of the homodimer in G045c preparations is approximately 67%.

The amino acid sequence of the human IgG2 hinge monomer is as follows: ERKCCVECPPCP (SEQ ID NO: 3). Mutation of any one of the 4 cysteines in SEQ ID 3 may be associated with greatly diminished multimerization of the stradomer. There are two C-X-X-C portions of the IgG2 hinge monomer. Thus, stradomer monomers of the present invention may comprise either the complete 12 amino acid sequence of the IgG2 hinge monomer, or either or both of the four amino acid cores, along with Fc domain monomers. While the X-X of the core structures can be any amino acid, in a preferred embodiment the X-X sequence is V-E or P-P. The skilled artisan will understand that the IgG2 hinge monomer may be comprised of any portion of the hinge sequence in addition to the core four amino acid structure, including all of the IgG2 hinge sequence and some or all of the IgG2 CH2 and CH3 domain monomer sequences. Without being bound by theory, the IgG2 hinge multimerization domain may form multimers by interacting with any portion of the stradomer monomer. That is, the IgG2 hinge of one stradomer monomer may bind the IgG2 hinge of another stradomer monomer, thereby forming a dimer of the homodimer, or higher order multimers while retaining increased functional binding to Fc receptors relative to natural IgG1 Fc. Alternatively, the IgG2 hinge domain of one stradomer monomer may bind the IgG1 hinge of another stradomer monomer, thereby forming a dimer of the homodimer, or higher order multimers while retaining increased functional binding to Fc receptors relative to natural IgG1 Fc. It is also possible that the IgG2 hinge domain of one stradomer monomer binds to another portion of the IgG1 Fc domain, i.e. the CH2 or CH3 domain of another stradomer monomer to form the dimer of the homodimer, or higher order multimers while retaining increased functional binding to Fc receptors relative to natural IgG1 Fc.

Leucine and isoleucine zippers may also be used as the multimerizing region. Leucine and isoleucine zippers (coiled-coil domains) are known to facilitate formation of protein dimers, trimers and tetramers (Harbury et al. Science 262:1401-1407 (1993); O'Shea et al. Science 243:538 (1989)). By taking advantage of the natural tendency of an isoleucine zipper to form a trimer, cluster stradomers may be produced.

While the skilled artisan will understand that different types of leucine and isoleucine zippers may be used, in a preferred embodiment the isoleucine zipper from the GCN4 transcriptional regulator modified as described (Morris et al., Mol. Immunol. 44:3112-3121 (2007); Harbury et 262:1401-1407 al. Science (1993)) is used: GGGSIKQIEDKIEEILS-KIYHIENEIARIKKLIGERGHGGG (SEQ ID NO:5) This isoleucine zipper sequence is only one of several possible sequences that can be used for multimerization of Fc domain monomers. While the entire sequence shown in SEQ ID NO:5 may be used, the underlined portion of the sequence represents the core sequence of the isoleucine zipper that may be used in the cluster stradomers of the present invention. Thus, stradomer monomers of the present invention may comprise either the complete amino acid sequence of the isoleucine zipper, or the 28 amino acid core, along with one or more Fc domain monomers. The skilled artisan will also understand that the isoleucine zipper may be comprised of any portion of the zipper in addition to the core 28 amino acid structure, and thus may be comprised of more than 28 amino acids but less than the entire sequence.

GPP is an amino acid sequence found in human collagen that causes collagen protein: protein binding. While the skilled artisan will understand that different types of GPP repeats may be used as a Multimerization Domain, in a preferred embodiment the Glycine-Proline-Proline repeats as described (Fan et al FASEB Journal 3796 vol 22 2008) is used: (SEQ ID NO:26) This Glycine-Proline-Proline repeat sequence is only one of several possible sequences that can be used for multimerization of Fc domain monomers. While the entire sequence shown in SEQ ID NO:26 may be used, repeats of different length may also possible be used to multimerize Fc domain monomers. Likewise, repeats containing different amino acids within the GPP repeats may also be substituted.

It is understood that the stradomers and other biomimetic molecules disclosed herein can be derived from any of a variety of species. Indeed, Fc domains, or Fc partial domains, in any one biomimetic molecules of the present invention can be derived from immunoglobulin from more than one (e.g., from two, three, four, five, or more) species. However, they will more commonly be derived from a single species. In addition, it will be appreciated that any of the methods disclosed herein (e.g., methods of treatment) can be applied to any species. Generally, the components of a biomimetic applied to a species of interest will all be derived from that species. However, biomimetics in which all the components are of a different species or are from more than one species (including or not including the species to which the relevant method is applied) can also be used.

The specific CH1, CH2, CH3 and CH4 domains and hinge regions that comprise the Fc domains and Fc partial domains of the stradomers and other biomimetics of the present invention may be independently selected, both in terms of the immunoglobulin subclass, as well as in the organism, from which they are derived. Accordingly, the stradomers and other biomimetics disclosed herein may comprise Fc domains and partial Fc domains that independently come from various immunoglobulin types such as human IgG1, IgG2, IgG3, IgG4, IgA1, IgA1, IgD, IgE, and IgM, mouse IgG2a, or dog IgA or IgB. Preferably, for human therapeutics the Fc domains of the current invention are of the human IgG1 isotype. Similarly each Fc domain and partial Fc domain may be derived from various species, preferably a mammalian species, including non-human primates (e.g., monkeys, baboons, and chimpanzees), humans, murine, *rattus*, bovine, equine, feline, canine, porcine, rabbits, goats, deer, sheep, ferrets, gerbils, guinea pigs, hamsters, bats, birds (e.g., chickens, turkeys, and ducks), fish and reptiles to produce species-specific or chimeric stradomer molecules.

The individual Fc domains and partial Fc domains may also be humanized. One of skill in the art will realize that different Fc domains and partial Fc domains will provide different types of functionalities. For example, FcγRs bind specifically to IgG immunoglobulins and not well other classes of immunoglobulins. Thus, one of skill in the art, intending to design a stradomer with multiple Fcγ receptor binding capacity, would design stradomer Fc domains that at least incorporate the well characterized Fcγ receptor binding sequences of IgG, including those in the lower IgG hinge region and/or the IgG CH2 & CH3 domains. One of ordinary skill in the art will also understand various deleterious consequences can be associated with the use of particular Ig domains, such as the anaphylaxis associated with IgA infusions. The biomimetics disclosed herein should generally be designed to avoid such effects, although in particular circumstances such effects may be desirable.

The present invention also encompasses stradomers comprising Fc domains and Fc partial domains having amino acids that differ from the naturally-occurring amino acid sequences of the Fc domain or Fc partial domain. Preferred Fc domains for inclusion in the biomimetic compounds of the present invention have a measurable specific binding affinity to either a holo-Fcγ receptor or a soluble extracellular domain portion of an FcγR. Primary amino acid sequences and X-ray crystallography structures of numerous Fc domains and Fc domain monomers are available in the art. See, e.g., Woof J M, Burton D R. Human antibody-Fc receptor interactions illuminated by crystal structures. Nat Rev Immunol. 2004 February;4(2):89-99. Representative Fc domains with Fcγ receptor binding capacity include the Fc domains from human IgG1 (SEQ ID NO: 2). These native sequences have been subjected to extensive structure-function analysis including site directed mutagenesis mapping of functional sequences. Based on these prior structure-function studies and the available crystallography data, one of skill in the art may design functional Fc domain sequence variants while preserving the Fc domain's FcγR receptor binding capacity. For example, cysteine residues may be added to enhance sulfide bonding between monomers or deleted to alter the interaction between stradomer homodimers.

The amino acid changes may be found throughout the sequence of the Fc domain, or be isolated to particular Fc partial domains that comprise the Fc domain. The functional variants of the Fc domain used in the stradomers and other biomimetics of the present invention will have at least about 50%, 60%, 70%, 80%, 90%, 95%, 96%, 97%, 98% or 99% sequence identity to a native Fc domain. Similarly, the functional variants of the Fc partial domains used in the stradomers and other biomimetics of the present invention will have at least about 50%, 60%, 70%, 80%, 90%, 95%, 96%, 97%, 98% or 99% sequence identity to a native Fc partial domain.

The skilled artisan will appreciate that the present invention further encompasses the use of functional variants of Fc domain monomers in the construction of Fc fragment monomers, Fc partial fragment monomers, stradomer monomers and the other monomers of the present invention. The functional variants of the Fc domain monomers will have at least about 50%, 60%, 70%, 80%, 90%, 95%, 96%, 97%, 98% or 99% sequence identity to a native Fc domain monomer sequence.

Similarly, the present invention also encompasses the use of functional variants of Fc partial domain monomers in the construction of Fc fragment monomers, Fc partial fragment monomers, Fc domains monomers, stradomer monomers and the other monomers of the present invention. The functional variants of the Fc partial domain monomers will have at least about 50%, 60%, 70%, 80%, 90%, 95%, 96%, 97%, 98% or 99% sequence identity to a native Fc partial domain monomer sequence.

The amino acid changes may decrease, increase, or leave unaltered the binding affinity of the stradomer to the Fcγ receptor. Preferably such amino acid changes will be conservative amino acid substitutions, however, such changes include deletions, additions and other substitutions. Conservative amino acid substitutions typically include changes within the following groups: glycine and alanine; valine, isoleucine, and leucine; aspartic acid and glutamic acid; asparagine, glutamine, serine and threonine; lysine, histidine and arginine; and phenylalanine and tyrosine. Additionally, the amino acid change may enhance multimerization strength, for example by the addition of cysteine residues.

The amino acid changes may be naturally occurring amino acid changes resulting in Fc domain polymorphisms, or the amino acid changes may be introduced, for example by site directed mutagenesis. The amino acid changes can occur anywhere within the Fc domain so long as the Fc domain retains its receptor binding function and biological activity. In a preferred embodiment, the polymorphism or mutation leads to enhanced receptor binding and/or enhanced multimerization or biological function. The polymorphism/mutation preferably occurs at one or more of amino acid positions 233-435 according to the EU index as in Kabat et al., Sequences of Proteins of Immunological Interest, 5th Ed. Public Health Service, National Institutes of Health, Bethesda, MD (1991). Specific polymorphisms/mutations in these amino acid positions are well known in the art and can be found, for example in Shields, et al. (2001) "High Resolution Mapping of the Binding Site on Human IgG1 for FcγR1, FcγRII, FcγRIII and FcRn and Design of IgG1 Variants with Improved Binding to the FcγR," J. Biol. Chem., 276(9):6591-6601, which is herein incorporated by reference in its entirety.

In a preferred embodiment, the polymorphism/mutation contains one or more amino acid substitutions of positions 233, 234, 235, 236, 237, 238, 239, 253, 254, 255, 256, 258, 264, 265, 267, 268, 269, 270, 272, 276, 280, 285, 286, 288, 290, 293, 295, 296, 297, 298, 301, 303, 305, 307, 309, 311, 312, 315, 317, 322, 326, 327, 329, 330, 331, 332, 333, 334, 337, 338, 339, 360, 362, 376, 378, 380, 382, 392, 414, 415, 424, 430, 433, 434, 435, and/or 436 of IgG1 Fc. In a further embodiment, the polymorphism/mutation contains two or more amino acid substitutions of positions 233, 234, 235, 236, 237, 238, 239, 253, 254, 255, 256, 258, 264, 265, 267, 268, 269, 270, 272, 276, 280, 285, 286, 288, 290, 293, 295, 296, 297, 298, 301, 303, 305, 307, 309, 311, 312, 315, 317, 322, 326, 327, 329, 330, 331, 332, 333, 334, 337, 338, 339, 360, 362, 376, 378, 380, 382, 392, 414, 415, 424, 430, 433, 434, 435, and/or 436 of IgG1 Fc. In a further embodiment, the polymorphism/mutation contains three or more amino acid substitutions of positions 233, 234, 235, 236, 237, 238, 239, 253, 254, 255, 256, 258, 264, 265, 267, 268, 269, 270, 272, 276, 280, 285, 286, 288, 290, 293, 295, 296, 297, 298, 301, 303, 305, 307, 309, 311, 312, 315, 317, 322, 326, 327, 329, 330, 331, 332, 333, 334, 337, 338, 339, 360, 362, 376, 378, 380, 382, 392, 414, 415, 424, 430, 433, 434, 435, and/or 436 of IgG1 Fc. In a further embodiment, the polymorphism/mutation contains more than three amino acid substitutions of positions 233, 234, 235, 236, 237, 238, 239, 253, 254, 255, 256, 258, 264, 265, 267, 268, 269, 270, 272, 276, 280, 285, 286, 288, 290, 293, 295, 296, 297, 298, 301, 303, 305, 307, 309, 311, 312, 315, 317, 322, 326, 327, 329, 330, 331, 332, 333, 334, 337, 338, 339, 360, 362, 376, 378, 380, 382, 392, 414, 415, 424, 430, 433, 434, 435, and/or 436 of IgG1 Fc.

The term "functional variant" as used herein refers to a sequence related by homology to a reference sequence which is capable of mediating the same biological effects as the reference sequence (when a polypeptide), or which encodes a polypeptide that is capable of mediating the same biological effects as a polypeptide encoded by the reference sequence (when a polynucleotide). For example, a functional variant of any of the biomimetics herein described would have a specified homology or identity and would be capable of immune modulation of monocytes or DCs. Functional sequence variants include both polynucleotides and polypeptides. Sequence identity is assessed generally using BLAST 2.0 (Basic Local Alignment Search Tool), operating with the default parameters: Filter—On, Scoring Matrix—BLOSUM62, Word Size—3, E value—10, Gap Costs—11,1 and Alignments—50.

From the above, it will be appreciated that stradomers of the present invention include stradomers having: (a) only naturally occurring Fc domains; (b) a mixture of naturally occurring Fc domains and Fc domains with altered amino acid sequences; and (c) only Fc domains with altered amino acid sequences. All that is required is that stradomers containing altered amino acid sequences have at least 25%; 30%; 40%; 50%; 60%; 70%; 80%; 90%; 95%; 96%; 97%; 98%; 99%; 99.5%; or 100% or even more of the ability of a corresponding stradomer comprising Fc domains with naturally-occurring sequences to bind to two or more FcγR receptors.

The aforementioned Fcγ receptor binding sites occurring in the stradomers of the present invention may be altered in sequence through genetic engineering to predictably derive binding sites with altered binding capabilities and affinities relative to a native sequence. For example, specific residues may be altered that reduce Fc domain binding of the biomimetic compounds to FcγRIIb while increasing binding to FcγRIIIa. An example of an extensive mutagenesis based structure-function analysis for hIgG Fcγ receptor binding sequences is Robert L. Shields, et al. High Resolution Mapping of the Binding Site on Human IgG1 for FcγR1, FcγRII, FcγRIII, and FcRn and Design of IgG1 Variants with Improved Binding to the FcγR. J. Biol. Chem., Feb 2001; 276: 6591-6604. Similar studies have been performed on murine IgG Fc (mIgG Fc). Based on the structural and primary sequence homologies of native IgG Fc domains across species, one of skill in the art may translate the extensive structure-function knowledge of human IgG Fc and mouse IgG Fc to rational mutagenesis of all native Fcγ receptor binding site sequences in the biomimetic compounds of the present invention to design binding sites with particular Fcγ receptor specificities and binding affinities.

In addition to the amino acid sequence composition of native Fc domains, the carbohydrate content of the Fc domain is known to play an important role on Fc domain structure and binding interactions with FcγR. See, e.g., Robert L. Shields, et al. Lack of Fucose on Human IgG1 N-Linked Oligosaccharide Improves Binding to Human FcγRIII and Antibody-dependent Cellular Toxicity. J. Biol. Chem., Jul 2002; 277: 26733-26740 (doi:10.1074/jbc.M202069200); Ann Wright and Sherie L. Morrison. Effect of C2-Associated Carbohydrate Structure on Ig Effector Function: Studies with Chimeric Mouse-Human IgG1 Antibodies in Glycosylation Mutants of Chinese Hamster Ovary Cells. J. Immunol, Apr 1998; 160: 3393-3402. Carbohydrate content may be controlled using, for example, particular protein expression systems including particular cell lines or in vitro enzymatic modification. Thus, the present invention includes stradomers comprising Fc domains with the native carbohydrate content of holo-antibody from which the domains were obtained, as well as those biomimetic compounds with an altered carbohydrate content. In another embodiment, multimer components of the stradomer are characterized by a different glycosylation pattern compared with the homodimer component of the same stradomer. In a preferred embodiment, the stradomer is enriched for multimers comprising a glycosylation pattern that enhances Fc receptor binding.

The addition to the polypeptide chain of an Fc partial domain, a multimerization region, or glycosylation changes may create a conformational change in the Fc domain permitting enhanced binding of the Fc domain to an Fcγ receptor. Thus, seemingly very minor changes to the polypeptide may also create a stradomer capable of enhanced binding of multiple Fcγ receptors or a stradomer with decreased ability to bind multiple Fcγ receptors.

Partial Domains and Partial Fragments

The skilled artisan will further recognize that the Fc domains and Fc partial domains used in the embodiments of the present invention need not be full-length versions. That is, the present invention encompasses the use of Fc domain monomers and Fc partial domain monomers lacking amino acids from the amino terminus, carboxy terminus or middle of the particular Fc domain monomers and Fc partial domain monomers that comprise the stradomers and other biomimetics of the present invention.

For example, the binding site on human IgG immunoglobulins for Fcγ receptors has been described (e.g. Radaev, S., Sun, P., 2001. Recognition of Immunoglobulins by Fcγ Receptors. Molecular Immunology 38, 1073-1083; Shields, R. L. et. al., 2001. High Resolution Mapping of the Binding Site on Human IgG1 for FcγR1, FcγRII, FcγRIII, and FcRn and Design of IgG1 Variants with Improved Binding to the FcγR. J. Biol. Chem. 276 (9), 6591-6604). Based on that knowledge, one may remove amino acids from the Fc domain of these immunoglobulins and determine the effects on the binding interaction between the Fc domain and the receptor. Thus, the present invention encompasses IgG Fc domains having at least about 90% of the amino acids encompasses positions 233 through 338 of the lower hinge and CH2 as defined in Radaev, S., Sun, P., 2001.

Fc partial domains of IgG immunoglobulins of the present invention include all or part of the hinge region, all or part of the CH2 domain, and all or part of the CH3 domain.

The IgG Fc partial domains having only a part of the hinge region, part of the CH2 domain or part of the CH3 domain are constructed from Fc partial domain monomers. Thus, the present invention includes IgG hinge region monomers derived from the N-terminus of the hinge region or the C-terminus of the hinge region. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 (up to 15 for IgG1, up to 12 for IgG2, up to 62 for IgG3, up to 12 for IgG4) amino acids of the hinge region.

The present invention also includes IgG CH2 domain monomers derived from the N-terminus of the CH2 domain or the C-terminus of the CH2 domain. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 (up to 110 for IgG1 and IgG3, up to 109 for IgG2 and IgG4) amino acids of the CH2 domain.

The present invention further includes IgG CH3 domain monomers derived from the N-terminus of the CH3 domain or the C-terminus of the CH3 domain. They can thus contain, for example, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, or 107 (up to 106 for IgG1 and IgG3, up to 107 for IgG2 and IgG4) amino acids of the CH3 domain.

From the above, it will be appreciated that different embodiments of the present invention include stradomers containing: (a) full-length Fc domains; (b) a mixture of full-length Fc domains and Fc partial domains; and (c) Fc partial domains. In each of these embodiments, the stradomers may further comprise CH1 domains. As discussed herein, in each embodiment of the stradomers of the present invention, the stradomers have the ability to bind two or more Fcγ receptors.

Preferred Embodiments of Stradomers and Stradomer Monomers

The terms "FcγR" and "Fcγ receptor" as used herein includes each member of the Fc gamma receptor family of proteins expressed on immune cell surfaces as described in Nimmerjahn F and Ravetch J V. Fcγ receptors: old friends and new family members. Immunity. 2006 Jan; 24(1): 19-28, or as may later be defined. It is intended that the term "FcγR" herein described encompasses all members of the Fc gamma R1, RII, and RIII families. Fcγ receptor includes low affinity and high affinity Fcγ receptors, including but not limited in humans to FcγR1 (CD64); FcγRII (CD32) and its isotypes and allotypes FcγRIIa LR, FcγRIIa HR, FcγRIIb, and FcγRIIc; FcγRIII (CD 16) and its isotypes FcγRIIIa and FcγRIIIb. A skilled artisan will recognize that the present invention, which includes compounds that bind to FcγR and FcγR homologues such as those described in Davis, et al. (2004) "Differential B cell expression of mouse Fc receptor homologs," Int. Immunol., 16(9): 1343-1353, will apply to future FcγRs and associated isotypes and allotypes that may not yet have been discovered.

It has been described that hIVIG binds to and fully saturates the neonatal Fc receptor ("FcRn") and that such competitive inhibition of FcRn may play an important role in the biological activity of hIVIG (e.g. Mechanisms of Intravenous Immunoglobulin Action in Immune Thrombocytopeniaurpura. F. Jin, J. Balthasar. Human Immunology, 2005, Volume 66, Issue 4, Pages 403-410.) Since immunoglobulins that bind strongly to Fcγ receptors also bind at least to some degree to FcRn, a skilled artisan will recognize that stradomers which are capable of binding to more than one Fcγ receptor will also bind to and may fully saturate the FcRn.

"Capable of specifically binding to a FcγRx" as used herein refers to binding to an FcγR, such as FcγRIII. Specific binding is generally defined as the amount of labeled ligand which is displaceable by a subsequent excess of unlabeled ligand in a binding assay. However, this does not exclude other means of assessing specific binding which are well established in the art (e.g., Mendel C M, Mendel D B, 'Non-specific' binding. The problem, and a solution. Biochem J. 1985 May 15;228(1):269-72). Specific binding may be measured in a variety of ways well known in the art such as surface plasmon resonance (SPR) technology (commercially available through BIACORE®) or biolayer interferometry (commercially available through ForteBio®) to characterize both association and dissociation constants of the immunologically active biomimetics (Asian K, Lakowicz J R, Geddes C. Plasmon light scattering in biology and medicine: new sensing approaches, visions and perspectives. Current Opinion in Chemical Biology 2005, 9:538-544).

"Immunological activity of aggregated native IgG" refers to the properties of multimerized IgG which impact the functioning of an immune system upon exposure of the immune system to the IgG aggregates. Specific properties of native multimerized IgG includes altered specific binding to FcγRs, cross-linking of FcγRs on the surfaces of immune cells, or an effector functionality of multimerized IgG such as antibody dependent cell-mediated cytotoxicity (ADCC), phagocytosis (ADCP), or complement fixation (See, e.g., Nimmerjahn F, Ravetch J V. The anti-inflammatory activity of IgG: the intravenous IgG paradox. J Exp Med. 2007; 204:11-15; Augener W, Friedman B, Brittinger G. Are aggregates of IgG the effective part of high-dose immunoglobulin therapy in adult idiopathic thrombocytopenia purpura (ITP)? Blut. 1985; 50:249-252; Arase N, Arase H, Park S Y, Ohno H, Ra C, Saito T. Association with FcRgamma is essential for activation signal through NKR-PI (CD161) in natural killer (NK) cells and NK1.1+ T cells. J Exp Med. 1997; 186: 1957-1963; Teeling J L, Jansen-Hendriks T, Kuijpers T W, et al. Therapeutic efficacy of intravenous immunoglobulin G preparations depends on the immunoglobulin G dimers: studies in experimental immune thrombocytopenia. Blood. 2001;98: 1095-1099; Anderson C F, Mosser D M. Cutting edge: biasing immune responses by directing antigen to macrophage Fc gamma receptors. J Immunol. 2002; 168:3697-3701; Jefferis R, Lund J. Interaction sites on human IgG-Fc for FcγR: current models. Immunology Letters. 2002; 82:57; Banki Z, Kacani L, Mullauer B, et al. Cross-Linking of CD32 Induces Maturation of Human Monocyte—Derived Dendritic Cells Via NF-{kappa} B Signaling Pathway. J Immunol. 2003; 170: 3963-3970; Siragam V, Brine D, Crow A R, Song S, Freedman J, Lazarus A H. Can antibodies with specificity for soluble antigens mimic the therapeutic effects of intravenous IgG in the treatment of autoimmune disease? J Clin Invest. 2005;1 15:155-160). These properties are generally evaluated by comparison to the properties of homodimeric IgG.

"Comparable to or superior to an Fcγ receptor cross-linking or an effector functionality of a plurality of naturally-occurring, aggregated IgG immunoglobulins" as used herein means the stradomer generates an Fcγ receptor cross-linking assay value of about 70% or more of the value achieved using a similar dose or concentration of hIVIG. In some embodiments, the assay value is at least within the standard error range of the assay values achieved using hIVIG. In other embodiments, the assay value is 110% or higher than that of hIVIG at the same dose. Assays for Fcγ cross-linking are well known to those of ordinary skill in the art (see e.g., Nimmerjahn and Ravetch, (2008) "Fcγ receptors as regulators of immune responses," Nature Reviews Immunology, 8:34-47).

While higher order multimers have been found to be effective in modulating the immune response, we surprisingly found that homodimers were also effective immune modulators. Without being bound by theory, it is believed that homodimers are able to form higher ordered multimers in vivo. We have found through multimerization experiments that an otherwise pure population of homodimers is able to multimerize in the presence of low levels of blood or fetal bovine serum. Therefore, while higher ordered multimers are more effective than the homodimer fraction in modulating the immune response, the homodimer fraction of the naturally linked stradomers of the current invention may also be effective immune modulators, in part through multimerization of the homodimer in the presence of low levels of blood or serum. Therefore, by "higher order multimers" we mean multimers beyond the homodimer that are formed in solution prior to injection into a subject as well as multimers beyond the homodimer that are formed in vivo.

"Immune modulating activities," "modulating immune response," "modulating the immune system," and "immune modulation" mean altering immune systems by changing the activities, capacities, and relative numbers of one or more immune cells, including maturation of a cell type within its cell type or into other cell types. For example, immune modulation of immature monocytes may lead to greater populations of more mature monocytes, dendritic cells, macrophages, or osteoclasts, all of which are derived from immature monocytes. As another example, immune modulation of memory B cells may lead to selective apoptosis of certain memory B cells with concomitant decreases in production of particular antibodies. As another example, immune modulation of NK cells may lead to enhanced Antibody Dependent Cell Cytotoxicity. As another example, immune modulating activities may lead to increased populations of cells with phenotypes that may otherwise not be expressed at high levels, such as CD8 beta+/CD11c+ cells. As another example, immune modulating activities may lead to decreases of proinflammatory cytokines or cytokines that are commonly elevated in autoimmune diseases such as IL-6 and IL-8. As another example, immune modulating activities may lead to activation of NKT cells with subsequent secretion and cleavage of TGF-beta. For example, immune cell receptors may be bound by immunologically active biomimetics and activate intracellular signaling to induce various immune cell changes, referred to separately as "activating immune modulation." Blockading immune cell receptors to prevent receptor activation is also encompassed within "immune modulation" and may be separately referred to as "inhibitory immune modulation."

Modulation of dendritic cells may promote or inhibit antigen presentation to T cells for example by the induction of expression of CD86 and/or CD1a on the surface of dendritic cells. CD1a is an MHC-class I-related glycoprotein that is expressed on the surface of antigen presenting cells, particularly dendritic cells. CD1a is involved in the presentation of lipid antigens to T cells. CD86 is also expressed on the surface of antigen presenting cells and provides costimulation to T cells. CD86 is a ligand to both CD28 and CTLA-4 on the surface of T cells to send activating and inhibitory signals, respectively. Therefore, the level of expression of CD86 and its cognate receptors, determines whether tolerance or a specific immune response will be induced. In a preferred embodiment, the stradomers of the current invention are capable of modulating the immune response, in part by inducing the expression of CD86 and CD1a on the surface of antigen presenting cells, particularly dendritic cells.

Modulation of maturation of a monocyte refers to the differentiation of a monocyte into a mature DC, a macrophage, or an osteoclast. Differentiation may be modulated to accelerate the rate or direction of maturation and/or to increase the number of monocytes undergoing differentiation. Alternatively, differentiation may be reduced in terms of rate of differentiation and/or number of cells undergoing differentiation.

The term "isolated" polypeptide or peptide as used herein refers to a polypeptide or a peptide which either has no naturally-occurring counterpart or has been separated or purified from components which naturally accompany it, e.g., in tissues such as pancreas, liver, spleen, ovary, testis, muscle, joint tissue, neural tissue, gastrointestinal tissue, or breast tissue or tumor tissue (e.g., breast cancer tissue), or body fluids such as blood, serum, or urine. Typically, the polypeptide or peptide is considered "isolated" when it is at least 70%, by dry weight, free from the proteins and other naturally-occurring organic molecules with which it is naturally associated. Preferably, a preparation of a polypeptide (or peptide) of the invention is at least 80%, more preferably at least 90%, and most preferably at least 99%, by dry weight, the polypeptide (peptide), respectively, of the invention. Since a polypeptide or peptide that is chemically synthesized is, by its nature, separated from the components that naturally accompany it, the synthetic polypeptide or peptide is "isolated."

An isolated polypeptide (or peptide) of the invention can be obtained, for example, by extraction from a natural source (e.g., from tissues or bodily fluids); by expression of a recombinant nucleic acid encoding the polypeptide or peptide; or by chemical synthesis. A polypeptide or peptide that is produced in a cellular system different from the source from which it naturally originates is "isolated," because it will necessarily be free of components which naturally accompany it. In a preferred embodiment, the isolated polypeptide of the current invention contains only the sequences corresponding to the leader peptide (SEQ ID NO:1), the IgG1 Fc monomer (SEQ ID NO:2) or (SEQ ID NO:19) and the IgG2 hinge multimerization domain (SEQ ID NO:3), the isoleucine multimerization domain (SEQ ID NO:5) or the GPP multimerization domain (SEQ ID NO:26) and no further sequences that may aid in the cloning or purification of the protein (i.e. introduced restriction enzyme recognition sites or purification tags). The degree of isolation or purity can be measured by any appropriate method, e.g., column chromatography, polyacrylamide gel electrophoresis, or HPLC analysis.

Pharmaceutical Compositions

Administration of the stradomer compositions described herein will be via any common route, orally, parenterally, or topically. Exemplary routes include, but are not limited to oral, nasal, buccal, rectal, vaginal, ophthalmic, subcutaneous, intramuscular, intraperitoneal, intravenous, intraarterial, intratumoral, spinal, intrathecal, intra-articular, intra-arterial, sub-arachnoid, sublingual, oral mucosal, bronchial, lymphatic, intra-uterine, subcutaneous, intratumor, integrated on an implantable device such as a suture or in an implantable device such as an implantable polymer, intradural, intracortical, or dermal. Such compositions would normally be administered as pharmaceutically acceptable compositions as described herein. In a preferred embodiment the isolated stradomer is administered intravenously or subcutaneously.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The stradomer compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Sterile injectable solutions are prepared by incorporating the stradomer in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Further, one embodiment is a stradomer composition suitable for oral administration and is provided in a pharmaceutically acceptable carrier with or without an inert diluent. The carrier should be assimilable or edible and includes liquid, semi-solid, i.e., pastes, or solid carriers. Except insofar as any conventional media, agent, diluent or carrier is detrimental to the recipient or to the therapeutic effectiveness of a stradomer preparation contained therein, its use in an orally administrable a stradomer composition for use in practicing the methods of the present invention is appropriate. Examples of carriers or diluents include fats, oils, water, saline solutions, lipids, liposomes, resins, binders, fillers and the like, or combinations thereof. The term "oral administration" as used herein includes oral, buccal, enteral or intragastric administration.

In one embodiment, the stradomer composition is combined with the carrier in any convenient and practical manner, i.e., by solution, suspension, emulsification, admixture, encapsulation, microencapsulation, absorption and the like. Such procedures are routine for those skilled in the art.

In a specific embodiment, the stradomer composition in powder form is combined or mixed thoroughly with a semi-solid or solid carrier. The mixing can be carried out in any convenient manner such as grinding. Stabilizing agents can be also added in the mixing process in order to protect the composition from loss of therapeutic activity through, i.e., denaturation in the stomach. Examples of stabilizers for use in an orally administrable composition include buffers, antagonists to the secretion of stomach acids, amino acids such as glycine and lysine, carbohydrates such as dextrose, mannose, galactose, fructose, lactose, sucrose, maltose, sorbitol, mannitol, etc., proteolytic enzyme inhibitors, and the like. More preferably, for an orally administered composition, the stabilizer can also include antagonists to the secretion of stomach acids.

Further, the stradomer composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, i.e., U.S. Pat. No. 5,629,001. Upon reaching the small intestines, the basic pH therein dissolves the coating and permits the composition to be released to interact with intestinal cells, e.g., Peyer's patch M cells.

In another embodiment, the stradomer composition in powder form is combined or mixed thoroughly with materials that create a nanoparticle encapsulating the immunologically active biomimetic or to which the immunologically active biomimetic is attached. Each nanoparticle will have a size of less than or equal to 100 microns. The nanoparticle may have mucoadhesive properties that allow for gastrointestinal absorption of an immunologically active biomimetic that would otherwise not be orally bioavailable.

In another embodiment, a powdered composition is combined with a liquid carrier such as, i.e., water or a saline solution, with or without a stabilizing agent.

A specific stradomer formulation that may be used is a solution of immunologically active biomimetic protein in a hypotonic phosphate based buffer that is free of potassium where the composition of the buffer is as follows: 6 mM sodium phosphate monobasic monohydrate, 9 mM sodium phosphate dibasic heptahydrate, 50 mM sodium chloride, pH 7.0.+/−0.1. The concentration of immunologically active biomimetic protein in a hypotonic buffer may range from 10 microgram/ml to 100 milligram/ml. This formulation may be administered via any route of administration, for example, but not limited to intravenous administration.

Further, a stradomer composition for topical administration which is combined with a semi-solid carrier can be further formulated into a cream or gel ointment. A preferred carrier for the formation of a gel ointment is a gel polymer. Preferred polymers that are used to manufacture a gel composition of the present invention include, but are not limited to carbopol, carboxymethyl-cellulose, and pluronic polymers. Specifically, a powdered Fc multimer composition is combined with an aqueous gel containing an polymerization agent such as Carbopol 980 at strengths between 0.5% and 5% wt/volume for application to the skin for treatment of disease on or beneath the skin. The term "topical administration" as used herein includes application to a dermal, epidermal, subcutaneous or mucosal surface.

Further, a stradomer composition can be formulated into a polymer for subcutaneous or subdermal implantation. A preferred formulation for the implantable drug-infused polymer is an agent Generally Regarded as Safe and may include, for example, cross-linked dextran (Samantha Hart, Master of Science Thesis, "Elution of Antibiotics from a Novel Cross-Linked Dextran Gel: Quantification" Virginial Polytechnic Institute and State University, Jun. 8, 2009) dextran-tyramine (Jin, et al. (2010) Tissue Eng. Part A. 16(8):2429-40), dextran-polyethylene glycol (Jukes, et al. (2010) Tissue Eng. Part A., 16(2):565-73), or dextran-gluteraldehyde (Brondsted, et al. (1998) J. Controlled Release, 53:7-13). One skilled in the art will know that many similar polymers and hydrogels can be formed incorporating the stradomer fixed within the polymer or hydrogel and controlling the pore size to the desired diameter.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Center for Biologics Evaluation and Research standards.

The route of administration will vary, naturally, with the location and nature of the disease being treated, and may include, for example intradermal, transdermal, subdermal, parenteral, nasal, intravenous, intramuscular, intranasal, subcutaneous, percutaneous, intratracheal, intraperitoneal, intratumoral, perfusion, lavage, direct injection, and oral administration.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intratumoral, intraocular, nasal or intraarticular administration.

Figure 3:
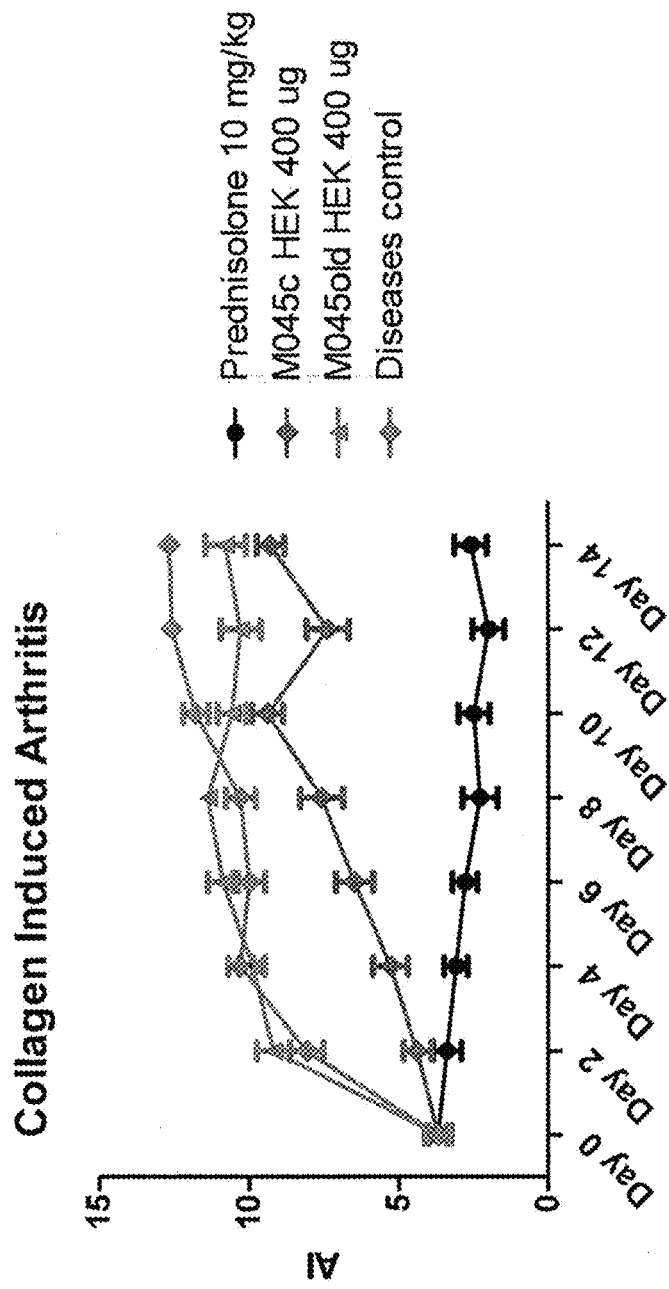
FIG. 3 shows the greater effect of the direct naturally linked stradomers (M045c) of the current invention compared with that of previously stradomer compound containing the extraneous sequences (M045old) on the severity of collagen induced arthritis.

In addition, the stradomer of the current invention may optionally be administered before, during or after another pharmaceutical agent. For example, it has been surprisingly found that concomitant administration of the stradomer of the current invention and prednisolone achieve synergistically superior results than that observed with either the stradomer composition or the prednisolone alone (See FIG. 3).

Below are specific examples of various pharmaceutical formulation categories and preferred routes of administration, as indicated, for specific exemplary diseases:

Buccal or sub-lingual dissolvable tablet: angina, polyarteritis nodosa.

Intravenous: Idiopathic Thrombocytopenia Purpura, Inclusion Body Myositis, Paraproteinemic IgM demyelinating Polyneuropathy, Necrotizing fasciitis, *Pemphigus*, Gangrene, Dermatomyositis, Granuloma, Lymphoma, Sepsis, Aplastic anemia, Multisystem organ failure, Multiple Myeloma and Monoclonal Gammopathy of Unknown Significance, Chronic Inflammatory Demyelinating Polyradiculoneuropathy, Inflammatory Myopathies, Thrombotic thrombocytopeniaurpura, Myositis, Anemia, Neoplasia, Hemolytic anemia, Encephalitis, Myelitis, Myelopathy especially associated with Human T-cell lymphotropic virus-1, Leukemia, Multiple sclerosis and optic neuritis, Asthma, Epidermal necrolysis, Lambert-Eaton myasthenic syndrome, Myasthenia *gravis*, Neuropathy, Uveitis, Guillain-Barré syndrome, Graft Versus Host Disease, Stiff Man Syndrome, Paraneoplastic cerebellar degeneration with anti-Yo antibodies, paraneoplastic encephalomyelitis and sensory neuropathy with anti-Hu antibodies, systemic vasculitis, Systemic Lupus Erythematosus, autoimmune diabetic neuropathy, acute idiopathic dysautonomic neuropathy, Vogt-Koyanagi-Harada Syndrome, Multifocal Motor Neuropathy, Lower Motor Neuron Syndrome associated with anti-/GM1, Demyelination, Membranoproliferative glomerulonephritis, Cardiomyopathy, Kawasaki's disease, Rheumatoid arthritis, and Evan's syndrome IM-ITP, CIDP, MS, dermatomyositis, mysasthenia *gravis*, muscular dystrophy. The term "intravenous administration" as used herein includes all techniques to deliver a compound or composition of the present invention to the systemic circulation via an intravenous injection or infusion.

Dermal gel, lotion, cream or patch: *vitiligo, Herpes zoster*, acne, chelitis.

Rectal suppository, gel, or infusion: ulcerative colitis, hemorrhoidal inflammation.

Oral as pill, troche, encapsulated, or with enteric coating: Crohn's disease, celiac sprue, irritable bowel syndrome, inflammatory liver disease, Barrett's esophagus.

Intra-cortical: epilepsy, Alzheimer's, multiple sclerosis, Parkinson's Disease, Huntingdon's Disease.

Intra-abdominal infusion or implant: endometriosis.

Intra-vaginal gel or suppository: bacterial, trichomonal, or fungal vaginitis. Medical devices: coated on coronary artery stent, prosthetic joints.

The stradomers described herein may be administered in dosages from about 0.01 mg per kg to about 300 mg per kg body weight, and especially from 0.01 mg per kg body weight to about 1000 mg per kg body weight, and may be administered at least once daily, weekly, biweekly or monthly. A biphasic dosage regimen may be used wherein the first dosage phase comprises about 0.1% to about 300% of the second dosage phase.

Therapeutic Applications of Stradomers

Based on rational design and in vitro and in vivo validations, the stradomers of the present invention will serve as important biopharmaceuticals for treating autoimmune diseases and for modulating immune function in a variety of other contexts such as bioimmunotherapy for cancer and inflammatory diseases. Medical conditions suitable for treatment with the immunologically active biomimetics described herein include those currently routinely treated with hIVIG or in which hIVIG has been found to be clinically useful such as autoimmune cytopenias, chronic inflammatory demyelinating polyneuropathy, Guillain-Barre' syndrome, myasthenia *gravis*, anti-Factor VIII autoimmune disease, dermatomyositis, vasculitis, and uveitis (See, F. G. van der Meche, P. I. Schmitz, N. Engl. J. Med. 326, 1123 (1992); P. Gajdos et al, Lancet i, 406 (1984); Y. Sultan, M. D. Kazatchkine, P. Maisonneuve, U. E. Nydegger, Lancet ii, 765 (1984); M. C. Dalakas et al., N. Engl. J. Med. 329, 1993 (1993); D. R. Jayne, M. J. Davies, C. J. Fox, C. M. Black, C. M. Lockwood, Lancet 337, 1137 (1991); P. LeHoang, N. Cassoux, F. George, N. Kullmann, M. D. Kazatchkine, Ocul. Immunol. Inflamm. 8, 49 (2000)) and those cancers or inflammatory disease conditions in which a monoclonal antibody may be used or is already in clinical use. Conditions included among those that may be effectively treated by the compounds that are the subject of this invention include an inflammatory disease with an imbalance in cytokine networks, an autoimmune disorder mediated by pathogenic autoantibodies or autoaggressive T cells, or an acute or chronic phase of a chronic relapsing autoimmune, inflammatory, or infectious disease or process.

In addition, other medical conditions having an inflammatory component will benefit from treatment with stradomers such as Amyotrophic Lateral Sclerosis, Huntington's Disease, Alzheimer's Disease, Parkinson's Disease, Myocardial Infarction, Stroke, Hepatitis B, Hepatitis C, Human Immunodeficiency Virus associated inflammation, adrenoleukodystrophy, and epileptic disorders especially those believed to be associated with postviral encephalitis including Rasmussen Syndrome, West Syndrome, and Lennox-Gastaut Syndrome.

The general approach to therapy using the isolated stradomers described herein is to administer to a subject having a disease or condition, a therapeutically effective amount of the isolated immunologically active biomimetic to effect a treatment. In some embodiments, diseases or conditions may be broadly categorized as inflammatory diseases with an imbalance in cytokine networks, an autoimmune disorder mediated by pathogenic autoantibodies or autoaggressive T cells, or an acute or chronic phase of a chronic relapsing disease or process.

The term "treating" and "treatment" as used herein refers to administering to a subject a therapeutically effective amount of a stradomer of the present invention so that the subject has an improvement in a disease or condition, or a symptom of the disease or condition. The improvement is any improvement or remediation of the disease or condition, or symptom of the disease or condition. The improvement is an observable or measurable improvement, or may be an improvement in the general feeling of well-being of the subject. Thus, one of skill in the art realizes that a treatment may improve the disease condition, but may not be a complete cure for the disease. Specifically, improvements in subjects may include one or more of: decreased inflammation; decreased inflammatory laboratory markers such as C-reactive protein; decreased autoimmunity as evidenced by one or more of: improvements in autoimmune markers such as autoantibodies or in platelet count, white cell count, or red cell count, decreased rash or purpura, decrease in weakness, numbness, or tingling, increased glucose levels in patients with hyperglycemia, decreased joint pain, inflammation, swelling, or degradation, decrease in cramping and diarrhea frequency and volume, decreased angina, decreased tissue inflammation, or decrease in seizure frequency; decreases in cancer tumor burden, increased time to tumor progression, decreased cancer pain, increased survival or improvements in the quality of life; or delay of progression or improvement of osteoporosis.

The term "therapeutically effective amount" as used herein refers to an amount that results in an improvement or remediation of the symptoms of the disease or condition.

As used herein, "prophylaxis" can mean complete prevention of the symptoms of a disease, a delay in onset of the symptoms of a disease, or a lessening in the severity of subsequently developed disease symptoms.

The term "subject" as used herein, is taken to mean any mammalian subject to which stradomers of the present invention are administered according to the methods described herein. In a specific embodiment, the methods of the present disclosure are employed to treat a human subject. The methods of the present disclosure may also be employed to treat non-human primates (e.g., monkeys, baboons, and chimpanzees), mice, rats, bovines, horses, cats, dogs, pigs, rabbits, goats, deer, sheep, ferrets, gerbils, guinea pigs, hamsters, bats, birds (e.g., chickens, turkeys, and ducks), fish and reptiles to produce species-specific or chimeric stradomer molecules.

In particular, the stradomers of the present invention may be used to treat conditions including but not limited to congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; multiple myeloma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; osteolytic bone cancers, lung cancer, kidney cancer and rectal cancer; bone metastasis, bone pain management, and humoral malignant hypercalcemia, ankylosing spondylitis and other spondyloarthropathies; transplantation rejection, viral infections, hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, tumors of the vascular system (angiosarcoma and hemangiopericytoma)) or other cancer.

"Cancer" herein refers to or describes the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, lymphangiosarcoma, lymphangioendotheliosarcoma, leiomyosarcoma, rhabdomyosarcoma, fibrosarcoma, myxosarcoma, chondrosarcoma), neuroendocrine tumors, mesothelioma, chordoma, synovioma, schwanoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwanoma, and other carcinomas, as well as head and neck cancer.

The stradomers of the present invention may be used to treat autoimmune diseases. The term "autoimmune disease" as used herein refers to a varied group of more than 80 diseases and conditions. In all of these diseases and conditions, the underlying problem is that the body's immune system attacks the body itself. Autoimmune diseases affect all major body systems including connective tissue, nerves, muscles, the endocrine system, skin, blood, and the respiratory and gastrointestinal systems. Autoimmune diseases include, for example, systemic lupus erythematosus, rheumatoid arthritis, multiple sclerosis, myasthenia *gravis*, and type 1 diabetes.

The disease or condition treatable using the compositions and methods of the present invention may be a hematoimmunological process, including but not limited to Idiopathic Thrombocytopenia Purpura, alloimmune/autoimmune thrombocytopenia, Acquired immune thrombocytopenia, Autoimmune neutropenia, Autoimmune hemolytic anemia, Parvovirus B19-associated red cell aplasia, Acquired anti-factor VIII autoimmunity, acquired von Willebrand disease, Multiple Myeloma and Monoclonal Gammopathy of Unknown Significance, Sepsis, Aplastic anemia, pure red cell aplasia, Diamond-Blackfan anemia, hemolytic disease of the newborn, Immune-mediated neutropenia, refractoriness to platelet transfusion, neonatal, post-transfusion purpura, hemolytic uremic syndrome, systemic Vasculitis, Thrombotic thrombocytopenia purpura, or Evan's syndrome.

The disease or condition may also be a neuroimmunological process, including but not limited to Guillain-Barre syndrome, Chronic Inflammatory Demyelinating Polyradiculoneuropathy, Paraproteinemic IgM demyelinating Polyneuropathy, Lambert-Eaton myasthenic syndrome, Myasthenia *gravis*, Multifocal Motor Neuropathy, Lower Motor Neuron Syndrome associated with anti-/GM1, Demyelination, Multiple Sclerosis and optic neuritis, Stiff Man Syndrome, Paraneoplastic cerebellar degeneration with anti-Yo antibodies, paraneoplastic encephalomyelitis, sensory neuropathy with anti-Hu antibodies, epilepsy, Encephalitis, Myelitis, Myelopathy especially associated with Human T-cell lymphotropic virus-1, Autoimmune Diabetic Neuropathy, Alzheimer's disease, Parkinson's disease, Huntingdon's disease, or Acute Idiopathic Dysautonomic Neuropathy.

The disease or condition may also be a Rheumatic disease process, including but not limited to Kawasaki's disease, Rheumatoid arthritis, Felty's syndrome, ANCA-positive Vasculitis, Spontaneous Polymyositis, Dermatomyositis, Antiphospholipid syndromes, Recurrent spontaneous abortions, Systemic Lupus Erythematosus, Juvenile idiopathic arthritis, Raynaud's, CREST syndrome, or Uveitis.

The disease or condition may also be a dermatoimmunological disease process, including but not limited to Toxic Epidermal Necrolysis, Gangrene, Granuloma, Autoimmune skin blistering diseases including *Pemphigus vulgaris*, Bullous Pemphigoid, *Pemphigus foliaceus, Vitiligo*, Streptococcal toxic shock syndrome, *Scleroderma*, systemic sclerosis including diffuse and limited cutaneous systemic sclerosis, or Atopic dermatitis (especially steroid dependent).

The disease or condition may also be a musculoskeletal immunological disease process, including but not limited to Inclusion Body Myositis, Necrotizing fasciitis, Inflammatory Myopathies, Myositis, Anti-Decorin (BJ antigen) Myopathy, Paraneoplastic Necrotic Myopathy, X-linked Vacuolated Myopathy, Penacillamine-induced Polymyositis, Atherosclerosis, Coronary Artery Disease, or Cardiomyopathy.

The disease or condition may also be a gastrointestinal immunological disease process, including but not limited to pernicious anemia, autoimmune chronic active hepatitis, primary biliary cirrhosis, Celiac disease, dermatitis herpetiformis, cryptogenic cirrhosis, Reactive arthritis, Crohn's disease, Whipple's disease, ulcerative colitis, or sclerosing cholangitis.

The disease or condition may also be Graft Versus Host Disease, Antibody-mediated rejection of the graft, Post-bone marrow transplant rejection, Postinfectious disease inflammation, Lymphoma, Leukemia, Neoplasia, Asthma, Type 1 Diabetes mellitus with anti-beta cell antibodies, Sjogren's syndrome, Mixed Connective Tissue Disease, Addison's disease, Vogt-Koyanagi-Harada Syndrome, Membranoproliferative glomerulonephritis, Goodpasture's syndrome, Graves' disease, Hashimoto's thyroiditis, Wegener's granulomatosis, micropolyarterits, Churg-Strauss syndrome, Polyarteritis nodosa or Multisystem organ failure.

In another embodiment, the stradomers herein described could be utilized in a priming system wherein blood is drawn from a patient and transiently contacted with the stradomer (s) for a period of time from about one half hour to about three hours prior to being introduced back into the patient. In this form of cell therapy, the patient's own effector cells are exposed to stradomer that is fixed on a matrix ex vivo in order to modulate the effector cells through exposure of the effector cells to stradomer. The blood including the modulated effector cells are then infused back into the patient. Such a priming system could have numerous clinical and therapeutic applications.

The stradomers disclosed herein may also be readily applied to alter immune system responses in a variety of contexts to affect specific changes in immune response profiles. Altering or modulating an immune response in a subject refers to increasing, decreasing or changing the ratio or components of an immune response. For example, cytokine production or secretion levels may be increased or decreased as desired by targeting the appropriate combination of FcRs with a stradomer designed to interact with those receptors. Antibody production may also be increased or decreased; the ratio of two or more cytokines or immune cell receptors may be changed; or additional types of cytokines or antibodies may be caused to be produced. The immune response may also be an effector function of an immune cell expressing a FcγR, including increased or decreased phagocytic potential of monocyte macrophage derived cells, increased or decreased osteoclast function, increased or decreased antigen presentation by antigen-presenting cells (e.g. DCs), increased or decreased NK cell function, increased or decreased B-cell function, as compared to an immune response which is not modulated by an immunologically active biomimetic disclosed herein.

In a preferred embodiment, a subject with cancer or an autoimmune or inflammatory disease has their immune response altered comprising the step of administering a therapeutically effective amount of a stradomer described herein to a subject, wherein the therapeutically effective amount of the stradomer alters the immune response in the subject. Ideally this intervention treats the disease or condition in the subject. The altered immune response may be an increased or a decreased response and may involve altered cytokine levels including the levels of any of IL-6, IL-10, IL-8, IL-23, IL-7, IL-4, IL-12, IL-13, IL-17, TNF-alpha and IFN-alpha. In a preferred embodiment, Il-6 or IL-8 are decreased in response to therapy. In an especially preferred embodiment, IL-6 and IL-8 are decreased in response to therapy. The invention is however not limited by any particular mechanism of action of the described biomimetics. The altered immune response may be an altered autoantibody level in the subject. The altered immune response may be an altered autoaggressive T-cell level in the subject.

For example, reducing the amount of TNF-alpha production in autoimmune diseases can have therapeutic effects. A practical application of this is anti-TNF-alpha antibody therapy (e.g. REMICADE®) which is clinically proven to treat Plaque Psoriasis, Rheumatoid Arthritis, Psoriatic Arthritis, Crohn's Disease, Ulcerative Colitis and Ankylosing Spondylitis. These autoimmune diseases have distinct etiologies but share key immunological components of the disease processes related to inflammation and immune cell activity. A stradomer designed to reduce TNF-alpha production will likewise be effective in these and may other autoimmune diseases. The altered immune response profile may also be direct or indirect modulation to effect a reduction in antibody production, for example autoantibodies targeting a subjects own tissues, or altered autoaggressive T-cell levels in the subject. For example, Multiple Sclerosis is an autoimmune disorder involving autoreactive T-cells which may be treated by interferon beta therapy. See, e.g., Zafranskaya M, et al., Interferon-beta therapy reduces CD4+ and CD8+ T-cell reactivity in multiple sclerosis, Immunology 2007 May;121(1):29-39-Epub 2006 Dec. 18. A stradomer design to reduce autoreactive T-cell levels will likewise be effective in Multiple Sclerosis and may other autoimmune diseases involving autoreactive T-cells.

The stradomers described herein may be used to modulate expression of co-stimulatory molecules from an immune cell, including a dendritic cell, a macrophage, an osteoclast, a monocyte, or an NK cell or to inhibit in these same immune cells differentiation, maturation, or cytokine secretion, including interleukin-12 (IL-12), or of increasing cytokine secretion, including interleukin-10 (IL-10), or interleukin-6 (IL-6). A skilled artisan may also validate the efficacy of an immunologically active biomimetic by exposing an immune cell to the immunologically active biomimetic and measuring modulation of the immune cell function, wherein the immune cell is a dendritic cell, a macrophage, an osteoclast, or a monocyte. In one embodiment the immune cell is exposed to the immunologically active biomimetic in vitro and further comprising the step of determining an amount of a cell surface receptor or of a cytokine production, wherein a change in the amount of the cell surface receptor or the cytokine production indicates a modulation of the immune cell function. In another embodiment the immune cell is exposed to the immunologically active biomimetic in vivo in a model animal for an autoimmune disease further comprising a step of assessing a degree of improvement in the autoimmune disease.

Methods Employing Fixed Fc

In order to understand the role of Fc: Fc gamma receptor (FcγR, the Fc receptor for IgG Fc) interactions and the importance to hIVIG function of its Fc being biologically immobilized within an immunoglobulin, we compared the effects of hIVIG with both a fixed form of a recombinant IgG1 Fc fragment (rFCF) and a soluble form of a recombinant IgG1 Fc fragment (sFc) containing the hinge-CH2-CH3 domains on the function of monocytes during the process of differentiation from monocytes to immature dendritic cells (iDC).

Exposure of monocytes cultured in granulocyte-macrophage colony stimulating factor (GM-CSF) and interleukin-4 (IL-4), to immobilized rFCF and to immobilized hIVIG, but not low dose soluble hIVIG, enhanced CD86 expression, delayed the expression of CD1 Ic, and suppressed the expression of CDIa on the cells. Furthermore, these changes are likely not secondary to non-specific protein immobilization of the rFCF on plastic, as soluble heat aggregated (sHA) hIVIG, sHA rFCF or high dose hIVIG (recognized to contain multimeric Fs), induced changes similar to those observed with immobilized rFCF.

Taken in concert, our data indicate that exposure of iDC to hIVIG immobilized on the surface of a solid, semi-solid, or gelatinous substrate results in a unique population of DCs (high CD86, low CDIa), capable of orchestrating immune tolerance, and that immobilized molecules that include the functional portion of immunoglobulin G (IgG) Fc fragments can be useful as mimetics of hIVIG for the treatment of local and systemic inflammation, as well as a wide variety of other pathological conditions that are, directly or indirectly, mediated by monocyte derived cells (MDC) such as iDC. Moreover, immobilizing the functional portion of IgG Fc on devices, described herein as "coating devices", that are implanted into the bodies or attached to the bodies of animals (e.g., human patients) with molecules containing the functional portion of IgG Fc fragment can lessen, if not prevent, inflammatory responses to such devices or treat systemic diseases by affecting immune cells that then pass into the circulation, having been altered by contact with the fixed stradomer coated on or into the implanted device.

The invention provides a method of inhibiting the activity of a monocyte-derived cell (MDC). The method includes contacting the cell with a composition comprising a substrate with an Fc reagent bound thereto. The contacting can be in vitro, in vivo, or ex vivo. Alternatively, the cell can be in an animal. The animal can be one that has, or is at risk of developing, a monocyte derived cell mediated condition (MDCMC). The MDC can be, for example, a dendritic cell, a macrophage, a monocyte, or an osteoclast. The invention also provides a method of treatment or prophylaxis. The method that includes administering to an animal a composition containing a substrate having an Fc reagent bound to it, the animal being one that has or is at risk of developing a MDCMC.

It is also possible that the stradomers of the current invention lead to an in vivo fixed Fc reagent. By "in vivo fixed Fc reagent" we mean Fc fixed to the surface of cells, i.e. platelets, in vivo. It has been observed that platelets expressing FcγRs are efficiently coated with the stradomers of the current invention and that these coated platelets induce tolerance in an organism until they are cleared. The stradomers of the current invention have surprisingly been observed to bind efficiently to the percentage of platelets expressing FcγRs. As ova: anti-ova aggregate complexes and RBC:anti-RBC aggregate complexes induce tolerance and prevent destruction of platelets in ITP, these stradomer-coated platelets may induce tolerance in an organism. This may be another mechanism by which the stradomers of the current invention exert their immune modulating functions.

Based on the much higher binding affinity to Fc gamma receptors of the stradomer compared with the native immunoglobulin Fc contained within the stradomer, it is also possible for the stradomers of the current invention to lead to an in vivo fixed immunoglobulin Fc control reagent. By "in vivo fixed immunoglobulin Fc control reagent" we mean stradomer fixed to the surface of cells, including but not limited to monocytes, Dendritic Cells, T cells, Regulatory T cells, Gamma Delta T cells, and platelets, in vivo. By binding to cell surface receptors including Fc gamma receptors, stradomers block other immunoglobulins from binding to these receptors. Monoclonal or polyclonal antibodies are used in research assays such as flow cytometry and in clinical diagnostics. An important aspect of this invention is the prevention of non-specific binding by the Fc component of these antibodies to Fc gamma receptors and other cell surface receptors to which immunoglobulin Fc may bind.

As used herein, the term "monocyte-derived cell mediated condition (MDCMC)" refers to a pathologic condition that is directly or indirectly, partially or wholly, due to the activity of, or factors produced by, monocyte-derived cells. Monocyte-derived cells include, but are not limited to, monocytes, macrophages, interdigitating dendritic cells (generally referred to herein as "dendritic cells" comprising dendritic-like cells and follicular dendritic-like cells) (mature and immature), osteoclasts, microglia-like cells, monocyte derived insulin-producing islet-like cells, monocyte-derived immature mast cells and monocyte-derived microparticles.

With respect to methods using fixed Fc, the term "Fc reagent" refers to any molecule, or molecular complex, that includes one or more (e.g., 2, 3, 4, 5, 6, 7, 8, 9, 10, 12, 15, 18, 20, or more) functional portions of an immunoglobulin Ig (IgG) Fc fragment. The Fc fragment of IgG consists of the C-terminal portions of the two IgG heavy chains of an IgG molecule linked together and consists of the hinge regions, the CH2 domains, and the CH3 domains of both heavy chains linked together. The "functional portion of the IgG Fc fragment" consists of the hinge regions, the CH2 domains, and optionally, all or some (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49) of the first 50 (from the N-terminus) amino acids of the CH3 domains, of both heavy chains linked together. In humans, (a) the IgG1 hinge region contains 15 amino acids, the CH2 domain contains 110 amino acids, and the CH3 domain contains 106 amino acids; (b) the IgG2 hinge region contains 12 amino acids, the CH2 domain contains 109 amino acids, and the CH3 domain contains 107 amino acids; (c) the IgG3 hinge region contains 62 amino acids, the CH2 domain contains 104 amino acids, and the CH3 domain contains 106 amino acids; and (d) the IgG4 hinge region contains 12 amino acids, the CH2 domain contains 109 amino acids, and the CH3 domain contains 107 amino acids.

As in wild-type IgG molecules, in the above-described Fc reagents the two polypeptide chains derived from IgG heavy chains are generally, but not necessarily, identical. Thus, an Fc reagent can be, without limitation, a whole IgG molecule, a whole IgG molecule linked to a non-immunoglobulin derived polypeptide, an IgG Fc fragment, an IgG Fc fragment linked to a non-immunoglobulin derived polypeptide, a functional portion of an IgG Fc fragment, a functional portion of an IgG Fc fragment linked to a non-immunoglobulin derived polypeptide or multimers (e.g., dimers, trimers, tetramers, pentamers, hexamers, heptamers, octamers, nonamers, or decamers) of any of these. Fc reagents can also be the above-described stradomers and stradobodies provided that they fall within the definition of a Fc reagent above.

In the fixed Fc, immunoglobulin heavy chain components of the Fc reagents can have wild-type amino acid sequences or they can be wild-type amino acid sequences but with not more than 20 (e.g., not more than: 19, 18, 17, 16, 15, 14, 13, 12, 11, 10, 9, 8, 7, 6, 5, 4, 3, 2, or 1) amino acid substitutions. Such substitutions are preferably, but not necessarily, conservative substitutions. Conservative changes typically include changes within the following groups: glycine and alanine; valine, isoleucine, and leucine; aspartic acid and glutamic acid; asparagine, glutamine, serine and threonine; lysine, histidine and arginine; and phenylalanine and tyrosine.

An "Fc reagent" of the invention has least 25% (e.g., at least: 30%; 40%; 50%; 60%; 70%; 80%; 90%; 95%; 98%; 99%; 99.5%; or 100% or even more) of the ability of the IgG molecule from which the IgG heavy chain components of the Fc reagent were derived (the reference IgG molecule) to bind to an Fc receptor of interest. Where an "Fc reagent" has heavy chain components derived from more than one type of IgG molecule, the reference IgG molecule is the one that binds with the greatest avidity to the relevant Fc receptor of interest.

As used herein "fixed Fc" refers to an Fc reagent that is bound to a "substrate" as defined below. The terms "fixed Fc," "bound Fc" and "stabilized Fc" are synonymous terms. Fixed Fc is comprised of the functional portion of Fc (including but not limited to any polypeptide that includes the functional portion of Fc) attached to a substrate. Fixed Fc includes, for example, direct binding as well as indirect binding through polymers of Fc to substrate; incorporation of the full IgG Fc in isolation; incorporation of only the functional domains of IgG Fc; or incorporation of the full IgG Fc or functional domains of IgG Fc as part of a larger polypeptide such as an antibody, a stradomer, or a stradobody. As applied to fixed Fc, the term "substrate" refers to a solid, semisolid, or gelatinous object. The substrate can be implanted in, or attached (or adhered) to the surface of, the body of an animal. The substrates can include, for example, liquid or gaseous components but at least a portion of the substrate is solid, semi-solid, or gelatinous. Thus, a substrate can be a substance that is substantially insoluble in an aqueous solvent but soluble in a non-aqueous solvent. Such substances include lipids (e.g., phospholipids), fatty acids, and other fat-soluble, aqueous solvent-insoluble compounds. From this, it will be clear that substrates include liposomes. The substrate may be porous or non-porous. In certain embodiments, the substrate is inert to the surface and/or body to which it is implanted, attached, or adhered.

The substrate can contain or be made of a synthetic polymer, e.g., nylon, Teflon, dacron, polyvinyl chloride, PEU (poly (ester urethane)), PTFE (polytetrafluoroethylene), PMMA (methyl methacrylate) PEEK, thermoplastic elastomers, radiopaque polymers, polyethersulfone, silicons, polycarbonates, polyurethanes, polyisobutylene and its copolymers, polyesters, polyolefins, polyisobutylene, ethylene-alphaolefin copolymers, acrylic polymers and copolymers, vinyl halide polymers and copolymers such as polyvinyl chloride, polyvinyl ethers, polyvinyl methyl ether, polyvinylidene halides, polyvinylidene fluoride, polyvinylidene chloride, polyacrylonitrile, polyvinyl ketones, polyvinyl aromatics, polystyrene, polyvinyl esters, polyvinyl acetate, copolymers of vinyl monomers, copolymers of vinyl monomers and olefins, ethylene-methyl methacrylate copolymers, acrylonitrile-styrene copolymers, ABS resins, ethylene-vinyl acetate copolymers, polyamides, Nylon 66, polycaprolactone, alkyd resins, polyoxyethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, polysiloxanes, substituted polysiloxanes, ethylene vinyl acetate copolymers, polyolefin elastomers, and EPDM rubbers, and combinations thereof.

The substrate can also contain or be made of a metal or a metal alloy, e.g., stainless steel, platinum, iridium, titanium, tantalum, nickel-titanium alloy, or cobalt-chromium alloy. Moreover, the substrate can include or be an animal tissue or an animal tissue product, e.g., a tissue or organ graft. The animal tissue can be, for example, bone (e.g., osteogenic bone) or cartilage. Furthermore, the substrate can contain a protein, e.g., collagen or keratin. The substrate can also be or contain a tissue matrix, e.g., an acellular tissue matrix. Particulate and non-p articulate acellular matrices are described in detail in, for example, U.S. Pat. Nos. 5,336,616 and 6,933,326, the disclosures of which are incorporated herein by reference in their entirety. The substrate can also be or include an animal cell (e.g., tissue repair cells such as fibroblasts; mesenchymal stem cells) and it can be, for example, a hair transplant plug. The substrate can contain or be a polysaccharide, e.g., agarose. It can also contain or be a salt, preferably a relatively insoluble salt, e.g., calcium sulfate. The substrate can be a gel or cream. Moreover, it can contain silicon or silastic. Substrates can also contain a natural fiber, e.g., silk, cotton, or wool.

In addition, the substrate can be an implantable medical device. It can be, for example, a stent (e.g., a vascular stent such as a coronary artery stent; an airway stent such as an endotracheal or nasal stent; a gastrointestinal stent such a biliary or pancreatic stent; or a urinary stent such as a ureteral stent) or a surgical suture (e.g., a braid silk, chromic gut, nylon, plastic, or metal suture) or a surgical clip (e.g., an aneurism clip). The substrate can be, for example, an artificial hip, an artificial hip joint, an artificial knee, an artificial knee joint, an artificial shoulder, an artificial shoulder joint, an artificial finger or toe joint, a bone plate, a bone dowel, a bone non-union implant, an intervertebral disk implant, bone cement, or a bone cement spacer. It can also be an arterial-venous shunt, an implantable wire, a pacemaker, an artificial heart, a heart assist device, a cochlear implant, an implantable defibrillator, a spinal cord stimulator, a central nervous system stimulator, or a peripheral nerve implant. Other substrates are dental prostheses or dental crowns.

In other embodiments, the substrate can be a large vessel embolic filtering device or cage, a percutaneous device, a dermal or sub-mucosal patch, or an implantable drug delivery device. The substrate can also be a large blood vessel graft, wherein the blood vessel is, for example, a carotid artery, a femoral artery, or an aorta. Moreover, the substrate can be a subdermal implant, a corneal implant, an intraocular lens, or a contact lens.

The substrate can be in the form of a sheet, a bead, a mesh, a powder particle, a thread, a bead, or a fiber. It can also include or be a solid, a semi-solid or a gelatinous substance.

The substrate can also be a cell that expresses FcγR. Preferably the substrate is a platelet.

Polymers useful in the invention are preferably those that are biostable, biocompatible, particularly during insertion or implantation of the device into the body, and avoid irritation to body tissue.

Fc reagents can be coated (i.e., fixed or stabilized) onto substrates in any of a variety of manners. For example, they can be coated directly on the surface of substrates where they remain attached by, for example, hydrophobic interactions. Below are described a few other methodologies ((a)-(e)) involving the use of polymers:

(a) The Fc reagent is mixed with a miscible polymer blend which is then layered on to the surface of the implantable synthetic material, thereby stabilizing the Fc reagent. Monomers routinely used in the art to make polymer blends include PLMA [poly(lauryl methacrylate)]; PEG [polyethylene glycol], PEO [polyethylene oxide]; the alkyl functionalized methacrylate polymers PMMA, PEMA. PPMA, and PBMA; itaconates; fumarates; and styrenics.

(b) A polymeric undercoat layer or a nanometer dimension film is adhered to the substrate surface and then the Fc reagent is adhered to the polymeric undercoat layer or nanometer dimension film, thereby stabilizing the F reagent.

(c) A thin film of a polymer monomer is applied to the implantable substrate surface and the monomer is then caused to polymerize Such monomers include, for example, Methane, Tetrafluorethylene, Benzene, Methanol, Ethylene oxide, Tetraglyme, Acrylic acid, Allylamine, Hydroxyethyl methacrylate, N-vinyl pyrrolidone, and mercaptoethanol. The Fc reagent is then attached to the resulting monomer.

(d) The substrate is coated with a protein such as protein A or albumin which attaches to the Fc reagent, thereby stabilizing Fc to the surface of the substrate.

(e) The Fc reagent can be tagged with a chain of hydrophobic amino acids that bind to implantable synthetic materials and cause the stabilized Fc to orient uniformly.

The methods of the invention can be applied to any animal species and the IgG molecules from which the IgG-derived portions of Fc reagents are made can be from any animal species. Naturally, relevant animal species are those in which IgG or IgG-like molecules occur. Generally the species to which the methods are applied and the species from which the IgG-derived portions of the Fc reagents used in the methods are the same. However, they are not necessarily the same. Relevant animal species are preferably mammals and these include, without limitation, humans, non-human primates (e.g., monkeys, baboons, and chimpanzees), horses, bovine animals (e.g., bulls, cows, or oxen), pigs, goats, sheep, dogs, cats, rabbits, gerbils, hamsters, rats, and mice. Non-mammalian species include, for example, birds (e.g., chickens, turkeys, and ducks) and fish.

The terms "treating", "treatment", and "prophylaxis" have the same meaning using fixed Fc as described above for stradomers.

Where the fixed Fc are implantable devices coated with Fc reagents, they can be implanted in, attached to, or adhered to relevant internal organs or tissue or body surfaces of relevant subjects using methods well known in the art. Where they are formulated as, for example, suspensions, powders, they can be formulated and administered as described above for stradomers.

The fixed Fc reagents of the present invention may be used to treat or prevent conditions including but not limited to cancer, congestive heart failure (CHF), vasculitis, rosecea, acne, eczema, myocarditis and other conditions of the myocardium, systemic lupus erythematosus, diabetes, spondylopathies, synovial fibroblasts, and bone marrow stroma; bone loss; Paget's disease, hypertrophic bone formation; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures, bone pain management, and humoral malignant hypercalcemia, ankylosing spondyloarthropathies; transplantation rejection, and viral infections.

All autoimmune diseases may be in part or in whole an MDCMD. The term "autoimmune disease" as used herein refers to a varied group of more than 80 chronic illnesses. In all of these diseases, the underlying problem is that the body's immune system attacks the body itself. Autoimmune diseases affect all major body systems including connective tissue, nerves, muscles, the endocrine system, skin, blood, and the respiratory and gastrointestinal systems.

The autoimmune disease or condition may be a hematoimmunological process, including but not limited to Idiopathic Thrombocytopenia Purpura, alloimmune/autoimmune thrombocytopenia, Acquired immune thrombocytopenia, Autoimmune neutropenia, Autoimmune hemolytic anemia, Parvovirus B19-associated red cell aplasia, Acquired antifactor VIII autoimmunity, acquired von Willebrand disease, Multiple Myeloma and Monoclonal Gammopathy of Unknown Significance, Sepsis, Aplastic anemia, pure red cell aplasia, Diamond-Blackfan anemia, hemolytic disease of the newborn, Immune-mediated neutropenia, refractoriness to platelet transfusion, neonatal, post-transfusion purpura, hemolytic uremic syndrome, systemic Vasculitis, Thrombotic thrombocytopenia purpura, or Evan's syndrome.

The autoimmune disease or condition may be a neuroimmunological process, including but not limited to Guillain-Barre syndrome, Chronic Inflammatory Demyelinating Polyradiculoneuropathy, Paraproteinemic IgM demyelinating Polyneuropathy, Lambert-Eaton myasthenic syndrome, Myasthenia *gravis*, Multifocal Motor Neuropathy, Lower Motor Neuron Syndrome associated with anti-/GM1, Demyelination, Multiple Sclerosis and optic neuritis, Stiff Man Syndrome, Paraneoplastic cerebellar degeneration with anti-Yo antibodies, paraneoplastic encephalomyelitis, sensory neuropathy with anti-Hu antibodies, epilepsy, Encephalitis, Myelitis, Myelopathy especially associated with Human T-cell lymphotropic virus-1, Autoimmune Diabetic Neuropathy, or Acute Idiopathic Dysautonomic Neuropathy.

The autoimmune disease or condition may be a Rheumatic disease process, including but not limited to Kawasaki's disease, Rheumatoid arthritis, Felty's syndrome, ANCA-positive Vasculitis, Spontaneous Polymyositis, Dermatomyositis, Antiphospholipid syndromes, Recurrent spontaneous abortions, Systemic Lupus Erythematosus, Juvenile idiopathic arthritis, Raynaud's, CREST syndrome, or Uveitis.

The autoimmune disease or condition may be a dermatoimmunological disease process, including but not limited to Toxic Epidermal Necrolysis, Gangrene, Granuloma, Autoimmune skin blistering diseases including *Pemphigus vulgaris*, Bullous Pemphigoid, and *Pemphigus foliaceus, Vitiligo*, Streptococcal toxic shock syndrome, *Scleroderma*, systemic sclerosis including diffuse and limited cutaneous systemic sclerosis, or Atopic dermatitis (especially steroid dependent).

The autoimmune disease or condition may be a musculoskeletal immunological disease process, including but not limited to Inclusion Body Myositis, Necrotizing fasciitis, Inflammatory Myopathies, Myositis, Anti-Decorin (BJ antigen) Myopathy, Paraneoplastic Necrotic Myopathy, X-linked Vacuolated Myopathy, Penacillamine-induced Polymyositis, Atherosclerosis, Coronary Artery Disease, or Cardiomyopathy.

The autoimmune disease or condition may be a gastrointestinal immunological disease process, including but not limited to pernicious anemia, autoimmune chronic active hepatitis, primary biliary cirrhosis, Celiac disease, dermatitis herpetiformis, cryptogenic cirrhosis, Reactive arthritis, Crohn's disease, Whipple's disease, ulcerative colitis, or sclerosing cholangitis.

The autoimmune disease or condition may be Graft Versus Host Disease, Antibody-mediated rejection of the graft, Post-bone marrow transplant rejection, Post-infectious disease inflammation, Lymphoma, Leukemia, Neoplasia, Asthma, Type 1 Diabetes mellitus with anti-beta cell antibodies, Sjogren's syndrome, Mixed Connective Tissue Disease, Addison's disease, Vogt-Koyanagi-Harada Syndrome, Membranoproliferative glomerulonephritis, Goodpasture's syndrome, Graves' disease, Hashimoto's thyroiditis, Wegener's granulomatosis, micropolyarterits, Churg-Strauss syndrome, Polyarteritis nodosa or Multisystem organ failure.

"Cancer" herein refers to or describes the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, lymphangiosarcoma, lymphangioendotheliosarcoma, leiomyosarcoma, rhabdomyosarcoma, fibrosarcoma, myxosarcoma, chondrosarcoma), osteoclastoma, neuroendocrine tumors, mesothelioma, chordoma, synovioma, schwanoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile cancer, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwanoma, and other carcinomas, head and neck cancer, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, tumors of the vascular system (angiosarcoma and hemagiopericytoma), hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, osteolytic bone cancers, and bone metastasis.

As used herein, a subject "at risk of developing a monocyte-derived cell mediated disease (MDCMD)" is a subject that has a predisposition to develop the MDCMD, i.e., a genetic predisposition to develop the MDCMD or has been exposed to conditions that can result in MDCMD. A subject "suspected of having a MDCMD" is one having one or more symptoms of a MDCMD. From the above it will be clear that neither subjects "at risk of developing a MDCMD" nor subjects "suspected of having a MDCMD" are all individuals within a species of interest.

In any of the above methods, the MDCMC can be one caused by the substrate and the Fc reagent serves to prevent or ameliorate the MDCMC.

Applications in Immunological Assays

The immunologically active biomimetics disclosed herein may be used to perform immunological assays for testing the immune cell functions for which the immunologically active biomimetics were designed to modulate.

Signaling through low affinity Fcγ receptor pathways requires receptor aggregation and cross linking on the cell surface. These aggregation and cross linking parameters are postulated to be met through Fab binding to an antigen specific target with subsequent interaction between the Fc region and low affinity FcγRs on the surface of responding cells. In this context, antibodies have the potential to evoke cellular responses through two distinct pathways: 1. Fab interaction/blocking with/of an epitope specific target and 2. Fc interactions with FcRs. Despite this knowledge, current controls for the majority of therapeutic studies using monoclonal antibodies employed in vivo do not adequately address the potential of Fc: Fcγ receptor interactions as contributors to observed functional effects. Multiple strategies are currently employed to eliminate Fc:FcR interactions as confounding variables. For example, some studies employ Scv (single chain variable regions) or Fab fragments, which retain epitope specificity but lack the Fc region. These approaches are limited by the short half life of these reagents and their limited potential to induce signaling. Other studies employ fusion proteins composed of a receptor or ligand fused to an Fc fragment. While these types of approaches help to differentiate Fab specific effects from those observed with receptor ligand interactions, they do not effectively control for Fc mediated effects. Evaluations of antibody based therapeutics in animal models may also employ isotype control antibodies with an irrelevant Fab binding site. The rationale for this choice is based on presumed functional similarity between antibodies of the same isotype regardless of their Fab binding specificity or affinity. However, this use of irrelevant isotype controls has several fundamental flaws:

1. If the Fab fragments of these antibodies cannot bind a ligand or antigenic epitope, it is likely that the Fc fragments will not stimulate signaling through low affinity FcR interactions because of the absence of Fcγ receptor cross-linking. Therefore, observed functional differences between experimental and control antibodies cannot be correctly attributed to Fab interaction with an epitope specific target lacking a means to cross-link the FcγR.
2. If these isotypes are produced in cells which yield different glycoforms or different relative percentages of individual glycoforms than the parent antibody, binding to both low and high affinity FcRs will be altered, even if Fab affinity is identical.

While there is no perfect control to overcome this problem, one option is the use of isotype specific stradomers produced in the same cells as the parent antibodies and given at a dose proportional to the expression levels of the epitope targeted by the experimental antibody. For example, the appropriate control for an epitope-specific antibody produced in rat would be a rat isotype-specific stradomer capable of aggregating Fcγ receptor on the surface of effector cells.

Generally, an immune cell is exposed to an effective amount of an immunologically active biomimetic to modulate an activity of an immune cell in a known way and this immune modulation is compared to a test compound or molecule to determine if the test compound has similar immune modulating activity.

In another embodiment, heat aggregated stradomers, and aggregated immunoglobulins may be used as reagents for laboratory controls in various immunological assays herein described and known to those of ordinary skill in the art.

Immunological assays may be in vitro assays or in vivo assays and may involve human or non-human immune cells using a species-matched or species-unmatched stradomer. In one embodiment an immunological assay is performed by using an effective amount of the immunologically active biomimetic to modulate an activity of an immune cell and comparing the modulation with a modulation of an immune cell by a test compound. The stradomer may serve the function of a positive control reagent in assays involving the testing of other compounds for immunological effect. The assay may compare the effect of the subject monoclonal antibody in comparison to the stradomer for effector cell Fcγ receptor binding and functional response as measured by changes in receptor expression level, cytokine release, and function such as by using a Mixed Lymphocyte Reaction. In this manner, if a stradomer (which lacks the Fab) generates a response which is in part similar to the monoclonal antibody then the monoclonal antibody's effect is, in some part, not due to specificity of its Fab but to the general effect of binding and cross-linking more than one Fcγ receptor on the effector cell.

If the biological activity of a species-specific and isotype-specific antibody is replicated in part or in whole by a species-specific and isotype-specific stradomer then it is clear that Fc-Fcγ receptor activity accounts for the portion of observed biological activity attributable to the species-specific and isotype-specific stradomer. Thus species-specific and isotype-specific stradomers are useful in assessing potential therapeutic antibodies to determine whether and to what degree the observed biological activity is attributable either to the Fab portion of the test antibody or to a nonspecific effect of the Fc portion of the molecule binding to and cross-linking more than one Fcγ receptor.

The stradomers of the current invention are also useful in blocking non-specific binding of Fc receptors during antibody based immunoassays such as flow cytometry, western blot, immunohistochemistry and immunofluorescence assay. Traditionally, in assays such as these non-specific antibodies of the same species as the test antibody are used to block non-specific binding to Fc receptors. The stradomers of the current invention provide a benefit over traditional means of Fc blocking in that each stradomer has multiple FcR binding sites, and therefore much less stradomer can be used. Additionally, because the stradomer of the current invention lacks the Fab antigen-binding portion of the antibody, no non specific binding to dead cells, for example, will be observed as is usually the case with species matched IgG control.

The stradomers of the current invention have surprisingly been found to bind endotoxin with very high affinity. Standard endotoxin removal kits and columns fail to remove significant percentages of the tightly bound endotoxin from stradomers. Therefore, the claimed compositions may be useful in acting as a binding pool for endotoxin a useful tool for endotoxin removal in both pharmaceutical and laboratory preparations. This is beneficial in that the complexes formed between endotoxin and stradomers have high enough affinity to efficiently remove endotoxin from a pharmaceutical preparation or composition. In one embodiment, the endotoxin-stradomer complexes are removed from the composition by filtration.

All references cited herein are incorporated by reference in their entireties.

EXAMPLES

Example 1 Production and Purification of the Stradomers

HEK293F cells (Invitrogen, Carlsbad, CA) or Chinese Hamster Ovary Cells (CHO) were used for stable expression of G045/M045 and G051. The HEK293F or CHO cells were grown in suspension for scale up of protein expression.

Genes encoding G045c (SEQ ID NO:4), G045old (SEQ ID NO:7) G051 (SEQ ID NO:18), G019 (SEQ ID NO: 8), G028 (SEQ ID NO:9), G046 (SEQ ID NO: 10), G075 (SEQ ID NO: 20), G076 (SEQ ID NO: 21), G096 (SEQ ID NO: 28), G098 (SEQ ID NO: 24), G089 (SEQ ID NO: 27), or the corresponding murine sequences of the preceding stradomers were cloned into a vector containing a neomycin resistance gene such as pcDNA3.3 from Invitrogen (Carlsbad, CA) and under the transcriptional control of the CMV promoter to facilitate high level expression of G045 or G051. Plasmid DNA for transfection were isolated from bacterial culture using a endotoxin free plasmid DNA isolation kit (Nucleobond, Macherey-Nagel). G045c/G045old and G051 encoding plasmid DNA was linearized with restriction enzyme and transfected into 293-F cell or CHO cells. Following transfection positive cells expressing G045c, G045old or G051 were selected with Geneticin/G418 to obtain a pool of transfected cells. To obtain a clonal cell line the pool of stably transfected cells were diluted to 1-2 cells per well into a 96 well plate from which single cells clones of the stable cell line were obtained. Single cell clones were screened by ELISA for protein expression. Single cell clones are grown up and G045c, G045old, G051, G019, G028, G046, G075, G076, G096, G098, or G089, protein is harvested from media as secreted protein.

For production of G045c, G045old, G051 G019, G028, G046, G075, G076, G096, G098, or G089 protein by transient transfection HEK293 cells or CHO cells were transfected with DNA encoding the G045c, G045old, G051, G019, G028, G046, G075, G076, G096, G098, or G089 proteins under control of a CMV promoter to ensure high level expression of protein. Transfection was done with one of several commercially available transfection reagents. G045c, G045old, G051, G019, G028, G046, G075, G076, G096, G098, or G089 secreted protein is harvested from the cell culture media 4-5 days after transfection.

Cell culture media from either transiently transfected cells or stable cell lines was filtered using a 0.22 um filter and adjusted to pH 7.2 with 1 volume of binding buffer (20 mM sodium phosphate pH7.2+150 mM NaCl) and purified by affinity chromatography on a HiTrap Mabselect protein A affinity column using an AKTAXpress purification system. (GE life sciences) Following elution in 0.1 M sodium citrate pH3.3 protein is purified on a HiPrep 26/20 desalting column for buffer exchange.

For further purification G045c, G045old, G051, G019, G028, G046, G075, G076, G096, G098, or G089 protein is purified by gel filtration on a HiLoad Superdex 200 gel filtration column (GE Lifesciences) in 50 mM Tris-HCL pH7.5+150 mM NaCl followed by purification on Mono S ion-exchange column (GE Lifesciences). Ion-exchange purification is done in 20 mM MES buffer pH 6 with a 0-1M NaCl gradient. Following chromatography the protein is adjusted to PBS by dialysis. A schematic of the resulting G045c stradomer is depicted in FIG. 1.

Figure 1A:
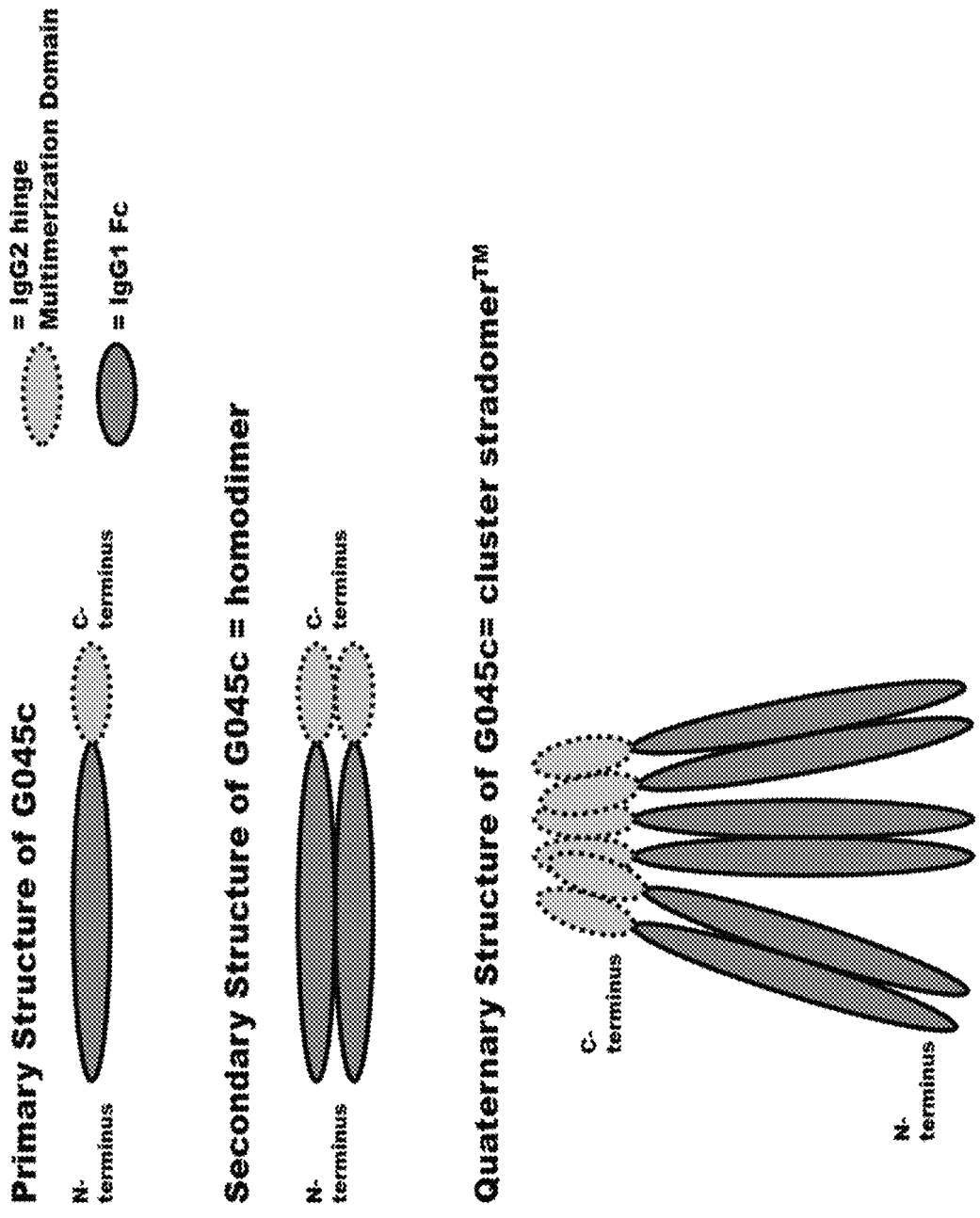
Figure 1C:
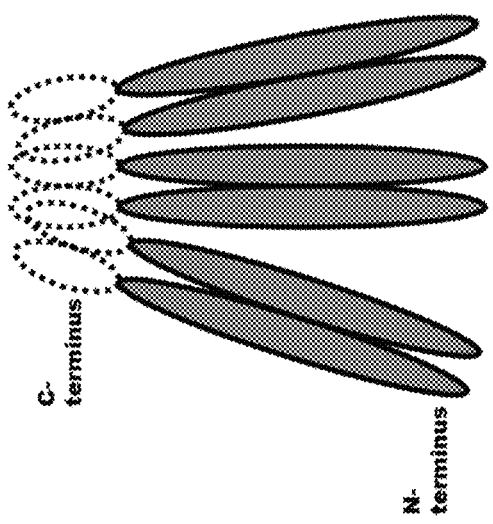
Figure 1D:
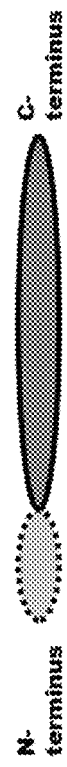
Figure 1D:
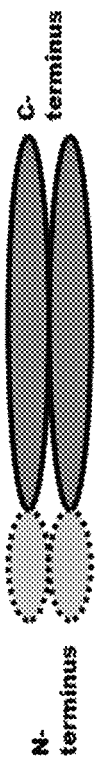
Figure 1D:
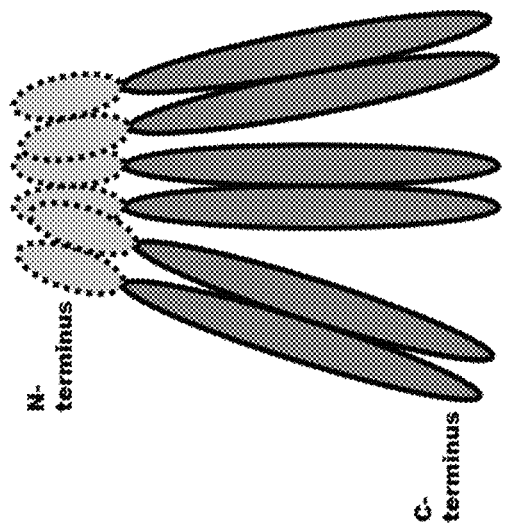
Figure 1E:
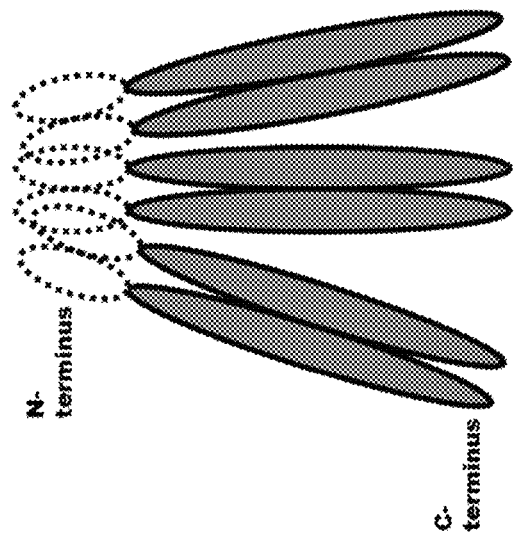
Figure 1F:
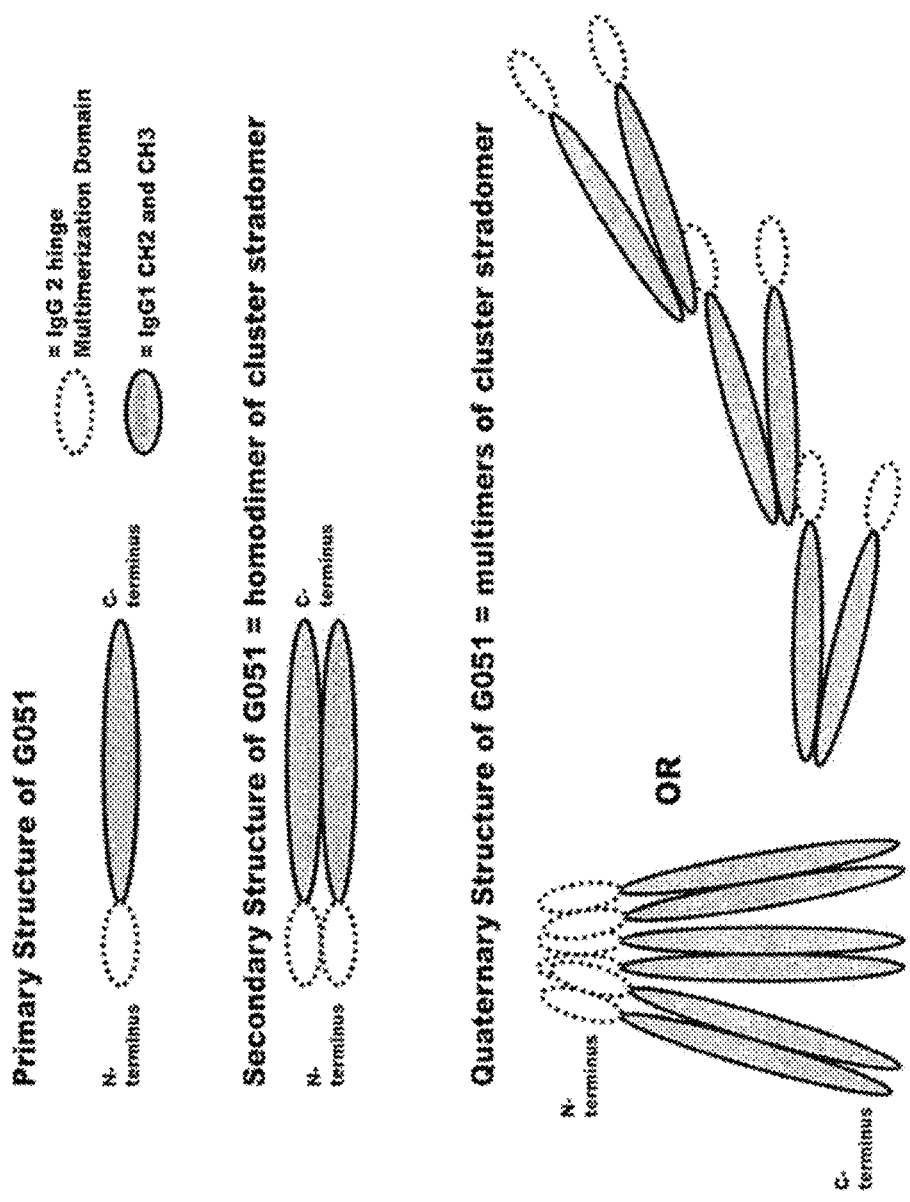
Figure 1G:
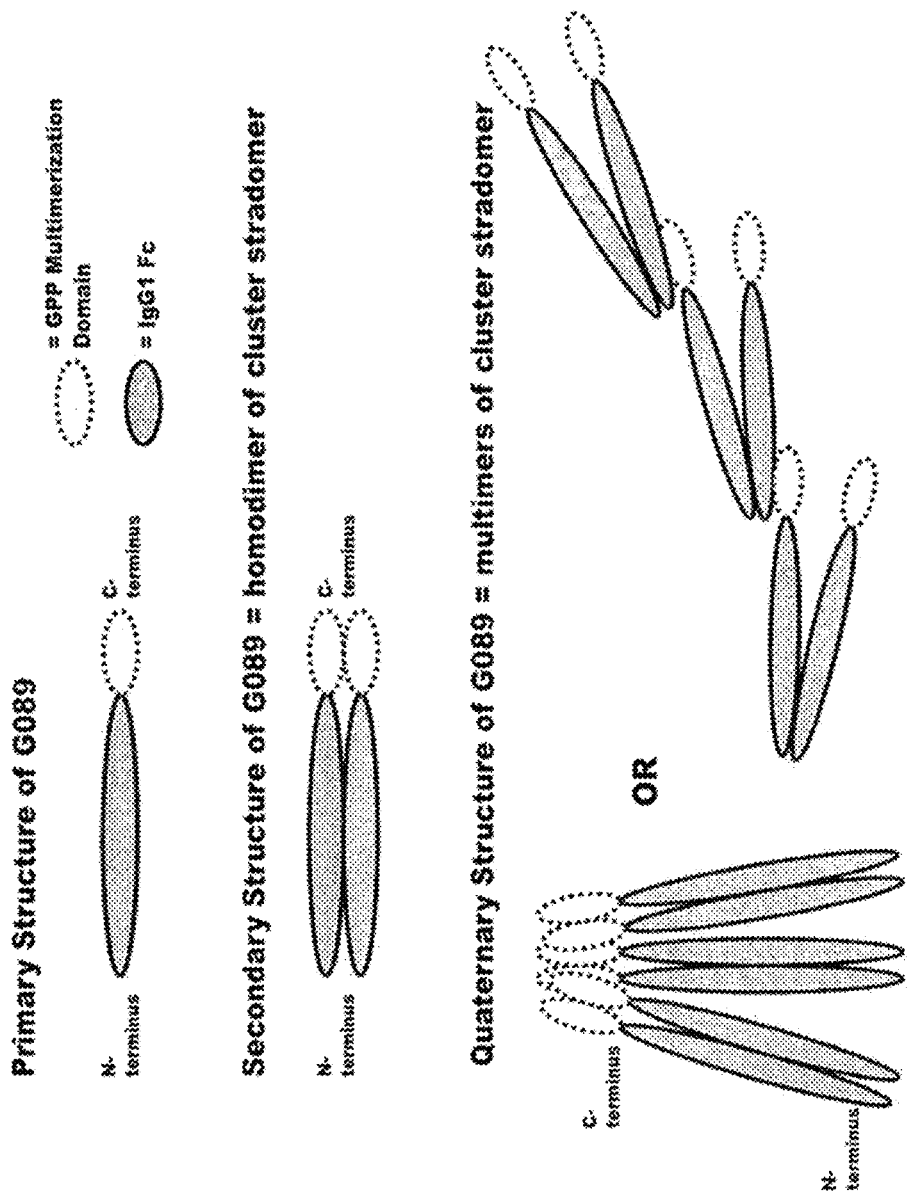
Figure 1H:
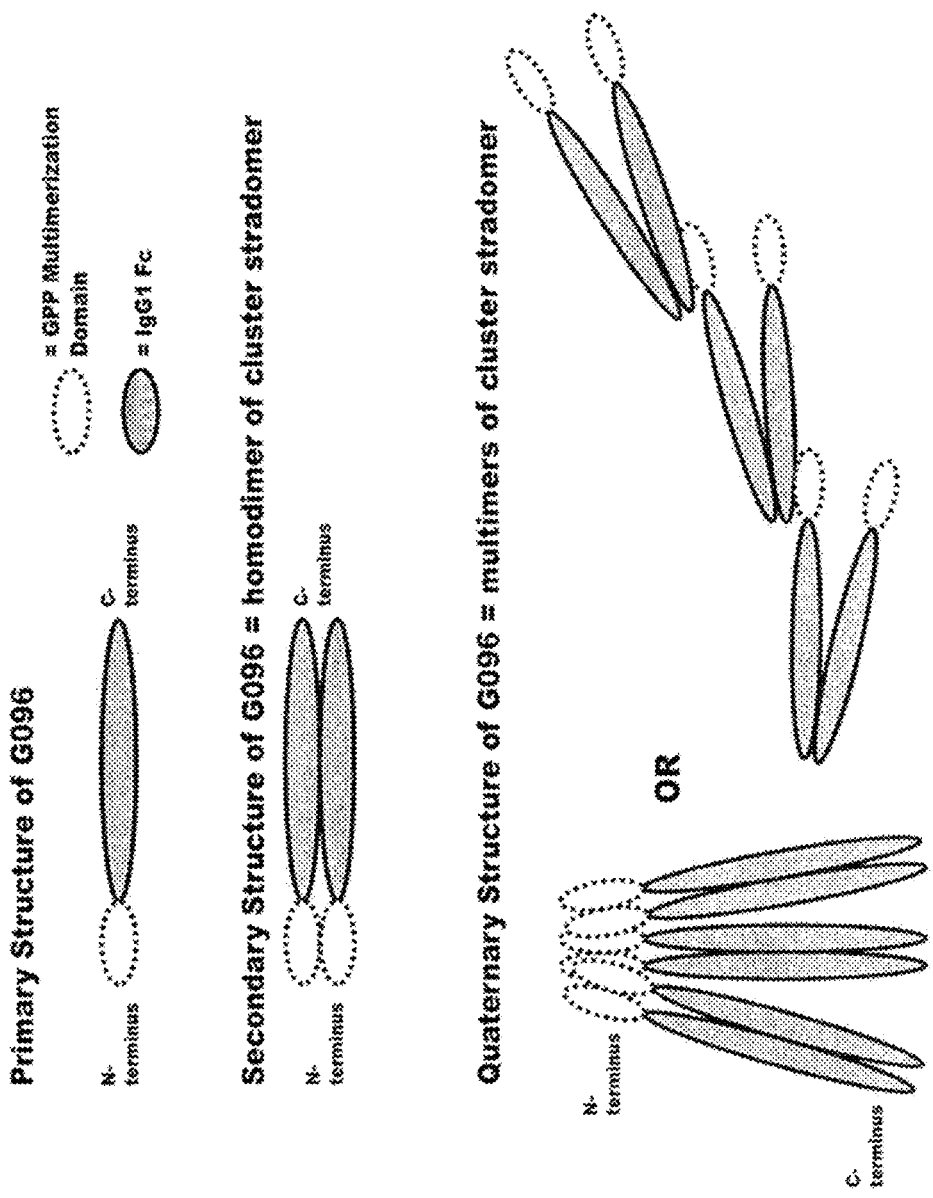
Figure 2A:
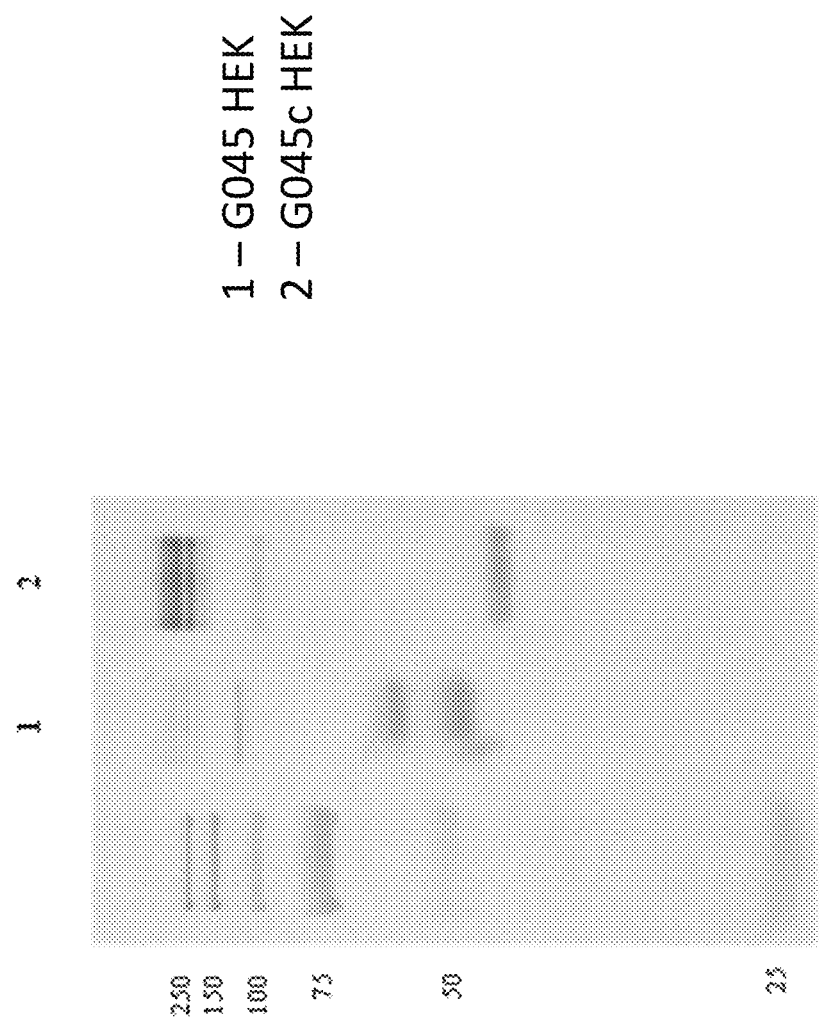
FIG. 2A is a protein gel showing the differences in multimerization capacity between first generation stradomer compounds and the direct naturally linked stradomer compounds of the current invention.

In order to test the multimerization capacity of the resulting G045c protein, a 10% polyacrylamide gel was run containing equal concentrations of G045c produced by the method above, and G045old, produced by the method previously described in WO 2008/151088 and containing the extraneous cloning sequences. Surprisingly, the removal of the extraneous fragments led to a dramatic increase in multimerization in G045c compared with G045old with G045c showing a much higher concentration of higher ordered multimers compared to G045old. (See FIG. 2A).

Figure 2B:
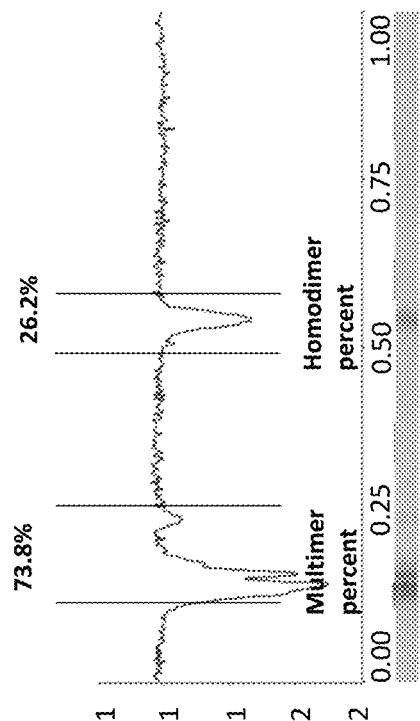
FIG. 2B is a comparison between multimer/monomer formation between the first generation stradomer compounds and the direct naturally linked stradomer compounds of the current invention.
Figure 2B:
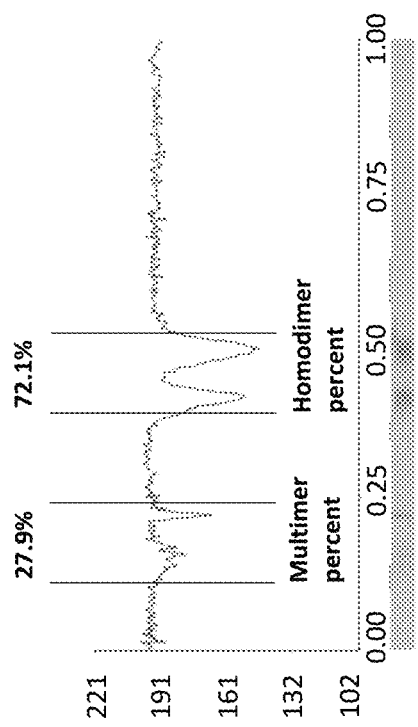

Multimer formation in G045old versus G045c was analyzed using a Gel-DocIT imaging system. Following density scanning of gel pictures protein amount in each gel band was assessed. Surprisingly, multimer formation in the G045old sample was estimated to be approximately 27.9% whereas removal of the extraneous fragments to generate naturally linked stradomers led to multimer formation in the G045c sample that was significantly higher and estimated to be approximately 73.8% of total protein. (See FIG. 2B).

Example 2: Enhanced Efficacy of M045c Compared with M045old in a Mouse Model of Arthritis Assessment of the efficacy of M045c compared to that of M045old in collagen induced arthritis was performed. At day 0 and day 21 DBA1/J mice were immunized with Type II bovine collagen (Chondrex, Inc., Cat. 20021) with a 4 mg/ml solution emulsified with Incomplete Freund's Adjuvant (Sigma, Cat #5506). The mice were weighed weekly and scored daily for signs of arthritis. Each paw was scored and the sum of all four scores was recorded as the Arthritic Index (AI). The maximum possible AI was 16 as follows: 0=no visible effects of arthritis 1=edema and/or erythema of one digit 2=edema and/or erythema of 2 joints 3=edema and/or erythema of more than 2 joints 4=severe arthritis of the entire paw and digits including limb deformation and ankylosis of the joint. Starting at day 22 (treatment day 0) ten of the collagen immunized mice were sorted into treatment groups based upon average AI (3.3) and ten non-diseased mice were designated as non-diseased group. Arthritis index was measured for 14 treatment days after which mice were euthanized. For the positive control group ten of the mice were sorted into treatment based upon average AI (3.3) and dosed orally with 10 ml/kg prednisolone every day. For the group treated with M045c or M045old 20 of the mice were sorted into treatment based upon average AI (3.3) and dosed every 4th day (day 0, day 4, day 8 and day 12) with 400 µg M045c or M045old (17.4 mg/kg).

The mice treated with M045c had statistically less severe disease compared with that of the M045old treated mice at almost all time points tested. (See FIG. 3). Therefore, the removal of the 16 amino acid cloning fragment between the leader sequence and IgG1 Fc leads to not only greater multimer formation, but also increased efficacy against inflammatory disease.

Assessment of the efficacy of M045c, M019, M028, M046 and M051 in collagen induced arthritis were similarly performed and compared to the efficacy of prednisolone. CIA was induced in mice as described above and mice were treated beginning on day 22 post CIA induction with 400 µg of M045, M019, M028, M046 or M051 intravenously twice weekly or 10 mg/kg predisolone everyday and scored for two weeks for AI, as above. Mice receiving each of the tested stradomers had statistically less severe disease than PBS treated controls (see FIG. 9).

Example 3: Synergistic Effect of M045 and Prednisolone in a Mouse Model of Arthritis Assessment of efficacy of M045c combined with low dose prednisolone in a collagen induced arthritis model was performed. Briefly at day 0 and day 21 DBA1/J mice were immunized with Type II bovine collagen (Chondrex, Inc., Cat. 20021) with a 4 mg/ml solution emulsified with Incomplete Freund's Adjuvant (Sigma, Cat #5506). The mice were weighed weekly and scored daily for signs of arthritis. Each paw was scored and the sum of all four scores was recorded as the Arthritic Index (AI). The maximum possible AI was 16 as follows: 0=no visible effects of arthritis 1=edema and/or erythema of one digit 2=edema and/or erythema of 2 joints 3=edema and/or erythema of more than 2 joints 4=severe arthritis of the entire paw and digits including limb deformation and ankylosis of the joint. Starting at day 22 (treatment day 0) ten of the collagen immunized mice were sorted into treatment groups based upon average AI (3.3) and ten non-diseased mice were designated as non-diseased group. Arthritis index was measured for 14 treatment days after which mice were euthanized. For the positive control group ten of the mice were sorted into treatment based upon average AI (3.3) and dosed orally with 10 ml/kg prednisolone every day. For the group treated with M045c ten of the mice were sorted into treatment based upon average AI (3.3) and dosed every 4th day (day 0, day 4, day 8 and day 12) with 400 µg M045c (17.4 mg/kg). For measuring synergy between prednisolone and M045c one group was treated with low dose prednisolone 2 mg/kg every day one group was treated with low dose M045c 200 µg/dose dosing every 4th day and one group was dose with low dose prednisolone 2 mg/kg plus low dose M045c 200 µg/dose dosing every 4th day.

Figure 4:
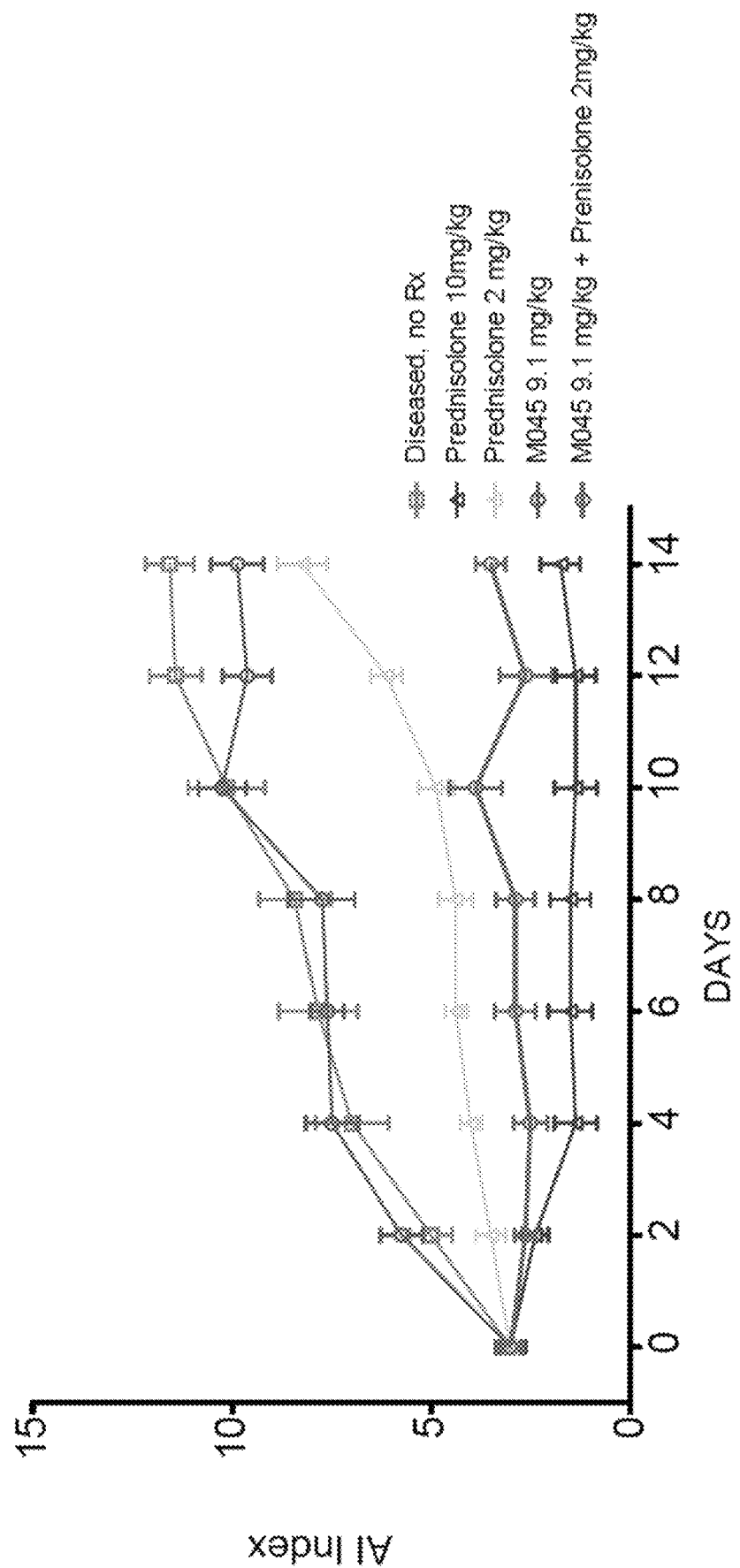
Figure 5A:
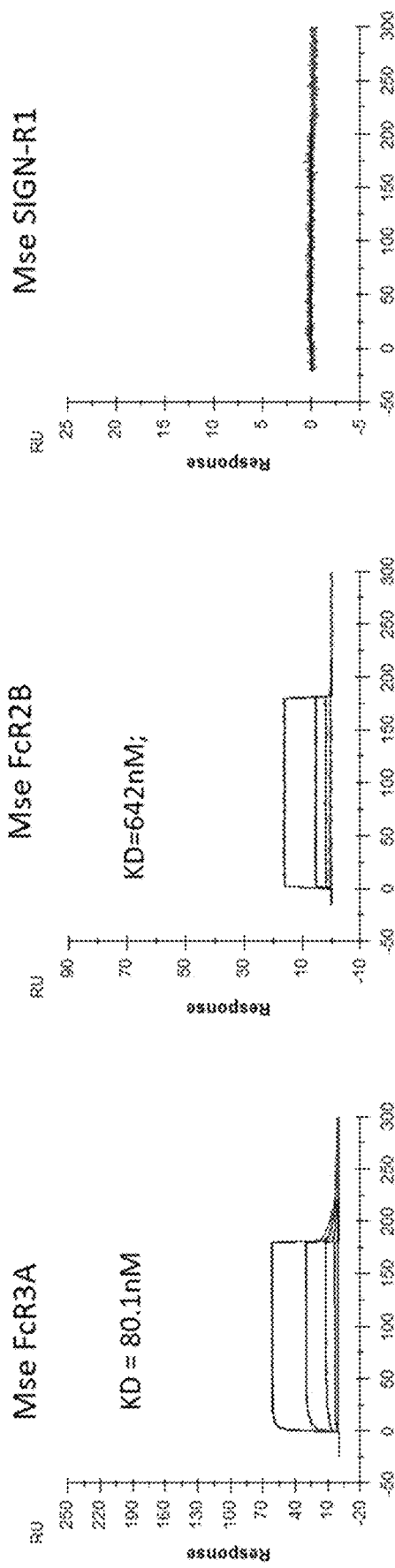
Figure 5B:
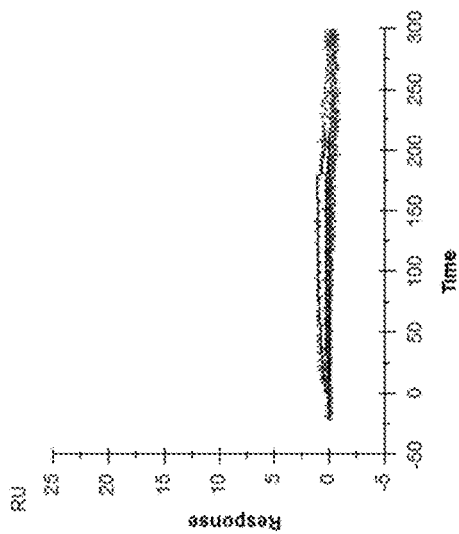
Figure 5B:
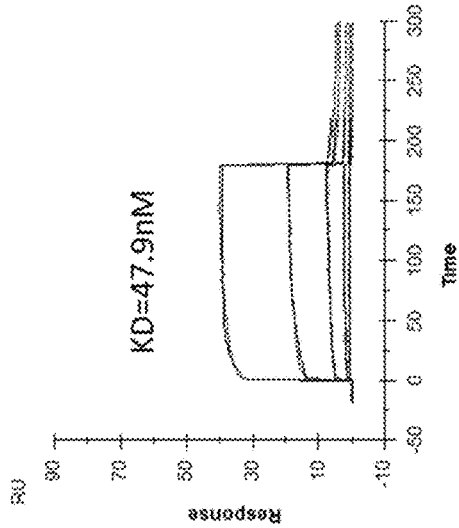
Figure 5B:
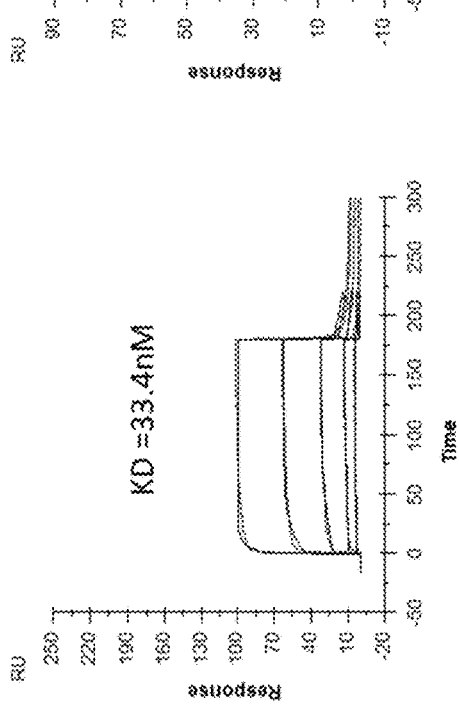
Figure 5C:
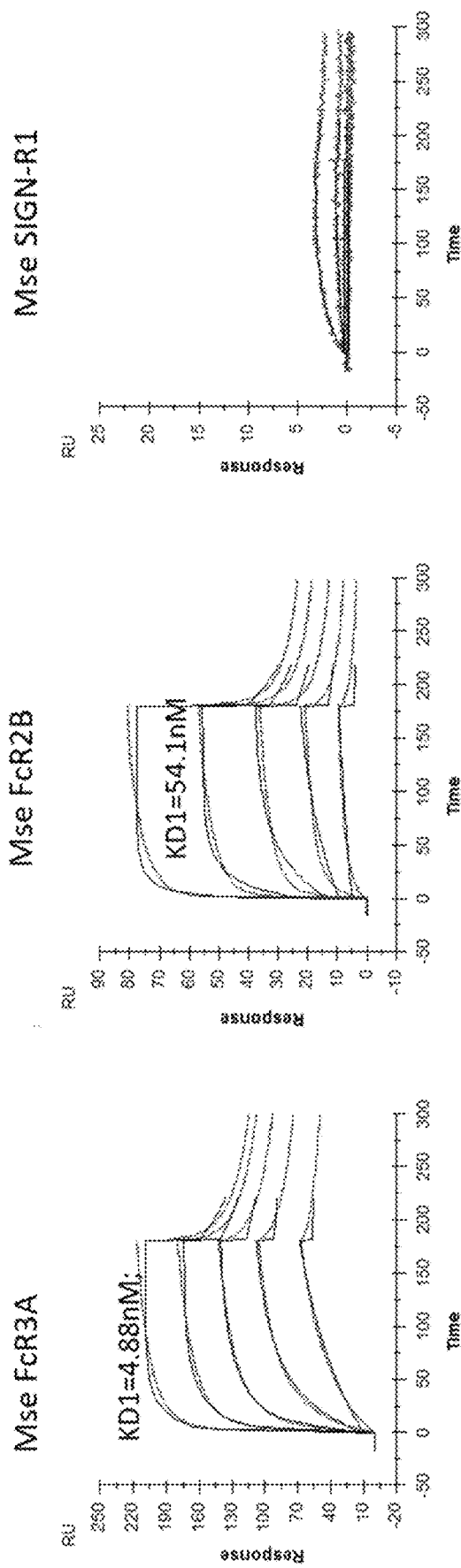
Figure 5E:
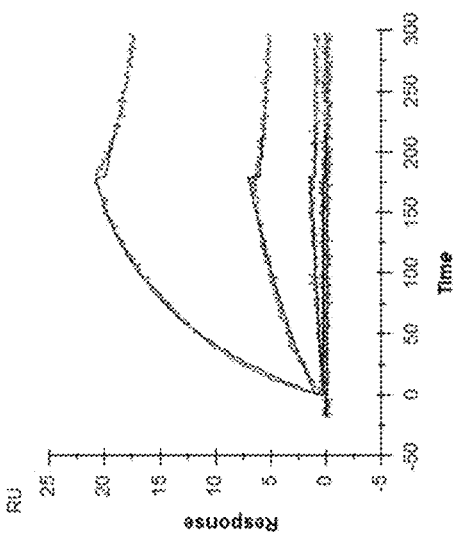
Figure 5E:
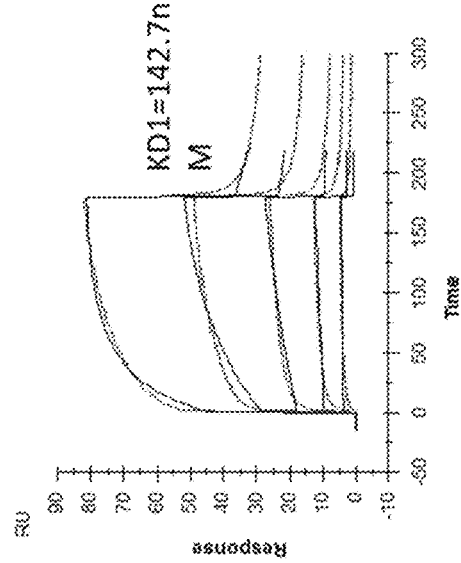
Figure 5E:
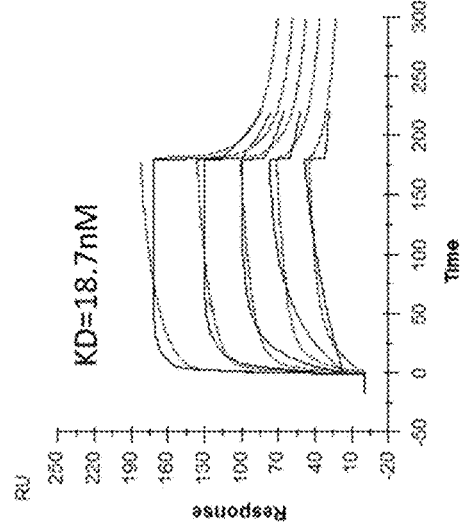

While high dose prednisolone (10 mg/kg) was effective as a single agent in ameliorating collagen induced arthritis, low dose prednisolone (2 mg/kg) was only marginally effective. Additionally, low dose M045c (200 μg/dose or 9.1 mg/kg) was also ineffective in decreasing disease severity compared to untreated controls. However, surprisingly, mice treated with low dose prednisolone combined with low dose M045c displayed a synergistic (more than additive) decrease in disease severity when compared to the prednisolone and M045c single treatment groups. (See FIG. 4).

Example 4: Binding Analysis of IgG2A, M045, M046, M028, M019 and G051 to Mouse Receptors FcγRIIIA, FcγRIIB and SIGN-R1 receptors were immobilized to a CM4 chip using amine immobilization to 560, 500, and 1000 RU, respectively to compensate for protein size.

M045c (SEQ ID NO:11), M046 (SEQ ID NO:15), M019 (SEQ ID NO:13) and M028 (SEQ ID NO:14) were serially diluted from 500 nM to 1.9 nM in HBSS-EP running buffer and injected at 20 ul/min for 180 sec. Regeneration was achieved by a 10 sec injection of 1M MgCl at 100 ul/min, followed by a brief wash with running buffer. KDs were calculated using T100 evaluation software.

For mouse FcγR3A and FcγR2b, mouse IgG2a Fc homodimers bind with lower affinity and faster dissociation rate as compared with each of the tested stradomers. For mouse SIGN-R1, mouse IgG2a Fc homodimers do not appreciably bind whereas selective stradomers associate to varying degrees and dissociate slowly. (See FIG. 5A-FIG. 5E).

M045c fractions were assessed in this model. M045F was first gel fractionated using an AktaXpress protein purification system and a GE HiLoad 16/60 Superdex 200 prep grade column. Fraction 1 (M045 F1) contains the highest molecular weight component of the M045 multimers after separation of multimers according to size. M045 F2 is the multimer component with lower molecular weight and M045 F3 is the homodimer fraction of the stradomer. For mouse FcγRIIIa, FcγRIIb (See FIG. 6A and FIG. 6B), and SIGN-R1 (See FIG. 6C and FIG. 6D) the binding affinity is highest with a slow dissociation rate for M045 F1 in comparison with other fractions or with IgG2a Fc control.

To assess the binding of G051, biolayer Interferometry assay was performed on an Octet 96 Red Instrument (ForteBio, Menlo Park CA) according to the manufacturer's instructions (Data Acquisition User Guide 6.4 ForteBio). For binding analysis of mouse protein, His-tagged mouse FcγRII (R&D system cat #1460-CD) and FcγRIII R&D system cat #1960) were separately loaded on anti-penta-His Biosensors (ForteBio cat #18-5077) at 10 μg/ml in 1× kinetic analysis buffer (ForteBio cat #18-5032). For binding analysis of human protein, His-tagged human FcγRIIb (R&D system cat #1875-CD) and FcγRIIIa R&D system cat #4325-Fc) were separately loaded on anti-penta-His Biosensors (ForteBio cat #18-5077) at 10 μg/ml in 1× kinetic analysis buffer (ForteBio cat #18-5032). Following sensor tip loading protein association was measured by transfer of tips to preparations of either monomeric fraction (over a range of concentrations) or the multimeric fractions (over a range of concentrations) in 1× kinetics analysis buffer and dissociation was measured by transfer of sensor tips to 1× kinetics buffer. Analysis was as described (Data Analysis User Guide 6.4ForteBio). Analysis was standardized as described above assigning a MW of 50 kD to homodimers and 150 kD to all other protein preparations.

Table 2 shows that larger stradomer multimer fractions of M051 bind with greater affinity and avidity and slower dissociation than smaller multimer fractions which in turn bind with greater affinity and avidity and slower dissociation than the homodimer fraction.

TABLE 2

| Sample | KD | Kon | Kdis | Rmax | R2 | Fraction |
|---|---|---|---|---|---|---|
| M051 | 6.55E−9 | 8.53E+5 | 5.59E−3 | 0.394 | 0.987 | |
| M051 monomer | 9.59E−7 | 7.24E+5 | 6.94E−1 | 0.373 | 0.985 | 2A11 |
| M051 dimer | 1.25E−8 | 1.45E+6 | 1.81E−2 | 0.4129 | 0.987 | 2H10 |
| M051 trimer | 3.36E−9 | 1.28E+6 | 4.28E−3 | 0.5093 | 0.996 | 3E12 |
| M051 tetramer | 1.39E−9 | 1.56E+6 | 2.04E−3 | 0.567 | 0.996 | 3H4 |
| M051 multimer | 1.77E−9 | 4.19E+6 | 1.15E−4 | 0.6237 | 0.998 | 4F4 |

To assess the binding kinetics of G045 or G051 relative to G001 (native IgG1 Fc), biolayer Interferometry assay was performed on an Octet 96 Red Instrument, as above. Binding of G045 and G001 to human FcγRIIb, FcγRIIIa (both the F and V variants), Cynomolgus FcγRIIIa, Cynomolgus FcγRIIIb and Cynomolgus FcγRIII was measured. G045 has a significantly higher binding affinity with slower dissociation and evidence of avidity to each of the tested receptors compared to G001. (See Tables 3 and 4).

TABLE 3

| Receptor | Protein | KD | kon | kdis | R max | R2 |
|---|---|---|---|---|---|---|
| Human FcγRIIb | G045 | 1.42E−9 | 7.99E+5 | 1.14E−3 | 0.7166 | 0.999 |
| Human FcγRIIIa (F) | G045 | 1.22E−9 | 6.20E+5 | 7.567E−4 | 0.7507 | 0.999 |
| Human FcγRIIIa (V) | G045 | 2.95E−10 | 6.07E+5 | 1.79E−4 | 0.9182 | 0.999 |
| Cynomolgus FcγRIIb | G045 | 1.19E−9 | 7.56E+5 | 8.81E−4 | 0.7125 | 0.999 |
| Cynomolgus FcγRIIIa | G045 | 2.58E−10 | 6.17E+5 | 1.59E−4 | 1.0356 | 0.999 |
| Mouse FcγRIIb | G045 | 5.42E−10 | 1.21E+6 | 6.56E−4 | 0.4555 | 0.998 |
| Mouse FcγRIII | G045 | 8.00E−10 | 1.03E+6 | 8.23E+4 | 0.519 | 0.998 |

TABLE 4

| Receptor | Protein | KD | kon | kdis | R max | R2 |
|---|---|---|---|---|---|---|
| Human FcγRIIb | G001 | 1.31E−6 | 6.86E+5 | 8.99E−1 | 0.19 | 0.986 |
| Human FcγRIIIa (F) | G001 | 2.43E−6 | 1.11E+5 | 2.69E−1 | 0.383 | 0.990 |
| Human FcγRIIIa (V) | G001 | 1.14E−6 | 1.18E+5 | 1.35E−1 | 0.7265 | 0.995 |
| Cynomolgus FcγRIIb | G001 | 2.04E−6 | 3.94E+5 | 8.06E−1 | 0.3456 | 0.988 |
| Cynomolgus FcγRIIIa | G001 | 9.15E−7 | 1.24E−5 | 1.14E−1 | 0.837 | 0.995 |
| Mouse FcγRII * | G001 | 1.51E−6 | 2.56E+5 | 3.87E−1 | 0.1173 | 0.963 * |
| Mouse FcγRIII * | G001 | 4.18E−6 | 1.18E+5 | 4.91E−1 | 0.1026 | 0.904 * |

Similarly, binding of G051 and G001 to human FcγRIIb, and FcγRIIIa was measured. G051 has a significantly higher binding affinity with slower dissociation and evidence of avidity to each of the tested receptors compared to G001. (See Tables).

TABLE 5

| Protein | Receptor | KD | Kon | Kdis | Rmax | R2 |
|---|---|---|---|---|---|---|
| G001 | FcγRIIb | 2.99E−06 | 3.72E+05 | 1.11E+00 | 0.3152 | 0.986 |
| G001 | FcγRIIIa | 6.77E−07 | 1.64E+05 | 1.11E−01 | 0.6535 | 0.991 |
| G051 | FcγRIIb | 4.39E−08 | 7.10E+05 | 3.12E−02 | 0.2868 | 0.991 |
| G051 | FcγRIIIa | 2.30E−08 | 2.83E+05 | 6.50E−03 | 0.886 | 0.996 |

Example 5: The Naturally Linked Stradomer Compounds are Effective in the Treatment/Prevention of ITP To elucidate the effect of stradomers in Idiopathic Thrombocytopeniaurpura (ITP) stradomers were tested in a preventative mouse model of ITP. Low platelet counts are induced following exposure to mouse integrin anti-IIb antibody which coats integrin receptors on platelets. Briefly, 8 week old C57BL/6 mice (Charles River) were tail vein injected with stradomer or control at day 1 following blood draw and platelet count. At day 2 following blood draw and platelet counts mice are treated with MWReg30 (BD Pharmingen cat #553847) given at a concentration of 2 μg of antibody in 200 ul of phosphate buffered saline administered by intraperitoneal injection to induce platelet loss. Blood draw for platelet counts and MWReg30 injections continue at days 3, 4, and 5. IVIG positive control is dosed daily on days 2 through 5 Platelet counts are taken with Drew Scientific Hemavet 950 hemocytometer. M045c and its fractions are dosed one time on day 2. Blood is collected by tail vein nicking and mixed with citrate buffer to prevent coagulation.

M045c is significantly protective in this model relative to both no drug treatment ITP control and IgG2a Fc control and is comparable to both IVIG preventative therapy and mice that did not receive the MWReg30 insult (See FIG. 7). M045c fractions were made as described in Example 4. M045 Fraction 1 is significantly protective in this model relative to no drug treatment ITP control whereas M045 Fraction 3 is not.

Example 6: Removal of Endotoxin Complexes With Naturally Linked Stradomer Complexes To remove endotoxin an endotoxin-containing protein solution containing a protein of interest will be adjusted to pH 7.2 with 1 volume of binding buffer (20 mM sodium phosphate pH7.2+150 mM NaCl) after mixing endotoxin binding stradomer to the solution. To remove the endotoxin the solution containing the protein will be applied to an affinity chromatography column (HiTrap Mabselect protein A affinity column, GE Life Sciences). The stradomer-bound endotoxin will bind to the affinity column and purified endotoxin free protein will elute in the flowthrough fractions.

In an alternative approach to using stradomers to trap endotoxin, protein A coated magnetic beads (New England BioLabs, MA) will be mixed into the endotoxin-containing protein solution together with endotoxin binding stradomers and the stradomer bound endotoxin will be removed by magnetic separation.

Example 7: Use of Naturally Linked Stradomer Complexes for Fc Blocking in Immunological Assays Improving the sensitivity and specificity of antibody-based research tools and clinical diagnostics. The research utility and clinical diagnostic utility of antibodies is limited by non-specific binding. This can occur, for example, by the binding of Fc portion of monoclonal or polyclonal antibodies to high affinity Fc gamma receptors and other Fc binding receptors on cells including immune cells and tumors or by the binding of antibody aggregates or cellular aggregates coated with antibody to low affinity Fc gamma receptors.

To demonstrate the ability of stradomers to block Fc gamma receptor interactions with specific anti-Fc gamma receptor antibodies we performed flow cytometry and compared increasing doses of human stradomer G045c with G001, a homodimeric monomer of IgG1 Fc, in their ability to block anti-FcγR antibody binding to FcγRs known to be present on specific cells. Stradomers were found to effectively block the binding of anti-FcγR antibodies binding to FcγRs relative to IgG1 Fc control and to do so in a concentration dependent manner (See FIG. 8A and FIG. 8B).

Because of their very high binding affinity for Fc gamma receptors and other receptors that bind immunoglobulin Fc regions, stradomers are surprisingly effective in blocking the binding and interaction even of specific anti-Fc gamma receptor monoclonal antibodies. Stradomers are therefore useful as control reagents to diminish non-specific antibody binding of administered antibodies in both the research tools setting and the clinical diagnostics setting.

Example 8: The Naturally Linked Stradomer Compounds are Effective in the Treatment of Experimental Autoimmune Neuritis Assessment of the efficacy of M045c and M051, in each case compared to that of IVIG and to albumin, was performed in an Experimental Autoimmune Neuritis (EAN) rat model. Murine EAN models are widely used animal models of human acute inflammatory demyelinating polyradiculoneuropathy. Briefly, 45 Lewis rats were immunized with whole bovine peripheral nerve myelin and randomized into three groups. At the onset of clinical deficits, which is generally weight loss beginning at day 9 or 10, 15 rats per treatment group were treated with IVIg (1 gm/1 Kg body weight), M045 (20 mg/Kg) or M051 (17.5 mg/Kg) or with albumin all given as two doses IV on two consecutive days. All drugs were administered intravenously by tail vein injection.

EAN rats were assessed clinically, electrophysiologically, and histologically. The clinical disease severity was evaluated by daily clinical grading and by weight changes. The electrophysiological studies included examining the amplitude of compound muscle action potentials (CMAPs) and motor conduction velocity (MCV). On day 15 at the peak of the disease, five rats from each group were sacrificed, sciatic nerves collected and histopathological changes analyzed. The treatment efficacy was compared between IVIg and albumin groups, and the recombinant M045c or M051 and albumin groups.

Rats receiving the tested stradomer M045c had statistically less severe disease than albumin treated controls (see FIG. 12A-FIG. 12E). EAN rats treated with albumin presented higher mortality (4 out of 15) compared to IVIg-treated (1 out of 15) and to M045c-treated rats (0 out of 15). Animals receiving M045c and IVIg treatment exhibited significantly less prominent weight loss. There was a statistically significant improvement in both motor conduction velocity (MCV) and the amplitudes of distal and proximal CMAPs in IVIg and M045c treated rats compared to those treated with albumin. Albumin treated rats showed more severe axonal loss and active axonal degeneration in sciatic nerves compared to rats treated with IVIg or with M045c. Thus, the stradomer M045c demonstrated mortality, weight, clinical, electrophysiological, and histopathological efficacy in comparison with albumin, comparable to the efficacy demonstrated by the clinical gold standard IVIg at approximately 2% of the dose of IVIg.

In a separate experiment with 11 rats per test group, rats receiving the tested stradomer M051 had statistically less severe disease than albumin treated controls (see FIG. 11A FIG. 11E). In this study, 7 out of 11 animals died in the control (albumin) group compared to 4 in the M051 group. Rats receiving either IVIg or M051 demonstrated significantly less weight loss compared with rats receiving albumin control. Rats receiving either IVIg or M051 demonstrated significant improvement in clinical scores compared with rats receiving albumin control. There was a statistically significant improvement in both MCV and in the amplitude of CMAPs following treatment with IVIg or M051. Thus, the stradomer M051 demonstrated significant mortality, weight, clinical, and electrophysiological efficacy in comparison with albumin, comparable to the efficacy demonstrated by the clinical gold standard IVIg at approximately 2% of the dose of IVIg.

Example 9: Naturally Linked Stradomer Compounds Containing Fc Mutations Display Enhanced Binding to FcγRs and are Effective for Treatment in a Mouse Model of Arthritis Binding of the Fc mutant-containing stradomers, G075 (SEQ ID NO: 20) and G076 (SEQ ID NO: 21) to FcγRIIIa, FcγRIIb and FcγRIIa was performed by Biacore binding assay as described above in Example 4. G075 showed an increase in binding to FcγRIIIa and a decrease in binding to FcγRIIa and FcγRIIb while G076 showed a decrease in binding to FcγRIIIa and an increase in binding to FcγRIIa and FcγRIIb. (See FIG. 10A and FIG. 10B).

Assessment of the efficacy of the Fc mutant containing stradomers M075 (SEQ ID NO: 22), M076 (SEQ ID NO: 23) and M098 (SEQ ID NO: 25) on a mouse model of arthritis was next determined as was done in Example 3 above. The Fc mutant-containing stradomers were compared to vehicle and M045c. Both M098 and M075 were significantly more effective at inhibiting the progression of CIA, while the M076 stradomer was not. (See FIG. 13A and FIG. 13B). We expect that other mutations of immunoglobulin Fc that are known to alter individual Fc-FcR binding or that alter complement dependent cytotoxicity will be similarly complementary to stradomers comprising IgG1 Fc and presenting polyvalent IgG1 Fc to Fc receptors.

What is claimed is:

1. A method of treating an inflammatory disease or autoimmune disease in a subject in need thereof comprising administering to the subject an effective amount of a pharmaceutical composition comprising a multimerized compound comprising two or more homodimeric stradomer units,
wherein each homodimeric stradomer unit comprises two stradomer unit monomers, and
wherein each stradomer unit monomer comprises amino acid residues 21-264 of SEQ ID NO:4.

2. The method of claim 1, wherein the multimerized compound comprises 2, 3, 4, 5, 6, 7, or more homodimeric stradomer units.

3. The method of claim 1, wherein the pharmaceutical composition comprises higher order multimers.

4. The method of claim 1, wherein the autoimmune or inflammatory disease is capable of being treated with human IVIG.

5. The method of claim 1, wherein the inflammatory or autoimmune disease is selected from multifocal motor neuropathy (MMN), Alzheimer's disease, sepsis, arthritis, multiple sclerosis, autoimmune thyroiditis, chronic inflammatory polyneuropathy, *scleroderma*, autoimmune uveitis, systemic lupus erythematosus (SLE), myasthenia *gravis*, atopic dermatitis, a disease associated with the transplantation of an organ from a donor to a recipient, or an infectious disease, a bacterial infection, or a viral infection, acquired autoimmune thrombocytopenia, acquired factor VIII autoimmunity, acquired von Willebrand disease, acute idiopathic dysautonomic neuropathy, alloimmune/autoimmune thrombocytopenia, ANCA positive vasculitis, ankylosing spondylitis, anti-decorin (BJ antigen) myopathy, aplastic anemia, asthma, autoimmune anemia, autoimmune hemolytic anemia, autoimmune neutropenia, bone marrow transplantation rejection, celiac disease, chronic inflammatory demyelinating polyneuropathy (CIDP), chronic inflammatory demyelinating polyradiculoneuropathy, chronic lymphocytic leukemia (CLL), Crohn's disease, Cushing syndrome, dermatomyositis, dermatopolymyositis, diabetic neuropathy, Diamond-Blackfan anemia, epilepsy, Evan's syndrome, Felty's syndrome, Gaucher's disease, Goodpasture's disease, Grave's disease, Guillain-Barré syndrome, hemolytic disease of the newborn, hemolytic uremic syndrome, idiopathic thrombocytopenia purpura (ITP), immune-mediated neutropenia, inclusion-body myositis, inflammatory bowel disease, inflammatory myopathies, juvenile idiopathic arthritis, Kawasaki disease, Lambert-Eaton myasthenic syndrome, lower motor neuron syndrome associated with anti-GM1, monoclonal gammopathy of unknown significance, myelitis, myositis, necrotizing fasciitis, optic neuritis, organ transplantation rejection, Paget's disease, paraneoplastic cerebellar degeneration anti-Yo with antibodies, paraneoplastic encephalomyelitis, paraneoplastic necrotic myopathy, paraproteinemic IgM demyelinating polyneuropathy, *pemphigus*, penacillamine induced polymyositis, post-transfusion purpura, psoriasis, pure red cell aplasia, reactive arthritis, refractoriness to platelet transfusion, rheumatoid arthritis, sarcoidosis, sclerosing cholangitis, sensory neuropathy with anti-Hu antibodies, sepsis, sickle cell crisis, spondyloarthropathies, spontaneous polymyositis, Stiff Man Syndrome, systemic vasculitis, thrombotic thrombocytopenia purpura, type I diabetes mellitus, ulcerative colitis, Wegener's granulomatosis, Whipple's disease, and X-linked vacuolated myopathy.

6. A method of treating an inflammatory disease or autoimmune disease in a subject in need thereof comprising administering to the subject an effective amount of a pharmaceutical composition comprising a multimerized compound comprising two or more homodimeric stradomer units,
wherein each homodimeric stradomer unit consists of two stradomer unit monomers, and
wherein each stradomer unit monomer consists of amino acid residues 21-264 of SEQ ID NO:4.

7. The method of claim 6, wherein the multimerized compound comprises 2, 3, 4, 5, 6, 7, or more homodimeric stradomer units.

8. The method of claim 6, wherein the pharmaceutical composition comprises higher order multimers.

9. The method of claim 6, wherein the autoimmune or inflammatory disease is capable of being treated with human IVIG.

10. The method of claim 6, wherein the inflammatory or autoimmune disease is selected from multifocal motor neuropathy (MMN), Alzheimer's disease, sepsis, arthritis, multiple sclerosis, autoimmune thyroiditis, chronic inflammatory polyneuropathy, *scleroderma*, autoimmune uveitis, systemic lupus erythematosus, myasthenia *gravis*, atopic dermatitis, a disease associated with the transplantation of an organ from a donor to a recipient, or an infectious disease, a bacterial infection, or a viral infection, acquired autoimmune thrombocytopenia, acquired factor VIII autoimmunity, acquired von Willebrand disease, acute idiopathic dysautonomic neuropathy, alloimmune/autoimmune thrombocytopenia, ANCA positive vasculitis, ankylosing spondylitis, anti-decorin (BJ antigen) myopathy, aplastic anemia, asthma, autoimmune anemia, autoimmune hemolytic anemia, autoimmune neutropenia, bone marrow transplantation rejection, celiac disease, chronic inflammatory demyelinating polyneuropathy (CIDP), chronic inflammatory demyelinating polyradiculoneuropathy, chronic lymphocytic leukemia (CLL), Crohn's disease, Cushing syndrome, dermatomyositis, dermatopolymyositis, diabetic neuropathy, Diamond-Blackfan anemia, epilepsy, Evan's syndrome, Felty's syndrome, Gaucher's disease, Goodpasture's disease, Grave's disease, Guillain-Barré syndrome, hemolytic disease of the newborn, hemolytic uremic syndrome, idiopathic thrombocytopeniarpura (ITP), immune-mediated neutropenia, inclusion-body myositis, inflammatory bowel disease, inflammatory myopathies, juvenile idiopathic arthritis, Kawasaki disease, Lambert-Eaton myasthenic syndrome, lower motor neuron syndrome associated with anti-GM1, monoclonal gammopathy of unknown significance, myelitis, myositis, necrotizing fasciitis, optic neuritis, organ transplantation rejection, Paget's disease, paraneoplastic cerebellar degeneration with anti-Yo antibodies, paraneoplastic encephalomyelitis, paraneoplastic necrotic myopathy, paraproteinemic IgM demyelinating polyneuropathy, *pemphigus*, penacillamine induced polymyositis, post-transfusion purpura, psoriasis, pure red cell aplasia, reactive arthritis, refractoriness to platelet transfusion, rheumatoid arthritis, sarcoidosis, sclerosing cholangitis, sensory neuropathy with anti-Hu antibodies, sepsis, sickle cell crisis, spondyloarthropathies, spontaneous polymyositis, Stiff Man Syndrome, systemic vasculitis, thrombotic thrombocytopenia purpura, type I diabetes mellitus, ulcerative colitis, Wegener's granulomatosis, Whipple's disease, and X-linked vacuolated myopathy.

11. A method of treating an inflammatory disease or autoimmune disease in a subject in need thereof comprising administering to the subject an effective amount of a pharmaceutical composition comprising a multimerized compound comprising two or more homodimeric stradomer units,
wherein each homodimeric stradomer unit comprises two stradomer unit monomers, each stradomer unit monomer comprising the amino acid sequence of SEQ ID NO:2 directly linked at its carboxy terminus to the amino acid sequence of SEQ ID NO:3.

12. The method of claim 11, wherein the multimerized compound comprises 2, 3, 4, 5, 6, 7, or more homodimeric stradomer units.

13. The method of claim 11, wherein the pharmaceutical composition comprises higher order multimers.

14. The method of claim 11, wherein the autoimmune or inflammatory disease is capable of being treated with human IVIG.

15. The method of claim 11, wherein the inflammatory or autoimmune disease is selected from multifocal motor neuropathy (MMN), Alzheimer's disease, sepsis, arthritis, multiple sclerosis, autoimmune thyroiditis, chronic inflammatory polyneuropathy, *scleroderma*, autoimmune uveitis, systemic lupus erythematosus, myasthenia *gravis*, atopic dermatitis, a disease associated with the transplantation of an organ from a donor to a recipient, or an infectious disease, a bacterial infection, or a viral infection, acquired autoimmune thrombocytopenia, acquired factor VIII autoimmunity, acquired von Willebrand disease, acute idiopathic dysautonomic neuropathy, alloimmune/autoimmune thrombocytopenia, ANCA positive vasculitis, ankylosing spondylitis, anti-decorin (BJ antigen) myopathy, aplastic anemia, asthma, autoimmune anemia, autoimmune hemolytic anemia, autoimmune neutropenia, bone marrow transplantation rejection, celiac disease, chronic inflammatory demyelinating polyneuropathy (CIDP), chronic inflammatory demyelinating polyradiculoneuropathy, chronic lymphocytic leukemia (CLL), Crohn's disease, Cushing syndrome, dermatomyositis, dermatopolymyositis, diabetic neuropathy, Diamond-Blackfan anemia, epilepsy, Evan's syndrome, Felty's syndrome, Gaucher's disease, Goodpasture's disease, Grave's disease, Guillain-Barré syndrome, hemolytic disease of the newborn, hemolytic uremic syndrome, idiopathic thrombocytopeniaurpura (ITP), immune-mediated neutropenia, inclusion-body myositis, inflammatory bowel disease, inflammatory myopathies, juvenile idiopathic arthritis, Kawasaki disease, Lambert-Eaton myasthenic syndrome, lower motor neuron syndrome associated with anti-GM1, monoclonal gammopathy of unknown significance, myelitis, myositis, necrotizing fasciitis, optic neuritis, organ transplantation rejection, Paget's disease, paraneoplastic cerebellar anti-Yo degeneration with antibodies, paraneoplastic encephalomyelitis, paraneoplastic necrotic myopathy, paraproteinemic IgM demyelinating polyneuropathy, *pemphigus*, penacillamine induced polymyositis, post-transfusion purpura, psoriasis, pure red cell aplasia, reactive arthritis, refractoriness to platelet transfusion, rheumatoid arthritis, sarcoidosis, sclerosing cholangitis, sensory neuropathy with anti-Hu antibodies, sepsis, sickle cell crisis, spondyloarthropathies, spontaneous polymyositis, Stiff Man Syndrome, systemic vasculitis, thrombotic thrombocytopenia purpura, type I diabetes mellitus, ulcerative colitis, Wegener's granulomatosis, Whipple's disease, and X-linked vacuolated myopathy.

\* \* \* \* \*